(12) United States Patent
Boyd

(10) Patent No.: US 6,780,847 B2
(45) Date of Patent: Aug. 24, 2004

(54) GLYCOSYLATION-RESISTANT CYANOVIRINS AND RELATED CONJUGATES, COMPOSITIONS, NUCLEIC ACIDS, VECTORS, HOST CELLS, METHODS OF PRODUCTION AND METHODS OF USING NONGLYCOSYLATED CYANOVIRINS

(75) Inventor: Michael R. Boyd, Ijamsville, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 09/815,079

(22) Filed: Mar. 22, 2001

(65) Prior Publication Data

US 2002/0127675 A1 Sep. 12, 2002

Related U.S. Application Data

(63) Continuation-in-part of application No. 09/416,434, filed on Oct. 12, 1999, now Pat. No. 6,428,790, which is a continuation-in-part of application No. 09/267,447, filed on Mar. 12, 1999, now abandoned, which is a continuation-in-part of application No. 08/969,378, filed on Nov. 13, 1997, now Pat. No. 6,015,876, which is a division of application No. 08/429,965, filed on Apr. 27, 1995, now Pat. No. 5,843,882, said application No. 09/416,434, is a continuation-in-part of application No. 08/969,689, filed on Nov. 13, 1997, which is a division of application No. 08/638,610, filed on Apr. 26, 1996, now Pat. No. 5,821,081, which is a continuation-in-part of application No. 08/429,965.

(51) Int. Cl.[7] .................... A61K 38/04; A61K 38/06; C07K 14/00; C07K 7/00; C12N 15/31

(52) U.S. Cl. .................... 514/12; 514/13; 514/14; 514/15; 514/44; 530/324; 530/325; 530/326; 530/327; 530/328; 530/402; 536/23.7; 435/320.1; 435/325; 435/69.1; 800/13

(58) Field of Search .................... 514/12–15, 44; 536/23.7; 435/320.1, 325, 252.3, 254.11, 69.1; 530/350, 324–328, 402; 424/53.21; 800/13

(56) References Cited

U.S. PATENT DOCUMENTS

| | | | |
|---|---|---|---|
| 3,470,067 A | | 9/1969 | Warren et al. |
| 5,266,478 A | | 11/1993 | Chang et al. |
| 5,445,960 A | | 8/1995 | Masuho et al. |
| 5,558,865 A | | 9/1996 | Ohno |
| 5,618,922 A | | 4/1997 | Ohno et al. |
| 6,420,336 B1 | * | 7/2002 | Boyd ............... 514/2 |

FOREIGN PATENT DOCUMENTS

| | | |
|---|---|---|
| CA | 2124545 | 11/1995 |
| DE | 3828842 | 10/1989 |
| EP | 459779 | 12/1991 |
| EP | 465979 | 1/1992 |
| EP | 503916 | 9/1992 |
| EP | 516135 | 5/1993 |
| EP | 581353 | 2/1994 |
| JP | 6141885 | 5/1994 |
| PT | 95939 | 9/1991 |
| WO | WO 90/12868 | 11/1990 |
| WO | WO 91/09625 | 7/1991 |
| WO | WO 91/11198 | 8/1991 |
| WO | WO 91/17764 | 11/1991 |
| WO | WO 92/07878 | 5/1992 |
| WO | WO 92/08491 | 5/1992 |
| WO | WO 92/08983 | 5/1992 |
| WO | WO 92/15885 | 9/1992 |
| WO | WO 93/04090 | 3/1993 |
| WO | WO 93/06216 | 4/1993 |
| WO | WO 93/12232 | 6/1993 |
| WO | WO 94/04574 | 3/1994 |
| WO | WO 94/07922 | 4/1994 |
| WO | WO 94/19017 | 9/1994 |
| WO | WO 94/28933 | 12/1994 |
| WO | WO 95/06119 | 3/1995 |
| WO | WO 95/24215 | 9/1995 |
| WO | WO 96/02273 | 2/1996 |
| WO | WO 96/34107 | 10/1996 |
| WO | WO 96/40294 | 12/1996 |
| WO | WO 99/19500 | 4/1999 |

OTHER PUBLICATIONS

Mori et al (BBRC 238:218–222, 1997).*

Sato et al (Antiviral Research 27:151–163, 1995).*

Rice et al (Advances in Pharmacology 33:389–438, 1995).*

Dey et al (Journal of Virology 74:4562, May 2000).*

Abuchowski et al., "Soluble Polymer–Enzyme Adducts," in *Enzymes as Drugs*, Holcenberg et al., eds., John Wiley: New York, 1981, pp. 367–383.

(List continued on next page.)

*Primary Examiner*—Mary E. Mosher
(74) *Attorney, Agent, or Firm*—Leydig, Voit & Mayer, Ltd

(57) ABSTRACT

An isolated and purified nucleic acid molecule that encodes a protein or peptide comprising at least nine contiguous amino acids of SEQ ID NO:2, wherein the at least nine contiguous amino acids comprise amino acids 30–32 of SEQ ID NO: 2 which have been rendered glycosylation resistant and wherein the at least nine contiguous amino acids have antiviral activity, a vector comprising such an isolated and purified nucleic acid molecule, a host cell or organism comprising the vector, a method of producing an antiviral protein or antiviral peptide, the antiviral protein or antiviral peptide itself, a conjugate comprising the antiviral protein or antiviral peptide, and compositions comprising an effective amount of the antiviral protein, antiviral peptide, antiviral protein conjugate or antiviral peptide conjugate. Further provided is a method of inhibiting prophylactically or therapeutically a viral infection, specifically an influenza viral infection, of a host.

57 Claims, 14 Drawing Sheets

OTHER PUBLICATIONS

Abuchowski et al., Alteration of Immunological Properties of Bovine Serum Albumin by Covalent Attachment of Polyethylene Glycol, *Journal of Biological Chemistry*, 252(11), 3578–3581 (1977).

Agnew et al., "The Effect of Treatment Regimens for Vaginitis and Cervicitis on Vaginal Colonization by *Lactobacilli*," *Sexually Transmitted Diseases*, 22 (5), 269–273 (1995).

Andreu et al., "Hemagglutination, Adherence, and Surface Properties of Vaginal *Lactobacillus* Species," *J. Infect. Diseases*, 171, 1237–1243 (1995).

Aullo et al., "A Recombinant Diphtheria Toxin Related Human CD4 Fusion Protein Specifically Kills HIV Infected Cells Which Express gp120 But Selects Fusion Toxin Resistant Cells Which Carry HIV," *EMBO Journal*, 11(2), 575–583 (1992).

Balter, "UN Readies New Global AIDS Plan," *Science*, 266, 1312–1313 (1994).

Banga et al., "Systemic Delivery of Therapeutic Peptides and Proteins," *International Journal of Pharmaceutics*, 48, 15–50 (1988).

Barry, "The Transdermal Route for the Delivery of Peptides and Proteins," in *Delivery Systems for Peptide Drugs*, Davis et al., eds., Plenum Press: New York, 1986, pp. 265–275.

Berzofsky, "Approaches and Issues in the Development of Vaccines Against HIV," *Journal of Acquired Immune Deficiency Syndromes*, 4, 451–459 (1991).

Bird, "The Use of Spermicide Containing Nonoxynol–9 in the Prevention of HIV Infection," *AIDS*, 5(7), 791–796 (1991).

Bourinbaiar et al., "Anti–HIV Effect of Gramicidin In Vitro: Potential for Spermicide Use," *Life Sciences*, 54(1), 5–9 (1994).

Bourinbaiar et al., "Comparative In Vitro Study of Contraceptive Agents with Anti–HIV Activity: Gramicidin, Nonoxynol–9, and Gossypol," *Contraception*, 49, 131–137 (1994).

Bowie et al., "Deciphering the Message in the Protein Sequences: Tolerance to Amino Acid Substitutions," *Science*, 247, 1306–1310 (1990).

Boyd et al., "Discovery of Cyanovirin–N, a Novel Human Immunodeficiency Virus–Inactivating Protein That Binds Viral Surface Envelope Glycoprotein gp120: Potential Applications to Microbicide Development", *Antimicrobial Agents and Chemotherapy*, 41(7), 1521–1530 (1997).

Boyd, "Strategies for the Identification of New Agents for the Treatment of AIDS: A National Program to Facilitate the Discovery and Preclinical Development of New Drug Candidates for Clinical Evaluation," *AIDS Etiology, Diagnosis, Treatment, and Prevention*, Second Edition, DeVita et al., eds., J.B. Lippincott Company, 1988, pp. 305–317.

Boyd et al., "Anti–HIV Michellamines from *Ancistrocladus korupensis*," *Journal of Medicinal Chemistry*, 37(12), 1740–1745 (1994).

Bruce et al., "Intravaginal instillation of *Lactobacilli* for Prevention of Recurrent Urinary Tract Infections," *Can. J. Microbiol.*, 34, 339–343 (1988).

Buckheit et al., "Biological and Biochemical Anti–HIV Activity of the Benzothiadiazine Class Nonnucleoside Reverse Transcriptase Inhibitors," *Antiviral Research*, 25, 43–56 (1994).

Buckheit et al., "Potent and Specific Inhibition of HIV Envelope–Mediated Cell Fusion and Virus Binding by G Quartet–Forming Ogionucleotide (ISIS 5320)," *AIDS Research and Human Retroviruses*, 10(11), 1497–1506 (1994).

Capon et al., "Designing CD4 Immunoadhesins for AIDS Therapy," *Nature*, 337, 525–531 (1989).

Capon et al., "The CD4–gp120 Interaction and AIDS Pathogenesis," *Annu. Rev. Immunol.*, 9, 649–678 (1991).

Carone et al., "Renal Tubular Processing of Small Peptide Hormones," *The Journal of Laboratory and Clinical Medicine*, 100(1), 1–14 (1982).

Carpenter et al., *JAMA*, 280(1), 78–86 (1998).

Carter et al., "Structure of Majusculamide C, a Cyclic Depsipeptide from *Lyngbya majuscula*," *J. Org. Chem.*, 49, 236–241 (1984).

Chan et al., "HIV Entry and its Inhibition," *Cell*, 93, 681–684 (1998).

Chaudhary et al., "Selective Killing of HIV–Infected Cells by Recombination Human CD4–*Pseudomonas* Exotoxin Hybrid Protein," *Nature*, 335, 369–372 (1988).

Chaudhary et al., "CD4–PE4O—A Chimeric Toxin Active Against Human Immunodeficiency Virus (HIV)–Infected Cells," *The Human Retroviruses*, pp. 379–387 (1991).

Coffin, John M., "HIV Population Dynamics In Vivo: Implications for Genetic Variation, Pathogenesis, and Therapy," *Science*, 267, 483–489 (1995).

Cohen, "High Turnover of HIV in Blood Revealed by New Studies," *Science*, 267, 179 (1995).

Cohen et al., *JAMA* 280(1), 87–88 (1998).

Coll et al., "The Application of Vacuum Liquid Chromatograph to the Separation of Terpene Mixtures," *Journal of Natural Products*, 49(5), 934–936 (1986).

Davey et al., "Use of Recombinant Soluble CD4 *Pseudomonas* Exotoxin, a Novel Immunotoxin, for Treatment of Persons Infected with Human Immunodeficiency Virus," *Journal of Infectious Diseases*, 170, 1180–1188 (1994).

Davis, "Delivery Systems for Biopharmaceuticals," *J. Pharm. Pharmacol.*, 44(Suppl. 1), 186–190 (1992).

Davis, et al., "Reduction of Immunogenicity and Extension of Circulating Half–Life of Peptides and Proteins," *Peptide and Protein and Drug Delivery*, Marcel Dekker, Inc., New York: 1991 (831–864).

De Clercq, "Antiviral Agents: Characteristics Activity Spectrum Depending on the Molecular Target with Which They Interact," *Advances In Virus Research*, 42, 1–55, (1993).

De Clercq, "Basic Approaches to Anti–Retroviral Treatment," *Journal of Acquired Immune Deficiency Syndromes*, 4(3), 207–218 (1991).

Deasy et al., in *Microencapsulation and Related Processes*, Swarbrick J., ed., Marcel Dekker, Inc.: New York, 1984, pp. 1–60.

Denton et al., "Clinical Outcome of Colorectal Cancer Patients Treated with Human Monoclonal Anti–Idiotypic Antibody," *Int. J. Cancer*, 57, 10–14 (1994).

Elmer et al., "Biotherapeutic Agents," *JAMA*, 275(11), 870–876 (1996).

Emtage, "Biotechnology and Protein Production," in *Delivery Systems for Peptide Drugs*, Davis et al., eds., Plenum Press: New York, 1986, pp. 23–33.

Eppstein et al., "Alternative Delivery Systems for Peptides and Proteins as Drugs," *CRC Critical Reviews in Therapeutic Drug Carrier Systems*, 5(2), 99–139 (1988).

Faulkner, "Marine Natural Products," *Natural Product Reports*, pp. 355–394 (1994).

Frankmölle et al., "Antifungal Cyclic Peptides from the Terrestrial Blue–Green Alga *Anabaena laxa*," *The Journal of Antibiotics, 45*(9), 1451–1457 (1992).

Freed et al., "The Role of the HIV Envelope Glycoproteins in Cell Fusion and the Pathogenesis of AIDS," *Bull. Inst. Pasteur, 88*, 73–110 (1990).

Fung et al., *Journal of Immunology, 145*(7), 2199–2206 (1990).

Glombitza et al, in *Algal and Cyanobacterial Biotechnology*, Cresswell, R.C., et al., eds., 1989, pp. 211–218.

Goudswaard et al., "Protein A Reactivity of Various Mammalian Immunoglobulins," *Scand. J. Immunol., 8*, 21–28 (1978).

Greenspan et al., "Idiotypes: Structure and Immunogenicity," *The FASEB Journal, 7*, 437–444 (1993).

Gulakowski et al., "A Semiautomated Multiparameter Approach for Anti–HIV Drug Screening," *Journal of Virological Methods, 33*, 87–100 (1991).

Gustafson et al., "A Nonpromoting Phorbol from the Samoan Medicinal Plant *Homalanthus nutans* Inhibits Cell Killing by HIV–1," *J. Med. Chem., 35*, 1978–1986 (1982).

Guyden, "Techniques for Gene Cloning and Expression," in *Recombinant DNA Technology Concepts and Biomedical Applications*, Steinberg et al., eds., Prentice Hall: Englewood Cliffs, NJ, 1993, pp. 81–124 and 150–162.

Harris, "Introduction to Biotechnical and Biomedical Applications of Poly(Ethylene Glycol)", *Poly(Ethylene Glycol) Chemistry: Biotechnical and Biomedical Applications*, Plenum Press, New York: 1992 (1–14).

Haynes, "HIV Vaccines: Where we are and where we are going," *The Lancet, 348*(9043), 1741 abstract only (1996).

Hillier et al., "The Normal Vaginal Flora, $H_2O_2$–Producing *Lactobacilli*, and Bacterial Vaginosis in Pregnant Women," *Clinical Infectious Diseases, 16*, S273–S281 (1993).

Hillier, "A Healthy Vaginal Ecosystem is Important for Prevention of HIV Transmission: Why and How?," presented at *Conference on Advances in AIDS Vaccine Development*, Bethesda, Maryland (Feb. 11–15, 1996).

Holmberg et al., "Immobilization of Proteins via PEG Chains", *Poly(Ethylene Glycol) Chemistry: Biotechnical and Biomedical Applications*, Plenum Press, New York: 1992 (303–324).

Hols et al., "Use of Homologous Expression–Secretion Signals and Vector–Free Stable Chromosomal Integration in Engineering of *Lactobacillus* Plantarum for α–Amylase and Levanase Expression," *Applied and Environmental Microbiology, 60*(5), 1401–1413 (1994).

Husson et al., "Phase 1 Study of Continuous–Infusion Soluble CD4 as a Single Agent and In Combination with Oral Dideoxyinosine Therapy in Children with Symptomatic Human Immunodeficiency Virus Infection," *The Journal of Pediatrics, 121*(4), 627–633 (1992).

Kashman et al., "The Calonolides, a Novel HIV–Inhibitory Class of Coumarin Derivatives from the Tropical Rainforest Tree, *Calophyllum lanigerum*," *Journal of Medicinal Chemistry, 35*(15), 2735–2743 (1992).

Koenig et al., "Selective Infection of Human CD4+ Cells by Simian Immunodeficiency Virus: Productive Infection Associated with Envelope Glycoprotein–Induced Fusion," *Proc. Natl. Acad. Sci. USA, 86*, 2443–2447 (1989).

Krietman et al., "Recombinant Immunotoxins Containing Anti–Tac(FV) and Derivatives of Pseudomonas Exotoxin Produce Compete Regression in Mice of an Interleukin–2 Receptor–Expressing Human Carcinoma," *Blood, 83*(2), 426–434 (1994).

Krishnamurthy et al., "Structural Characterization of Toxic Cyclic Peptides from Blue–Green Algae by Tandem Mass Spectrometry," *Proc. Natl. Acad. Sci. USA, 86*, 770–774 (1989).

Laemmli, "Cleavage of Structural Proteins During the Assembly of the Head of Bacteriophage T4," *Nature, 227*, 680–685 (1970).

Lange et al., "Boost for Vaginal Microbicides Against HIV," *The Lancet, 341*, 1356 (1993).

Langner, "Antiviral Effects of Different CD4–Immunoglobulin Constructs Against HIV–1 and SIV: Immunological Characterization, Pharmacokinetic Data and In Vivo Experiments," *Arch. Virol., 130*, 157–170 (1993).

Letvin, *Science, 280*, 1875–1880 (1998).

Lin et al., "Selective Inhibition of Human Immunodeficiency Virus Type 1 Replication by the (–) but Not the (+) Enantiomer of Gossypol," *Antimicrob. Agents Chemother., 33*(12), 2149–2151 (1989).

Lipton, "HIV Displays Its Coat of Arms," *Nature, 367*, 113–114 (1994).

Lisi et al., "Enzyme Therapy: I. Polyethylene Glycol:☐–Glucuronidase Conjugates as Potential Therapeutic Agents in Acid Mucopolysaccharidosis,"*J. Appl. Biochem., 4*, 19–33 (1982).

Madiyalakan, et al., "Anitidiotype Induction Therapy: Evidence for the Induction of Immune Response through the Idiotype Network in Patients with Ovarian Cancer after Administration of Anti–CA125 Murine Monoclonal Antibody b43.13," *Hybridoma, 14*, (2), 199–203 (1995).

Matsushita et al., "Characterization of a Human Immunodeficiency Virus Neutralizing Monoclonal Antibody and Mapping of the Neutralizing Epitope," *Journal of Virology, 62*(6), 2107–2114 (1988).

Maulding, "Prolonged Delivery of Peptides by Microcapsules," *Journal of Controlled Release, 6*, 167–176 (1987).

McCaffrey et al., "A Rapid Fluorometic DNA Assay for the Measurement of Cell Density and Proliferation In Vitro," *In Vitro Cellular & Developmental Biology, 24*(3), 247–252 (1988).

McGroarty, "Probiotic Use of *Lactobacilli* in the Human Female Urogenital Tract," *FEMS Immunology and Medical Microbiology, 6*, 251–264 (1993).

Merigan, "Treatment of AIDS with Combinations of Antiretroviral Agents," *The American Journal of Medicine, 90*(Supp. 4A), 8S–17S (1991).

Merson, "Slowing the Spread of HIV: Agenda for the 1990s," *Science, 260*, 1266–1268 (1993).

Michalowski et al., "A Novel Allophycocyanin Gene (apcD) from *Cyanophora paradoxa* Cyanelles," *Nucleic Acids Research, 18*(8), 2186 (1990).

Mitsuya et al., "Molecular Targets for AIDS Therapy," *Science, 249*, 1533–1544 (1990).

Moore et al., "Sensitive ELISA for the gp120 and gp160 Surface Glycoproteins of HIV–1," *AIDS Research and Human Retroviruses, 4*(5), 369–379 (1988).

Moore et al., "Virions of Primary Human Immunodeficiency Virus Type 1 Isolates Resistant to Soluble CD4 (sCD4) Neutralization Differ in sCD4 Binding and Glycoprotein gp120 Retention from sCD4–Sensitive Isolates,"*Journal of Virology*, 66(1), 235–243 (1992).

Morgan et al., "Further Evaluation of Soluble CD4 as an Anti–HIV Type 1 Gene Therapy: Demonstration of Protection of Primary Human Peripheral Blood Lymphocytes from Infection by HIV Type 1," *AIDS Research and Human Retroviruses*, 10(11), 1507–1515 (1994).

Ness. *Clin. Chem.*, 46, 1270–1276 (2000).

Ngo et al., "Computational Complexity, Protein Structure Prediction, and the Levinthal Paradox," *The Protein Folding Problem and Tertiary Structure Prediction*, Merz et al., eds., Birkhauser, Boston, 492–495 (1994).

Nicholl, in *An Introduction to Genetic Engineering*, Cambridge University Press: Cambridge, 1994, pp. 1–6 and 127–130.

Okino et al., "Microginin, An Angiotensin–Converting Enzyme Inhibitor from the Blue–Green Alga *Microcystis aeruginosa,*" *Tetrahedron Letters*, 34(3), 501–504 (1993).

Old et al., in *Principles of Gene Manipulation*, Blackwell Scientific Publishers: London, 1992, pp. 1–13 and 108–221.

Orkin et al., *Report and Recommendations of the Panel to Assess the NIH Investment in Research on Gene Therapy* (1995).

Orloff et al., "Increase in Sensitivity to Soluble CD4 by Primary HIV Type 1 Isolates After Passage through C8166 Cells: Association with Sequence Differences in the First Constant (C1) Region of Glycoprotein 120,"*AIDS Research and Human Retroviruses*, 11(3), 335–342 (1995).

Painter, "Developing Women–Friendly AIDS Protection Will Take Time," *USA Today*, (Feb. 13, 1996).

Patterson et al., "Antiviral Activity of Cultured Blue–Green Algae (Cyanophyta)," *J. Phycol.*, 29, 125–130 (1993).

Patterson et al., "Antineoplastic Activity of Cultured Blue–Green Algae (Cyanophyta),"*J. Phycol.*, 27, 530–536 (1991).

Patton et al., "(D) Routes of Delivery: Case Studies (2) Pulmonary delivery of Peptides and Proteins for Systemic Action," *Advanced Drug Delivery Reviews*, 8, 179–196 (1992).

Pelletier et al., "Separation of Diterpenoid Alkaloid Mixtures Using Vacuum Liquid Chromatography," *Journal of Natural Products*, 49(5), 892–900 (1986).

Perelson et al., "HIV–1 Dynamics in Vivo: Virion Clearance Rate, Infected Cell Life–Span, and Viral Generation Time," *Science*, 271, 1582–1586 (1996).

Poskitt et al., "Internal Image (AB2β) Anti–Idiotype Vaccines," Theoretical and Practical Aspects, *Vaccine*, 9, 792–796 (1991).

Powderly et al., *JAMA* 280(1), 72–77 (1998).

Polsky et al., "Inactivation of Human Immunodeficiency Virus In Vitro by Gossypol," *Contraception*, 39(6), 579–587 (1989).

Ramachandran et al., "Failure of Short–Term CD4–PE40 Infusions to Reduce Virus Load in Human Immunodeficiency Virus–Infected Persons," *Journal of Infectious Diseases*, 170, 1009–1013 (1994).

Redondo–Lopez et al., "Emerging Role of *Lactobacilli* in the Control and Maintenance of the Vaginal Bacterial Microflora," *Reviews of Infectious Diseases*, 12(5), 856–872 (1990).

Reid et al., "Is There a Role for *Lactobacilli* in Prevention of Urogenital and Intestinal Infections?," *Clinical Microbiology Reviews*, 3(4), 335–344 (1990).

Rink et al., "Cytoplasmic pH and Free $Mg^{2+}$ in Lymphocytes," *Journal of Cell Biology*, 95, 189–196 (1982).

Rogers, "Ferredoxins, Flavodoxins and Related Proteins: Structure, Function and Evolution," *The Cyanobacteria*, P. Fay et al., eds., Elsevier Science Publishers B.V. (Biomedical Division), 1987, pp. 35–67.

Royer et al., "Inhibition of Human Immunodeficiency Virus Type 1 Replication by Derivatives of Gossypol," *Pharmacol. Res.*, 24(4), 407–412 (1991).

Rosenberg et al., "Commentary: Methods Women Can Use That May Prevent Sexually Transmitted Disease, Including HIV," *American Journal of Public Health*, 82(11), 1473–1478 (1992).

Rosenberg et al., "Virucides in Prevention of HIV Infection," *Sexually Transmitted Diseases*, 20(1), 41–44 (1993).

Rümbeli et al., "□–N–Methylasparagine in Phycobiliproteins from the Cyanobacteria *Mastigocladus laminosus* and *Calothrix*," *FEBS Letters*, 221(1), 1–2 (1987).

Samenen et al., "Polypeptides As Drugs," *in Polymeric Materials in Medication*, Gebelein et al., eds., Plenum Press: New York, 1985, pp. 227–247.

Sanders, "Drug Delivery Systems and Routes of Administration of Peptide and Protein Drugs," *Eur. J. Drug Metab. Pharmacokinet.*, 15(2), 95–102 (1990).

Sattentau et al., "The Human and Simian Immunodeficiency Viruses HIV–1, HIV–2 and SIV Interact with Similar Epitopes on Their Cellular Receptor, the CD4 Molecule," *AIDS*, 2(2), 101–105 (1988).

Schooley et al., "Recombinant Soluble CD4 Therapy in Patients with the Acquired Immunodeficiency Syndrome (AIDS) and AIDS–Related Complex," *Annals of Internal Medicine*, 112(4), 247–253 (1990).

Schrager et al., *JAMA* 280(1), 67–71 (1998).

Schulz et al., *Principles of Protein Structure*, Springer–Verlag, New York, 14–16 (1979).

Sherman et al., "The Protein Composition of the Photosynthetic Complexes from the Cyanobacterial Thylakoid Membrane," *The Cyanobacteria*, P. Fay et al., eds., Elsevier Science Publishers B.V. (Biomedical Division), 1987, pp. 1–33.

Shih et al., "Chimeric Human Immunodeficiency Virus Type 1/Type 2 Reverse Transcriptases Display Reversed Sensitivity to Nonnucleoside Analog Inhibitors," *Proc. Natl. Acad. Sci. USA*, 88, 9878–9882 (1991).

Siddiqui et al., "Nonparenteral Administration of Peptide and Protein Drugs," *CRC Crit. Rev. Therapeutic Drug Carrier Systems*, 3(3), 195–208 (1987).

Sivonen et al., "Three New Microcystins, Cyclic Heptapeptide Hepatotoxins, from Nostoc sp. Strain 152," *Chem. Res. Toxicol.*, 5, 464–469 (1992).

Sofer, *in Introduction to Genetic Engineering*, Butterworth–Heinemann: Stoneham, MA, 1991, pp. 1–21 and 103–126.

Suter et al., "Amino Acid Sequences of □–Allophycocyanin B from *Synechococcus* 6301 and *Mastigocladus laminosus*," *FEBS Letters*, 217(2), 279–282 (1987).

Swanson et al., "Characterization of Phycocyanin Produced by cpcE and cpcF Mutants and Identification of an Intergenic Suppressor of the Defect in Bilin Attachment," *Journal of Biological Chemistry*, 267(23), 16146–16154 (1992).

Taylor, "Building A Chemical Barrier to HIV–1 Transmission," *The Journal of NIH Research*, 6, 26–27 (1994).

Thei et al., "Iontophoresis—Is There a Future for Clinical Application?," *Meth. Find. Exp. Clin. Pharmacol., 13*(5), 353–359 (1991).

Till et al., "HIV–Infected Cells Are Killed by rCD4–Ricin A Chain," *Science, 242*, 1166–1168 (1988).

Traunecker et al., "Highly efficient Neutralization of HIV with Recombinant CD4–Immunoglobulin Molecules," *Nature, 339*, 68–70 (1989).

Tuomala, *Obsterics and Gynecology Clinics of North America, 24*(4), 785–795 (1997).

van Hoogdalem et al., "Intestinal Drug Absorption Enhancement—An Overview," *Pharmac. Ther., 44*, 407–443 (1989).

Vaughan et al., "Human Antibodies by Design," *Nature Biotechnology, 16*, 535–539 (1998).

Verhoef et al., "Transport of Peptide and Protein Drugs Across Biological Membranes," *Eur. J. Drug Metab. Phartmacokinet., 15*(2), 83–93 (1990).

Wallace et al., "Stand and Deliver: Getting Peptide Drugs Into the Body," *Science, 260*, 912–913 (1993).

Walker, "NIAID Expands Research on Topical Microbicides to Prevent STDs in Women," *NIAID News*(Press Release), (Apr. 27, 1995).

Wagner et al., "Immunological Responses to the Tumor–Associated Antigen CA125 in Patients with Advanced Ovarian Cancer Induced by the Murine Monoclonal Anti–Idiotype Vaccine ACA125," *Hybridoma, 16*, 33–40 (1997).

*Webster' Ninth New Collegiate Dictionary*, Merriam–Webster Inc., Springfield, 622, 933, 944 (1991).

Wells, "Additivity of Mutational Effects in Proteins," *Biochemistry, 29*, 8509–8517 (1990).

Weislow et al., "New Soluble–Formazan Assay for HIV–1 Cytopathic Effects: Application to High–Flux Screening of Synthetic and Natural Products for AIDS–Antiviral Activity," *Journal of the National Cancer Institute, 81*(8), 577–586 (1989).

White et al., "A TIBO Derivative, R82913, Is a Potent Inhibitor of HIV–1 Reverse Transcriptase with Heteropolymer Templates," *Antiviral Research, 16*, 257–266 (1991).

Wileman et al., "Soluble Asparaginase–Dextran Conjugates Show Increased Circulatory Persistence and Lowered Antigen Reactivity,"*J. Pharm. Pharmacol., 38*, 264–271 (1986).

Wunsch, E., "Peptide Factors as Pharmaceuticals: Criteria for Application," *Biopolymers, 22*, 493–505 (1983).

\* cited by examiner

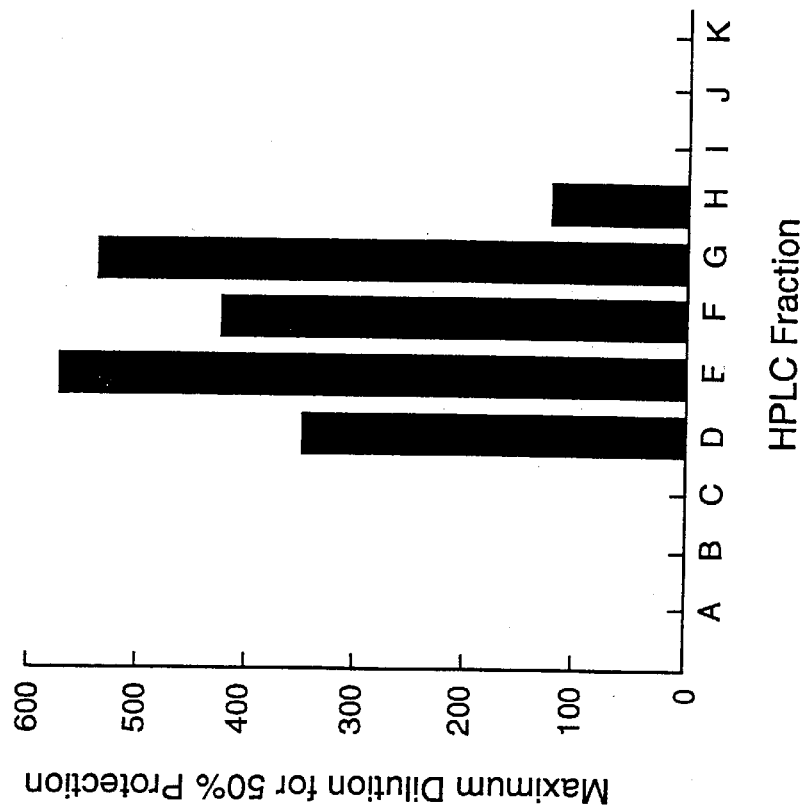
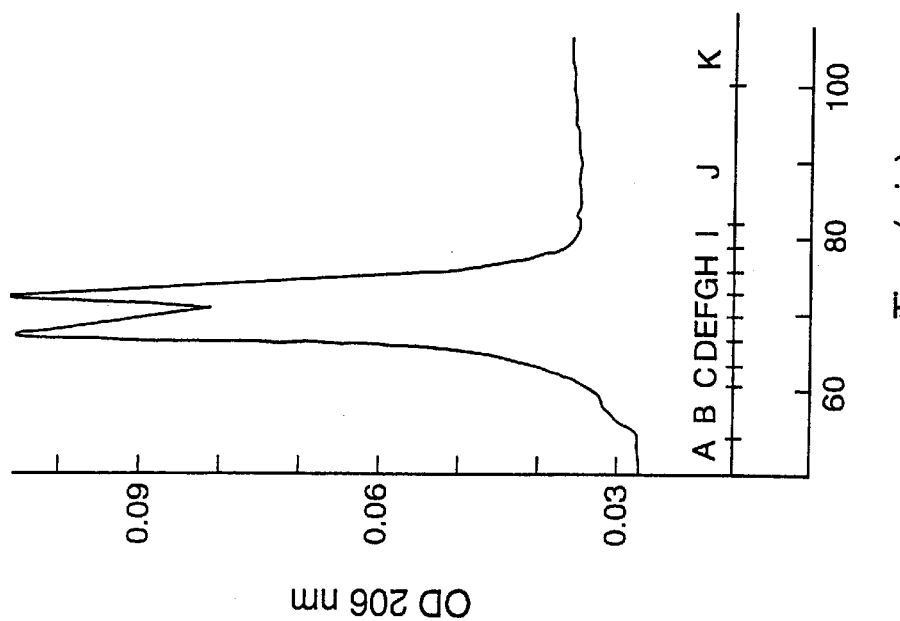
FIG. 1B
FIG. 1A

FLAG Octapeptide

Asp Tyr Lys Asp Asp Asp Lys Leu Gly Lys Phe Ser Gln Thr Cys Tyr Asn Ser Ala

```
                 Hind III
       5'-CGA TCG AAG CTT GGT AAA TTC TCC CAG ACC TGC TAC AAC TCC GCT
       3'-GCT AGC TTC GAA CCA TTT AAG AGG GTC TGG ACG ATG TTG AGG CGA
```

Ile Gln Gly Ser Val Leu Thr Ser Thr Cys Glu Arg Thr Asn Gly Gly Tyr Asn Thr Ser

```
ATC CAG GGT TCC GTT CTG ACC TCC ACC TGC GAA CGT ACC AAC GGT GGT TAC AAC ACC TCC
TAG GTC CCA AGG CAA GAC TGG AGG TGG ACG CTT GCA TGG TTG CCA ATG TTG TGG AGG
```

Ser Ile Asp Leu Asn Ser Val Ile Glu Asn Val Asp Gly Ser Leu Lys Trp Gln Pro Ser

```
TCC ATC GAC CTG AAC TCC GTT ATC GAA AAC GTT GAC GGT TCC CTG AAA TGG CAG CCG TCC
AGG TAG CTG GAC TTG AGG CAA TAG CTT TTG CAA CTG CCA AGG GAC TTT ACC GTC GGC AGG
```

Asn Phe Ile Glu Thr Cys Arg Asn Thr Gln Leu Ala Gly Ser Ser Glu Leu Ala Ala Glu

```
                                                   Bst XI
AAC TTC ATC GAA ACC TGC CGT AAC ACC CAG CTG GCT GGT TCC TCC GAA CTG GCT GCT GAA
TTG AAG TAG CTT TGG ACG GCA TTG TGG GTC GAC CGA CCA AGG AGG CTT GAC CGA CGA CTT
```

Cys Lys Thr Arg Ala Gln Phe Val Ser Thr Lys Ile Asn Leu Asp Asp His Ile Ala

```
          Esp I
TGC AAA ACC CGT GCT CAG CAG TTC GTT TCC ACC AAA ATC AAC CTG GAC GAC CAC ATC GCT
ACG TTT TGG GCA CGA GTC GTC AAG CAA AGG TGG TTT TAG TTG GAC CTG CTG GTG TAG CGA
```

Asn Ile Asp Gly Thr Leu Lys Tyr Glu

```
                                          Xho I
AAC ATC GAC GGT ACC CTG AAA TAC GAA TAA CTC GAG ATC GTA-3'
TTG TAG CTG CCA TGG GAC TTT ATG CTT ATT GAG CTC TAG CAT-5'
```

FIG. 2

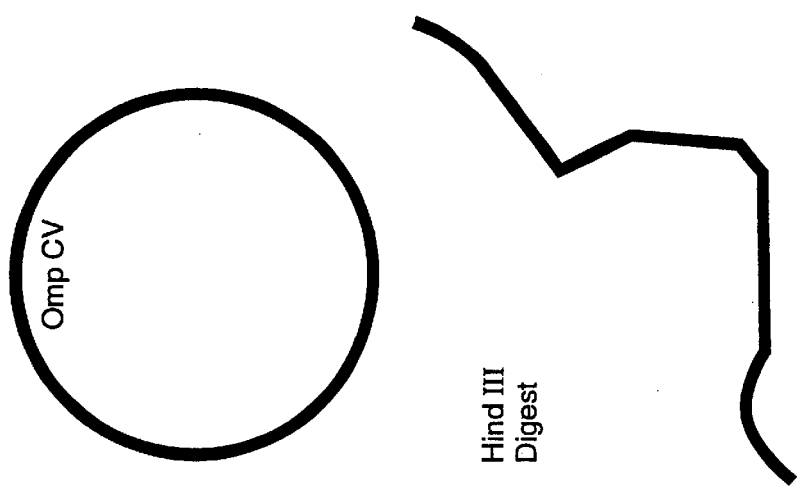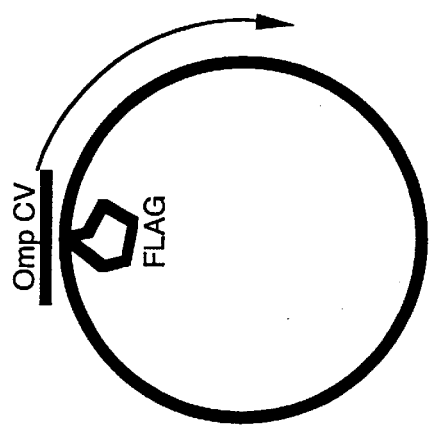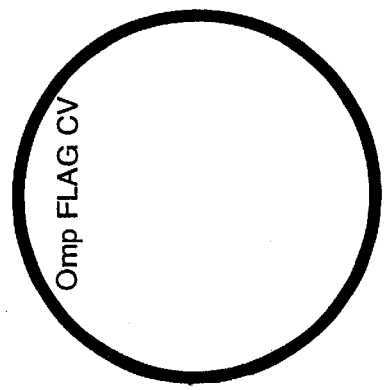
FIG. 3

FIG. 8

SEQUENCE LISTING

<160> NUMBER OF SEQ ID NOS: 4

<210> SEQ ID NO 1
<211> LENGTH: 327
<212> TYPE: DNA
<213> ORGANISM: Nostoc ellipsosporum
<220> FEATURE:
<221> NAME/KEY: CDS
<222> LOCATION: (10)..(312)
<223> OTHER INFORMATION:

<400> SEQUENCE: 1

```
cgatcgaag ctt ggt aaa ttc tcc cag acc tgc tac aac tcc gct atc cag      51
          Leu Gly Lys Phe Ser Gln Thr Cys Tyr Asn Ser Ala Ile Gln
          1               5                   10 ggt tcc gtt ctg acc tcc acc tgc gaa cgt acc aac ggt ggt tac aac        99
Gly Ser Val Leu Thr Ser Thr Cys Glu Arg Thr Asn Gly Gly Tyr Asn
15                  20                  25                  30 acc tcc tcc atc gac ctg aac tcc gtt atc gaa aac gtt gac ggt tcc       147
Thr Ser Ser Ile Asp Leu Asn Ser Val Ile Glu Asn Val Asp Gly Ser
                35                  40                  45 ctg aaa tgg cag ccg tcc aac ttc atc gaa acc tgc cgt aac acc cag       195
Leu Lys Trp Gln Pro Ser Asn Phe Ile Glu Thr Cys Arg Asn Thr Gln
            50                  55                  60 ctg gct ggt tcc tcc gaa ctg gct gct gaa tgc aaa acc cgt gct cag       243
Leu Ala Gly Ser Ser Glu Leu Ala Ala Glu Cys Lys Thr Arg Ala Gln
65                  70                  75 cag ttc gtt tcc acc aaa atc aac ctg gac gac cac atc gct aac atc       291
Gln Phe Val Ser Thr Lys Ile Asn Leu Asp Asp His Ile Ala Asn Ile
80                  85                  90 gac ggt acc ctg aaa tac gaa taactcgaga tcgta                          327
Asp Gly Thr Leu Lys Tyr Glu
95                  100
```

<210> SEQ ID NO 2
<211> LENGTH: 101
<212> TYPE: PRT
<213> ORGANISM: Nostoc ellipsosporum

<400> SEQUENCE: 2

```
Leu Gly Lys Phe Ser Gln Thr Cys Tyr Asn Ser Ala Ile Gln Gly Ser
1               5                   10                  15

Val Leu Thr Ser Thr Cys Glu Arg Thr Asn Gly Gly Tyr Asn Thr Ser
            20                  25                  30

Ser Ile Asp Leu Asn Ser Val Ile Glu Asn Val Asp Gly Ser Leu Lys
        35                  40                  45

Trp Gln Pro Ser Asn Phe Ile Glu Thr Cys Arg Asn Thr Gln Leu Ala
    50                  55                  60

Gly Ser Ser Glu Leu Ala Ala Glu Cys Lys Thr Arg Ala Gln Gln Phe
65                  70                  75                  80

Val Ser Thr Lys Ile Asn Leu Asp Asp His Ile Ala Asn Ile Asp Gly
                85                  90                  95

Thr Leu Lys Tyr Glu
            100
```

```
<210> SEQ ID NO 3
<211> LENGTH: 327
<212> TYPE: DNA
<213> ORGANISM: Nostoc ellipsosporum
<220> FEATURE:
<221> NAME/KEY: CDS
<222> LOCATION: (1)..(327)
<223> OTHER INFORMATION:

<400> SEQUENCE: 3 gac tac aag gac gac gat gac aag ctt ggt aaa ttc tcc cag acc tgc        48
Asp Tyr Lys Asp Asp Asp Asp Lys Leu Gly Lys Phe Ser Gln Thr Cys
1               5                   10                  15 tac aac tcc gct atc cag ggt tcc gtt ctg acc tcc acc tgc gaa cgt        96
Tyr Asn Ser Ala Ile Gln Gly Ser Val Leu Thr Ser Thr Cys Glu Arg
                20                  25                  30 acc aac ggt ggt tac aac acc tcc tcc atc gac ctg aac tcc gtt atc       144
Thr Asn Gly Gly Tyr Asn Thr Ser Ser Ile Asp Leu Asn Ser Val Ile
            35                  40                  45 gaa aac gtt gac ggt tcc ctg aaa tgg cag ccg tcc aac ttc atc gaa       192
Glu Asn Val Asp Gly Ser Leu Lys Trp Gln Pro Ser Asn Phe Ile Glu
        50                  55                  60 acc tgc cgt aac acc cag ctg gct ggt tcc tcc gaa ctg gct gct gaa       240
Thr Cys Arg Asn Thr Gln Leu Ala Gly Ser Ser Glu Leu Ala Ala Glu
65                  70                  75                  80 tgc aaa acc cgt gct cag cag ttc gtt tcc acc aaa atc aac ctg gac       288
Cys Lys Thr Arg Ala Gln Gln Phe Val Ser Thr Lys Ile Asn Leu Asp
                85                  90                  95 gac cac atc gct aac atc gac ggt acc ctg aaa tac gaa                   327
Asp His Ile Ala Asn Ile Asp Gly Thr Leu Lys Tyr Glu
            100                 105

<210> SEQ ID NO 4
<211> LENGTH: 109
<212> TYPE: PRT
<213> ORGANISM: Nostoc ellipsosporum

<400> SEQUENCE: 4

Asp Tyr Lys Asp Asp Asp Asp Lys Leu Gly Lys Phe Ser Gln Thr Cys
1               5                   10                  15

Tyr Asn Ser Ala Ile Gln Gly Ser Val Leu Thr Ser Thr Cys Glu Arg
                20                  25                  30

Thr Asn Gly Gly Tyr Asn Thr Ser Ser Ile Asp Leu Asn Ser Val Ile
            35                  40                  45

Glu Asn Val Asp Gly Ser Leu Lys Trp Gln Pro Ser Asn Phe Ile Glu
        50                  55                  60

Thr Cys Arg Asn Thr Gln Leu Ala Gly Ser Ser Glu Leu Ala Ala Glu
65                  70                  75                  80

Cys Lys Thr Arg Ala Gln Gln Phe Val Ser Thr Lys Ile Asn Leu Asp
                85                  90                  95

Asp His Ile Ala Asn Ile Asp Gly Thr Leu Lys Tyr Glu
            100                 105
```

GLYCOSYLATION-RESISTANT CYANOVIRINS AND RELATED CONJUGATES, COMPOSITIONS, NUCLEIC ACIDS, VECTORS, HOST CELLS, METHODS OF PRODUCTION AND METHODS OF USING NONGLYCOSYLATED CYANOVIRINS

CROSS-REFERENCE TO RELATED PATENT APPLICATIONS

This application is a continuation-in-part of patent application Ser. No. 09/416,434 (the '434 application), now U.S. Pat. No. 6,428,796, which was filed on Oct. 12, 1999, as a continuation-in-part of patent application Ser. No. 09/267,447, now abandoned, which was filed on Mar. 12, 1999, now ABN as a continuation-in-part of patent application Ser. No. 08/969,378, filed on Nov. 13, 1997, and issued as U.S. Pat. No. 6,015,876, which is a divisional of patent application Ser. No. 08/429,965, which was filed on Apr. 27, 1995, and has since issued as U.S. Pat. No. 5,843,882. The '434 application is also a continuation-in-part of patent application Ser. No. 08/969,689, which was filed on Nov. 13, 1997, as a divisional of application Ser. No. 08/638,610, filed on Apr. 26, 1996, and issued as U.S. Pat. No. 5,821,081, which is a continuation-in-part of Ser. No. 08/429,965, filed on Apr. 27, 1995 which as indicated above, is now U.S. Pat. No. 5,843,882.

TECHNICAL FIELD OF THE INVENTION

The present invention relates to the use of cyanovirins to inhibit prophylactically or therapeutically influenza viral infection, as well as glycosylation-resistant cyanovirins and related conjugates, compositions, nucleic acids, vectors, host cells and methods of production and use.

BACKGROUND OF THE INVENTION

The field of viral therapeutics has developed in response to the need for agents effective against retroviruses, especially HIV. There are many ways in which an agent can exhibit anti-retroviral activity (e.g., see DeClercq, *Adv. Virus Res.* 42, 1–55, 1993; DeClercq, *J. Acquir. Imun. Def. Synd.* 4, 207–218, 1991; and Mitsuya et al., *Science* 249, 1533–1544, 1990). Nucleoside derivatives, such as AZT, which inhibit the viral reverse transcriptase, were among the first clinically active agents available commercially for anti-HIV therapy. Although very useful in some patients, the utility of AZT and related compounds is limited by toxicity and insufficient therapeutic indices for fully adequate therapy. Also, given the subsequent revelations about the true dynamics of HIV infection (Coffin, *Science* 267, 483–489, 1995; and Cohen, *Science* 267, 179, 1995), it has become increasingly apparent that agents acting as early as possible in the viral replicative cycle are needed to inhibit infection of newly produced, uninfected immune cells generated in the body in response to the virus-induced killing of infected cells. Also, it is essential to neutralize or inhibit new infectious virus produced by infected cells.

Infection of people by influenza viruses is also a major cause of pandemic illness, morbidity and mortality worldwide. The adverse economic consequences, as well as human suffering, are enormous. Available treatments for established infection by this virus are either minimally effective or ineffective; these treatments employ amantatadine, rimantadine and neuraminidase inhibitors. Of these drugs, only the neuraminidase inhibitors are substantially active against multiple strains of influenza virus that commonly infect humans, yet these drugs still have limited utility or efficacy against pandemic disease.

Currently, the only effective preventative treatment against influenza viral infection is vaccination. However, this, like the drug treatments, is severely limited by the propensity of influenza viruses to mutate rapidly by genetic exchange, resulting in the emergence of highly resistant viral strains that rapidly infect and spread throughout susceptible populations. In fact, a vaccination strategy is only effective from year-to-year if the potential pandemic strains can be identified or predicted, and corresponding vaccines prepared and administered early enough that the year's potential pandemic can be aborted or attenuated. Thus, new preventative and therapeutic interventions and agents are urgently needed to combat influenza viruses.

New agents with broad anti-influenza virus activity against diverse strains, clinical isolates and subtypes of influenza virus would be highly useful, since such agents would most likely remain active against the mutating virus. The two major types of influenza virus that infect humans are influenza A and B, both of which cause severe acute illness that may include both respiratory and gastrointestinal distress, as well as other serious pathological sequellae. An agent that has anti-influenza virus activity against diverse strains and isolates of both influenza A and B, including recent clinical isolates thereof, would be particularly advantageous for use in prevention or treatment of hosts susceptible to influenza virus infection.

The predominant mode of transmission of influenza viral infection is respiratory, i.e., transmission via inhalation of virus-laden aerosolized particles generated through coughing, sneezing, breathing, etc., of an influenza-infected individual. Transmission of infectious influenza virions may also occur through contact (e.g., through inadvertent hand-to-mouth contact, kissing, touching, etc.) with saliva or other bodily secretions of an infected individual. Thus, the primary first points of contact of infectious influenza virions within a susceptible individual are the mucosal surfaces within the oropharyngeal mucosa, and the mucosal surfaces within the upper and lower respiratory tracts. Not only do these sites comprise first points of virus contact for initial infection of an individual, they are also the primary sites for production and exit (e.g., by coughing, sneezing, salivary transmission, etc.) of bodily fluids containing infectious influenza viral particles. Therefore, availability of a highly potent anti-influenza virus agent, having broad-spectrum activity against diverse strains and isolates of influenza viruses A and B, which could be applied or delivered topically to the aforementioned mucosal sites of contact and infection and transmission of infectious influenza viruses, would be highly advantageous for therapeutic and preventative inhibition of influenza viral infection, either in susceptible uninfected or infected hosts.

In this regard, new classes of antiviral agents, to be used alone or in combination existing antiviral agents, are needed for effective antiviral therapy. New agents are also important for the prophylactic inhibition of viral infection. In both areas of need, the ideal new agent(s) would act as early as possible in the viral life cycle; be as virus-specific as possible (i.e., attack a molecular target specific to the virus but not the host); render the intact virus noninfectious; prevent the death or dysfunction of virus-infected cells; prevent further production of virus from infected cells; prevent spread of virus infection to uninfected cells; be highly potent and active against the broadest possible range of strains and isolates of a given virus; be resistant to degradation under physiological and rigorous environmental conditions; and be readily and inexpensively produced.

Accordingly, it is an object of the present invention to provide a method of inhibiting prophylactically or therapeutically a viral infection, specifically an influenza viral infection, of a host. It is another object of the present invention to provide glycosylation-resistant cyanovirins and related conjugates, nucleic acids, vectors, host cells and methods of production and use. These and other objects and advantages of the present invention, as well as additional inventive features, will become apparent from the description provided herein.

BRIEF SUMMARY OF THE INVENTION

The present invention provides, among other things, an isolated and purified nucleic acid molecule that encodes a protein or peptide comprising at least nine contiguous amino acids of SEQ ID NO:2, wherein the at least nine contiguous amino acids comprise amino acids 30–32 of SEQ ID NO: 2 which have been rendered glycosylation resistant and wherein the at least nine contiguous amino acids have antiviral activity. Further provided is a vector comprising such an isolated and purified nucleic acid molecule and a host cell or organism comprising the vector.

Accordingly, the present invention also provides a method of producing an antiviral protein or antiviral peptide, which method comprises expressing the vector in a host cell or organism. Thus, an antiviral protein or antiviral peptide comprising at least nine contiguous amino acids of SEQ ID NO:2, wherein the at least nine contiguous amino acids comprise amino acids 30–32 of SEQ ID NO: 2 which have been rendered glycosylation resistant and wherein the at least nine contiguous amino acids have antiviral activity, is also provided as is a conjugate comprising the antiviral protein or antiviral peptide and at least one effector component selected from the group consisting of polyethylene glycol, albumin, dextran, a toxin and an immunological reagent. Compositions comprising an effective amount of the antiviral protein, antiviral peptide, antiviral protein conjugate or antiviral peptide conjugate are also provided.

The present invention further provides a method of inhibiting prophylactically or therapeutically a viral infection, specifically an influenza viral infection, of a host. The method comprises administering to the host an effective amount of an antiviral protein, antiviral peptide, antiviral protein conjugate or antiviral peptide conjugate comprising at least nine contiguous amino acids of SEQ ID NO:2, wherein the at least nine contiguous amino acids are nonglycosylated and have antiviral activity, whereupon the viral infection is inhibited.

BRIEF DESCRIPTION OF THE DRAWINGS

FIG. 1A is a graph of OD (206 mn) versus time (min), which represents an HPLC chromatogram of nonreduced cyanovirin.

FIG. 1B is a bar graph of maximum dilution for 50% protection versus HPLC fraction, which illustrates the maximum dilution of each HPLC fraction that provided 50% protection from the cytopathic effects of HIV infection for the nonreduced cyanovirin HPLC fractions.

FIG. 2 shows an example of a DNA sequence encoding a synthetic cyanovirin gene (SEQ ID NOS: 1–4).

FIG. 3 illustrates a site-directed mutagenesis maneuver used to eliminate codons for a FLAG octapeptide and a Hind III restriction site from the sequence of FIG. 2.

FIG. 8 is a graph of OD (450 mn) versus cyanovirin concentration ($\mu$g/ml), which illustrates cyanovirin/gp120 interactions defining gp120 as a principal molecular target of cyanovirin.

DETAILED DESCRIPTION OF THE PRESENT INVENTION

Figure 1D:
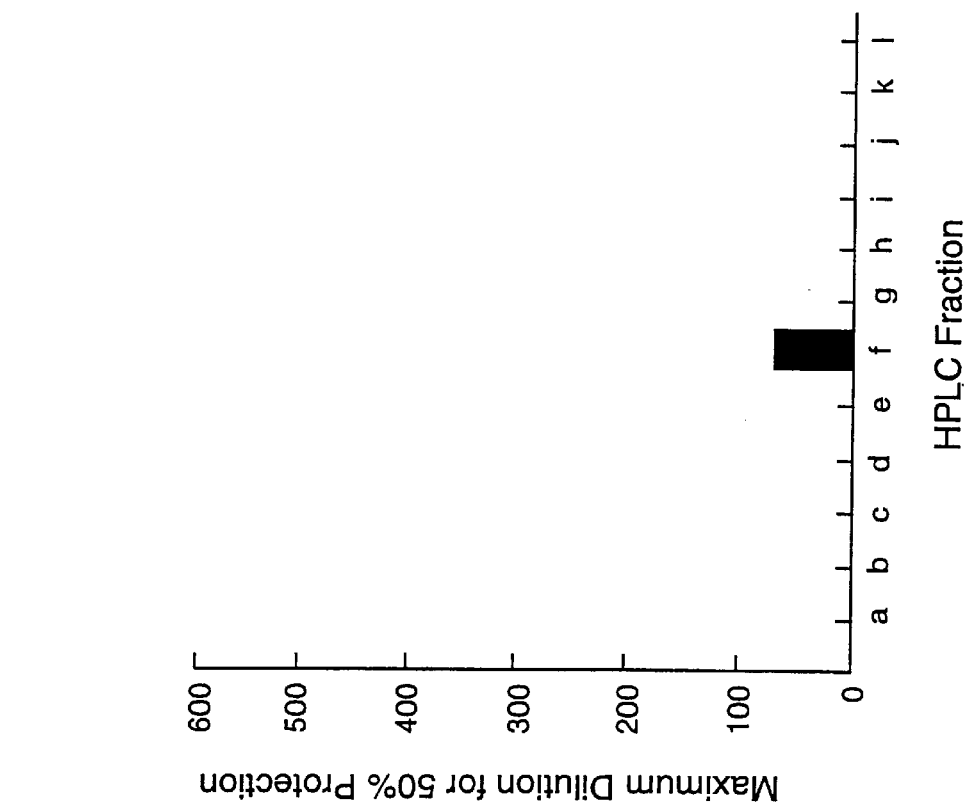
FIG. 1D is a bar graph of maximum dilution for 50% protection versus HPLC dilution, which illustrates the maximum dilution of each fraction that provided 50% protection from the cytopathic effects of HIV infection for the reduced cyanovirin HPLC fractions.

The principal overall objective of the present invention is to provide anti-viral proteins, peptides and derivatives thereof, and broad medical uses thereof, including prophylactic and/or therapeutic applications against viruses. An initial observation, which led to the present invention, was antiviral activity in certain extracts from cultured cyanobacteria (blue-green algae) tested in an anti-HIV screen. The screen is one that was conceived in 1986 (by M. R. Boyd of the National Institutes of Health) and has been developed and operated at the U.S. National Cancer Institute (NCI) since 1988 (see Boyd, in *AIDS, Etiology, Diagnosis, Treatment and Prevention*, DeVita et al., eds., Philadelphia: Lippincott, 1988, pp. 305–317).

Cyanobacteria (blue-green algae) were specifically chosen for anti-HIV screening because they had been known to produce a wide variety of structurally unique and biologically active non-nitrogenous and amino acid-derived natural products (Faulkner, *Nat. Prod. Rep.* 11, 355–394, 1994; and Glombitza et al., in *Algal and Cyanobacterial Biotechnology,* Cresswell, R. C., et al. eds., 1989, pp. 211–218). These photosynthetic procaryotic organisms are significant producers of cyclic and linear peptides (molecular weight generally <3 kDa), which often exhibit hepatotoxic or antimicrobial properties (Okino et al., *Tetrahedron Lett.* 34, 501–504, 1993; Krishnamurthy et al., *PNAS USA* 86, 770–774, 1989; Sivonen et al., *Chem. Res. Toxicol.* 5, 464–469, 1992; Carter et al., *J. Org. Chem.* 49, 236–241, 1984; and Frankmolle et al., *J. Antibiot.* 45, 1451–1457, 1992). Sequencing studies of higher molecular weight cyanobacterial peptides and proteins have generally focused on those associated with primary metabolic processes or ones that can serve as phylogenetic markers (Suter et al., *FEBS Lett.* 217, 279–282, 1987; Rumbeli et al., *FEBS Lett.* 221, 1–2, 1987; Swanson et al., *J. Biol. Chem.* 267, 16146–16154, 1992; Michalowski et al., *Nucleic Acids Res.* 18, 2186, 1990; Sherman et al., in *The Cyanobacteria,* Fay et al., eds., Elsevier: New York, 1987, pp. 1–33; and Rogers, in *The Cyanobacteria,* Fay et al., eds., Elsevier: New York, 1987, pp. 35–67). In general, proteins with antiviral properties had not been associated with cyanobacterial sources.

The cyanobacterial extract leading to the present invention was among many thousands of different extracts initially selected randomly and tested blindly in the anti-HIV screen described above. A number of these extracts had been determined preliminarily to show anti-HIV activity in the NCI screen (Patterson et al., *J. Phycol.* 29, 125–130, 1993). From this group, an aqueous extract from *Nostoc ellipsosporum,* which had been prepared as described (Patterson, 1993, supra) and which showed an unusually high anti-HIV potency and in vitro "therapeutic index" in the NCI primary screen, was selected for detailed investigation. A specific bioassay-guided strategy was used to isolate and purify a homogenous protein highly active against HIV.

In the bioassay-guided strategy, initial selection of the extract for fractionation, as well as the decisions concerning the overall chemical isolation method to be applied, and the nature of the individual steps therein, is determined by interpretation of biological testing data. The anti-HIV screening assay (e.g., see Boyd, 1988, supra; Weislow et al., *J. Natl. Cancer Inst.* 81, 577–586, 1989), which is used to guide the isolation and purification process, measures the degree of protection of human T-lymphoblastoid cells from the cytopathic effects of HIV. Fractions of the extract of interest are prepared using a variety of chemical means and are tested blindly in the primary screen. Active fractions are separated further, and the resulting subfractions are likewise tested blindly in the screen. This process is repeated as many times as necessary in order to obtain the active compound(s), i.e., antiviral fraction(s) representing pure compound(s), which then can be subjected to detailed chemical analysis and structural elucidation.

Using this strategy, aqueous extracts of *Nostoc ellipsosporum* were shown to contain an antiviral protein. Accordingly, the present invention provides an isolated and purified antiviral protein, named cyanovirin-N, from *Nostoc ellipsosporum* and functional homologs thereof, called "cyanovirins." Herein the term "cyanovirin" is used generically to refer to a native cyanovirin or any related, functionally equivalent (i.e., antiviral) protein, peptide or derivative thereof. By definition, in this context, a related, functionally equivalent protein, peptide or derivative thereof a) contains a sequence of at least nine amino acids directly homologous with any sub-sequence of nine contiguous amino acids contained within a native cyanovirin, and, b) is capable of specifically binding to a virus, in particular an influenza virus or a retrovirus, more specifically a primate immunodeficiency virus, more specifically HIV-1, HIV-2 or SIV, or to an infected host cell expressing one or more viral antigen(s), more specifically an envelope glycoprotein, such as gp120, of the respective virus. Herein, the term "protein" refers to a sequence comprising 100 or more amino acids, whereas "peptide" refers to a sequence comprising less than 100 amino acids. In addition, such a functionally equivalent protein or derivative thereof can comprise the amino acid sequence of a native cyanovirin, particularly cyanovirin-N (see SEQ ID NO:2), in which 1–20, preferably 1–10, more preferably 1, 2, 3, 4, or 5, and most preferably 1 or 2, amino acids have been removed from one or both ends, preferably from only one end, and most preferably from the amino-terminal end, of the native cyanovirin. Alternatively, a functionally equivalent protein or derivative thereof can comprise the amino acid sequence of a native cyanovirin, particularly cyanovirin-N (see SEQ ID NO:2), in which 1–20, preferably 1–10, more preferably 1, 2, 3, 4, or 5, and most preferably 1 or 2, amino acids have been added to one or both ends, preferably from only one end, and most preferably from the amino-terminal end, of the native cyanovirin.

Preferably, the protein, peptide or derivative thereof comprises an amino acid sequence that is substantially homologous to that of an antiviral protein from *Nostoc ellipsosporum.* By "substantially homologous" is meant sufficient homology to render the protein, peptide or derivative thereof antiviral, with antiviral activity characteristic of an antiviral protein isolated from *Nostoc ellipsosporum.* At least about 50% homology, preferably at least about 75% homology, and most preferably at least about 90% homology should exist. A cyanovirin conjugate comprises a cyanovirin coupled to one or more selected effector molecule(s), such as a toxin or immunological reagent. "Immunological reagent" will be used to refer to an antibody, an immunoglobulin, and an immunological recognition element. An immunological recognition element is an element, such as a peptide, e.g., the FLAG sequence of the recombinant cyanovirin-FLAG fusion protein, which facilitates, through immunological recognition, isolation and/or purification and/or analysis of the protein or peptide to which it is attached. A cyanovirin fusion protein is a type of cyanovirin conjugate, wherein a cyanovirin is coupled to one or more other protein(s) having any desired properties or effector functions, such as cytotoxic or immunological properties, or other desired properties, such as to facilitate isolation, purification or analysis of the fusion protein.

Accordingly, the present invention provides an isolated and purified protein encoded by a nucleic acid molecule comprising a sequence of SEQ ID NO:1, a nucleic acid molecule comprising a sequence of SEQ ID NO:3, a nucleic acid molecule encoding an amino acid sequence of SEQ ID NO:2, or a nucleic acid molecule encoding an amino acid sequence of SEQ ID NO:4. Preferably, the aforementioned nucleic acid molecules encode at least nine contiguous amino acids of the amino acid sequence of SEQ ID NO:2, which desirably have antiviral activity. If the at least nine contiguous amino acids of SEQ ID NO: 2 comprise amino acids 30–32, desirably amino acids 30–32 have been rendered glycosylation resistant, yet maintain antiviral activity. Preferably, amino acids 30–32 of SEQ ID NO: 2 have been rendered glycosylation resistant by deletion or substitution of amino acid 30. Preferably, amino acid 30 has been substituted with an amino acid selected from the group consisting of alanine, glutamine and valine. Optionally, amino acid 51 can be deleted or substituted, for example, with glycine. Substitution or deletion of the proline at position 51 is expected to enhance the dimerization resistance; dimerization of a cyanovirin is known to occur under certain conditions (Yang et al., *J. Molec. Biol.*, 288, 403–412, 1999; Bewley et al., *JACS*, 122, 6009–6016 (2000)), and folding stability and resistance to physiochemical degradation are desirable additional attributes of the cyanovirins. Such traits are desirable for large-scale isolation and purification and mass production of cyanovirins in prokaryotic and eukaryotic host-cells/organisms.

The present invention also provides a method of obtaining a cyanovirin from *Nostoc ellipsosporum*. Such a method comprises (a) identifying an extract of *Nostoc ellipsosporum* containing antiviral activity, (b) optionally removing high molecular weight biopolymers from the extract, (c) antiviral bioassay-guided fractionating the extract to obtain a crude extract of cyanovirin, and (d) purifying the crude extract by reverse-phase HPLC to obtain cyanovirin (see, also, Example 1). More specifically, the method involves the use of ethanol to remove high molecular weight biopolymers from the extract and the use of an anti-HIV bioassay to guide fractionation of the extract.

Cyanovirin-N (a protein of exactly SEQ ID NO:2), which was isolated and purified using the aforementioned method, was subjected to conventional procedures typically used to determine the amino acid sequence of a given pure protein. Thus, the cyanovirin was initially sequenced by N-terminal Edman degradation of intact protein and numerous overlapping peptide fragments generated by endoproteinase digestion. Amino acid analysis was in agreement with the deduced sequence. ESI mass spectrometry of reduced, HPLC-purified cyanovirin-N showed a molecular ion consistent with the calculated value. These studies indicated that cyanovirin-N from *Nostoc ellipsosporum* was comprised of a unique sequence of 101 amino acids having little or no significant homology to previously described proteins or transcription products of known nucleotide sequences. No more than eight contiguous amino acids from cyanovirin were found in any amino acid sequences from known proteins, nor were there any known proteins from any source containing greater than 13% sequence homology with cyanovirin-N. Given the chemically deduced amino acid sequence of cyanovirin-N, a corresponding recombinant cyanovirin-N (r-cyanovirin-N) was created and used to establish definitively that the deduced amino acid sequence was, indeed, active against virus, such as HIV (Boyd et al., 1995, supra; also, see Examples 2–5).

Accordingly, the present invention provides isolated and purified nucleic acid molecules and synthetic nucleic acid molecules, which comprise a coding sequence for a cyanovirin, such as an isolated and purified nucleic acid molecule comprising a sequence of SEQ ID NO:1, an isolated and purified nucleic acid molecule comprising a sequence of SEQ ID NO:3, an isolated and purified nucleic acid molecule encoding an amino acid sequence of SEQ ID NO:2, an isolated and purified nucleic acid molecule encoding an amino acid sequence of SEQ ID NO:4, and a nucleic acid molecule that is substantially homologous to any one or more of the aforementioned nucleic acid molecules. By "substantially homologous" is meant sufficient homology to render the protein, peptide or derivative thereof antiviral, with antiviral activity characteristic of an antiviral protein isolated from *Nostoc ellipsosporum*. At least about 50% homology, preferably at least about 75% homology, and most preferably at least about 90% homology should exist.

The present inventive nucleic acid molecule preferably comprises a nucleic acid sequence encoding at least nine (preferably at least twenty, more preferably at least thirty, and most preferably at least fifty) contiguous amino acids of the amino acid sequence of SEQ ID NO:2. The present inventive nucleic acid molecule also comprises a nucleic acid sequence encoding a protein comprising the amino acid sequence of a native cyanovirin, particularly cyanovirin-N, in which 1–20, preferably 1–10, more preferably 1, 2, 3, 4, or 5, and most preferably 1 or 2, amino acids have been removed from one or both ends, preferably from only one end, and most preferably from the amino-terminal end, of the native cyanovirin. Alternatively, the nucleic acid molecule can comprise a nucleic acid sequence encoding a protein comprising the amino acid sequence of a native cyanovirin, particularly cyanovirin-N (see SEQ ID NO:2), in which 1–20, preferably 1–10, more preferably 1, 2, 3, 4, or 5, and most preferably 1 or 2, amino acids have been addeded to one or both ends, preferably from only one end, and most preferably from the amino-terminal end, of the native cyanovirin. Preferably, the isolated and purified nucleic acid molecule encodes a protein or peptide comprising at least nine contiguous amino acids of SEQ ID NO:2, which desirably have antiviral activity. If the at least nine contiguous amino acids comprise amino acids 30–32 of SEQ ID NO: 2, desirably amino acids 30–32 have been rendered glycosylation resistant, yet maintain antiviral activity. Preferably, the amino acids 30–32 of SEQ ID NO: 2 have been rendered glycosylation resistant by deletion or substitution of amino acid 30. Preferably, amino acid 30 has been substituted with an amino acid selected from the group consisting of alanine, glutamine and valine. Optionally, amino acid 51 can be deleted or substituted, for example, with glycine. Such deletions and substitutions are within the skill in the art as indicated below.

Given the present disclosure, it will be apparent to one skilled in the art that a partial cyanovirin-N gene sequence will likely suffice to code for a fully functional, i.e., antiviral, such as anti-influenza or anti-HIV, cyanovirin. A minimum essential DNA coding sequence(s) for a functional cyanovirin can readily be determined by one skilled in the art, for example, by synthesis and evaluation of sub-sequences comprising the native cyanovirin, and by site-directed mutagenesis studies of the cyanovirin-N DNA coding sequence.

Using an appropriate DNA coding sequence, a recombinant cyanovirin can be made by genetic engineering techniques (for general background see, e.g., Nicholl, in *An Introduction to Genetic Engineering,* Cambridge University Press: Cambridge, 1994, pp. 1–5 & 127–130; Steinberg et al., in *Recombinant DNA Technology Concepts and Biomedical Applications,* Prentice Hall: Englewood Cliffs, N.J., 1993, pp. 81–124 & 150–162; Sofer in *Introduction to Genetic Engineering,* Butterworth-Heinemann, Stoneham, Mass., 1991, pp. 1–21 & 103–126; Old et al., in *Principles of Gene Manipulation,* Blackwell Scientific Publishers: London, 1992, pp. 1–13 & 108–221; and Emtage, in *Delivery Systems for Peptide Drugs,* Davis et al., eds., Plenum Press: New York, 1986, pp. 23–33). For example, a *Nostoc ellipsosporum* gene or cDNA encoding a cyanovirin can be identified and subcloned. The gene or cDNA can then be incorporated into an appropriate expression vector and delivered into an appropriate protein-synthesizing organism (e.g., *E. coli, S. cerevisiae, P. pastoris,* or other bacterial, yeast, insect, plant or mammalian cells, where the gene, under the control of an endogenous or exogenous promoter, can be appropriately transcribed and translated. Alternatively, the expression vector can be administered to a plant or animal, for example, for large-scale production (see, e.g., Fischer et al., *Transgenic Res.*, 9(4–5), 279–299, 2000; Fischer et al., *J. Biol. Regul. Homeost. Agents*, 14, 83–92, 2000; deWilde et al., *Plant Molec. Biol.*, 43, 347–359, 2000; Houdebine, *Transgenic Research*, 9, 305–320, 2000; Brink et al., *Theriogenology*, 53, 139–148, 2000; Pollock et al., *J. Immunol. Methods*, 231, 147–157, 1999; Conrad et al., *Plant Molec. Biol.*, 38, 101–109, 1998; Staub et al., *Nature Biotech.*, 18, 333–338, 2000; McCormick et al., *PNAS USA*, 96, 703–708, 1999; Zeitlin et al., *Nature Biotech.*, 16, 1361–1364 (1998); Tacker et al., *Microbes and Infection*, 1, 777–783, 1999; and Tacket et al., *Nature Med.*, 4(5), 607–609, 1998). Such expression vectors (including, but not limited to, phage, cosmid, viral, and plasmid vectors) are known to those skilled in the art, as are reagents and techniques appropriate for gene transfer (e.g., transfection, electroporation, transduction, micro-injection, transformation, etc.). Subsequently, the recombinantly produced protein can be isolated and purified using standard techniques known in the art (e.g., chromatography, centrifugation, differential solubility, isoelectric focusing, etc.), and assayed for antiviral activity. If a cyanovirin is to be recombinantly produced in isolated eukaryotic cells or in a eukaryotic organism, such as a plant (see above references and also *Methods in Biotechnology, Recombinant Proteins from Plants, Production and Isolation of Clinically Useful Compounds*, Cunningham and Porter, editors, Humana Press: Totowa, N.J. 1998), desirably the N-linked glycosylation site at position 30 (Asn30-Thr31-Ser32) is rendered glycosylation-resistant, such as in accordance with the methods described herein. Optionally, amino acid 51 is deleted or substituted, for example, with glycine.

Alternatively, a native cyanovirin can be obtained from *Nostoc ellipsosporum* by non-recombinant methods (e.g., see Example 1 and above), and sequenced by conventional techniques. The sequence can then be used to synthesize the corresponding DNA, which can be subcloned into an appropriate expression vector and delivered into a protein-producing cell for en mass recombinant production of the desired protein.

In this regard, the present invention also provides a vector comprising a DNA sequence, e.g., a *Nostoc ellipsosporum* gene sequence for cyanovirin, a cDNA encoding a cyanovirin, or a synthetic DNA sequence encoding cyanovirin, a host cell comprising the vector, and a method of using such a host cell to produce a cyanovirin.

The DNA, whether isolated and purified or synthetic, or cDNA encoding a cyanovirin can encode for either the entire cyanovirin or a portion thereof. Where the DNA or cDNA does not comprise the entire coding sequence of the native cyanovirin, the DNA or cDNA can be subcloned as part of a gene fusion. In a transcriptional gene fusion, the DNA or cDNA will contain its own control sequence directing appropriate production of protein (e.g., ribosome binding site, translation initiation codon, etc.), and the transcriptional control sequences (e.g., promoter elements and/or enhancers) will be provided by the vector. In a translational gene fusion, transcriptional control sequences as well as at least some of the translational control sequences (i.e., the translational initiation codon) will be provided by the vector. In the case of a translational gene fusion, a chimeric protein will be produced.

Genes also can be constructed for specific fusion proteins containing a functional cyanovirin component plus a fusion component conferring additional desired attribute(s) to the composite protein. For example, a fusion sequence for a toxin or immunological reagent, as defined above, can be added to facilitate purification and analysis of the functional protein (e.g., such as the FLAG-cyanovirin-N fusion protein detailed within Examples 2–5).

Genes can be specifically constructed to code for fusion proteins, which contain a cyanovirin coupled to an effector protein, such as a toxin or immunological reagent, for specific targeting to a virus or viral-infected cells, e.g., HIV and/or HIV-infected cells or influenza and/or influenza-infected cells. In these instances, the cyanovirin moiety serves not only as a neutralizing agent but also as a targeting agent to direct the effector activities of these molecules selectively against a given virus, such as HIV or influenza. Thus, for example, a therapeutic agent can be obtained by combining the HIV-targeting function or influenza-targeting function of a functional cyanovirin with a toxin aimed at neutralizing infectious virus and/or by destroying cells producing infectious virus, such as HIV or influenza. Similarly, a therapeutic agent can be obtained, which combines the viral-targeting function of a cyanovirin with the multivalency and effector functions of various immunoglobulin subclasses. Example 6 further illustrates the viral-targeting, specifically gp120-targeting, properties of a cyanovirin.

Similar rationales underlie extensive developmental therapeutic efforts exploiting the HIV gp120-targeting properties of sCD4. For example, sCD4-toxin conjugates have been prepared in which sCD4 is coupled to a Pseudomonas exotoxin component (Chaudhary et al., in *The Human Retrovirus*, Gallo et al., eds., Academic Press: San Diego, 1991, pp. 379–387; and Chaudhary et al., *Nature* 335, 369–372, 1988), or to a diphtheria toxin component (Aullo et al., *EMBO J.* 11, 575–583, 1992) or to a ricin A-chain component (Till et al., *Science* 242, 1166–1167, 1988). Likewise, sCD4-immunoglobulin conjugates have been prepared in attempts to decrease the rate of in vivo clearance of functional sCD4 activity, to enhance placental transfer, and to effect a targeted recruitment of immunological mechanisms of pathogen elimination, such as phagocytic engulfment and killing by antibody-dependent cell-mediated cytotoxicity, to kill and/or remove HIV-infected cells and virus (Capon et al., *Nature* 337, 525–531, 1989; Traunecker et al., *Nature* 339, 68–70, 1989; and Langner et al., 1993, supra). While such CD4-immunoglobulin conjugates (sometimes called "immunoadhesins") have, indeed, shown advantageous pharmacokinetic and distributional attributes in vivo, and anti-HIV effects in vitro, clinical results have been discouraging (Schooley et al., 1990, supra; Husson et al., 1992, supra; and Langner et al., 1993, supra). This is not surprising since clinical isolates of HIV, as opposed to laboratory strains, are highly resistant to binding and neutralization by sCD4 (Orloff et al., 1995, supra; and Moore et al., 1992, supra). Therefore, the extraordinarily broad targeting properties of a functional cyanovirin to viruses, e.g., primate retroviruses, in general, and clinical and laboratory strains, in particular (Boyd et al., 1995, supra; and Gustafson et al., 1995, supra), can be especially advantageous for combining with toxins, immunoglobulins and other selected effector proteins.

Viral-targeted conjugates can be prepared either by genetic engineering techniques (see, for example, Chaudhary et al., 1988, supra) or by chemical coupling of the targeting component with an effector component. The most feasible or appropriate technique to be used to construct a given cyanovirin conjugate or fusion protein will be selected based upon consideration of the characteristics of the particular effector molecule selected for coupling to a cyanovirin. For example, with a selected non-proteinaceous effector molecule, chemical coupling, rather than genetic engineering techniques, may be the only feasible option for creating the desired cyanovirin conjugate.

Accordingly, the present invention also provides nucleic acid molecules encoding cyanovirin fusion proteins. In particular, the present invention provides a nucleic acid molecule comprising SEQ ID NO:3 and substantially homologous sequences thereof. Also provided is a vector comprising a nucleic acid sequence encoding a cyanovirin fusion protein and a method of obtaining a cyanovirin fusion protein by expression of the vector encoding a cyanovirin fusion protein in a protein-synthesizing organism as described above. Accordingly, cyanovirin fusion proteins are also provided.

In view of the above, the present invention further provides an isolated and purified nucleic acid molecule, which comprises a cyanovirin coding sequence, such as one of the aforementioned nucleic acids, namely a nucleic acid molecule encoding an amino acid sequence of SEQ ID NO:2, a nucleic acid molecule encoding an amino acid sequence of SEQ ID NO:4, a nucleic acid molecule comprising a sequence of SEQ ID NO:1, or a nucleic acid molecule comprising a sequence of SEQ ID NO:3, coupled to a second nucleic acid encoding an effector protein. The first nucleic acid preferably comprises a nucleic acid sequence encoding at least nine contiguous amino acids of the amino acid sequence of SEQ ID NO:2, which encodes a functional cyanovirin, and the second nucleic acid preferably encodes an effector protein, such as a toxin or immunological reagent as described above.

Accordingly, the present invention also further provides an isolated and purified fusion protein encoded by a nucleic acid molecule comprising a sequence of SEQ ID NO:1, a nucleic acid molecule comprising a sequence of SEQ ID NO:3, a nucleic acid molecule encoding an amino acid sequence of SEQ ID NO:2, or a nucleic acid molecule encoding an amino acid sequence of SEQ ID NO:4, any one of which is coupled to a second nucleic acid encoding an effector protein. Preferably, the aforementioned nucleic acid molecules encode at least nine contiguous amino acids of the amino acid sequence of SEQ ID NO:2, which desirably have antiviral activity, coupled to an effector molecule, such as a toxin or immunological reagent as described above. Preferably, the effector molecule targets a virus, more preferably HIV or influenza, and, most preferably glycoprotein gp120 of HIV. If the at least nine contiguous amino acids of SEQ ID NO: 2 comprise amino acids 30–32, desirably amino acids 30–32 have been rendered glycosylation resistant, yet maintain antiviral activity. Preferably, amino acids 30–32 of SEQ ID NO: 2 have been rendered glycosylation resistant by deletion or substitution of amino acid 30. Preferably, amino acid 30 has been substituted with an amino acid selected from the group consisting of alanine, glutamine and valine. Optionally, amino acid 51 can be deleted or substituted with, for example, glycine.

The coupling can be effected at the DNA level or by chemical coupling as described above. For example, a cyanovirin-effector protein conjugate of the present invention can be obtained by (a) selecting a desired effector protein or peptide; (b) synthesizing a composite DNA coding sequence comprising a first DNA coding sequence comprising one of the aforementioned nucleic acid sequences, which codes for a functional cyanovirin, coupled to a second DNA coding sequence for an effector protein or peptide, e.g., a toxin or immunological reagent; (c) expressing said composite DNA coding sequence in an appropriate protein-synthesizing organism; and (d) purifyng the desired fusion protein or peptide to substantially pure form. Alternatively, a cyanovirin-effector molecule conjugate of the present invention can be obtained by (a) selecting a desired effector molecule and a cyanovirin or cyanovirin fusion protein; (b) chemically coupling the cyanovirin or cyanovirin fusion protein to the effector molecule; and (c) purifying the desired cyanovirin-effector molecule conjugate to substantially pure form.

Conjugates comprising a functional cyanovirin (e.g., an antiviral protein or antiviral peptide comprising at least nine contiguous amino acids of SEQ ID NO:2, such as SEQ ID NO: 2, wherein the at least nine contiguous amino acids bind to a virus, in particular an infectious virus, such as influenza virus or HIV, in which case the cyanovirin binds to gp120) coupled to an anti-cyanovirin antibody or at least one effector component, which can be the same or different, such as a toxin, an immunological reagent, or other functional reagent, can be designed even more specifically to exploit the unique viral targeting, e.g., gp120-targeting properties, of cyanovirins.

Other functional reagents that can be used as effector components in the present inventive conjugates can include, for example, polyethylene glycol, dextran, albumin and the like, whose intended effector functions may include one or more of the following: to improve stability of the conjugate; to increase the half-life of the conjugate; to increase resistance of the conjugate to proteolysis; to decrease the immunogenicity of the conjugate; to provide a means to attach or immobilize a functional cyanovirin onto a solid support matrix (e.g., see, for example, Harris, in *Poly(Ethylene Glycol) Chemistry: Biotechnical and Biomedical Applications,* Harris, ed., Plenum Press: New York (1992), pp. 1–14). Conjugates furthermore can comprise a functional cyanovirin coupled to more than one effector molecule, each of which, optionally, can have different effector functions (e.g., such as a toxin molecule (or an immunological reagent) and a polyethylene glycol (or dextran or albumin) molecule). Diverse applications and uses of functional proteins and peptides, such as in the present instance a functional cyanovirin, attached to or immobilized on a solid support matrix, are exemplified more specifically for poly(ethylene glycol) conjugated proteins or peptides in a review by Holmberg et al. (In *Poly(Ethylene Glycol) Chemistry: Biotechnical and Biomedical Applications,* Harris, ed., Plenum Press: New York, 1992, pp. 303–324). Preferred examples of solid support matrices include magnetic beads, a flow-through matrix, and a matrix comprising a contraceptive device, such as a condom, a diaphragm, a cervical cap, a vaginal ring or a sponge.

Example 6 reveals novel gp120-directed effects of cyanovirins. Additional insights have been reported by Esser et al. (*J. Virol.,* 73, 4360–4371, 1999). They described a series of studies that further confirmed that cyanovirins block gp120-mediated binding and fusion of intact HIV-1 virions to host cells. They also provided additional confirmation that cyanovirins inhibit envelope glycoprotein-mediated infectivity of other viruses, including feline immunodeficiency virus (FIV).

The range of antiviral activity (Boyd et al., 1995, supra) of cyanovirin against diverse $CD4^+$-tropic immunodeficiency virus strains in various target cells is remarkable; all tested strains of HIV-1, HIV-2 and SIV were similarly sensitive to cyanovirin; clinical isolates and laboratory strains showed essentially equivalent sensitivity. Cocultivation of chronically infected and uninfected CEM-SS cells with cyanovirin did not inhibit viral replication, but did cause a concentration-dependent inhibition of cell-to-cell fusion and virus transmission; similar results from binding and fusion inhibition assays employing HeLa-CD4-LTR-β-galactosidase cells were consistent with cyanovirin inhibition of virus-cell and/or cell-cell binding.

Figure 8:
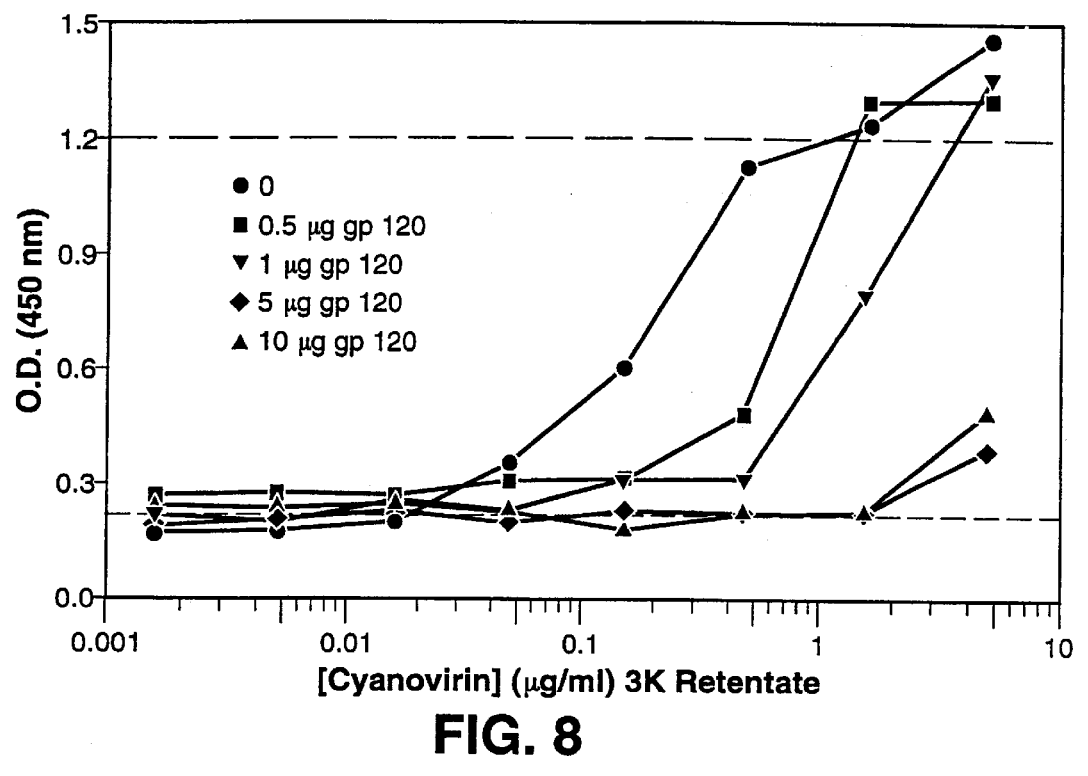
Figure 9:
FIG. 9 schematically illustrates a DNA coding sequence comprising a FLAG-cyanovirin-N coding sequence coupled to a Pseudomonas exotoxin coding sequence.
Figure 10:
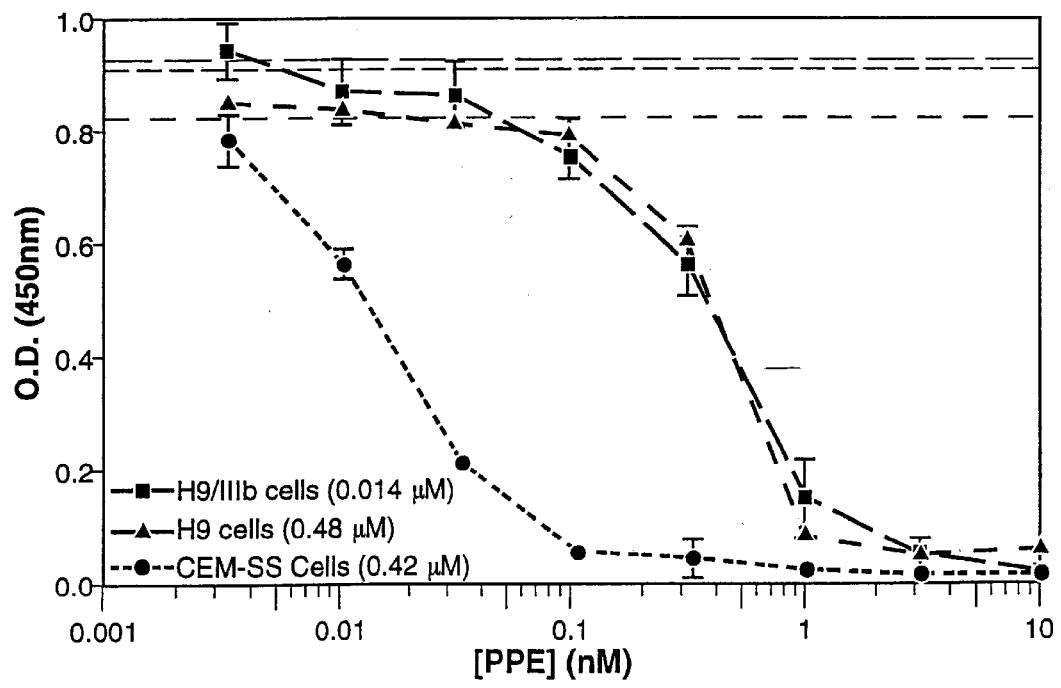
FIG. 10 is a graph of OD (450 nM) versus PPE concentration (nM), which illustrates selective killing of viral gp120-expressing (H9/IIIB) cells by a FLAG-cyaovirin-N/ Psuedomonas exotoxin protein conjugate (PPE).

The anti-viral, e.g., anti-HIV, activity of the cyanovirins and conjugates thereof of the present invention can be further demonstrated in a series of interrelated in vitro antiviral assays (Gulakowski et al., *J. Virol. Methods* 33, 87–100, 1991), which accurately predict for antiviral activity in humans. These assays measure the ability of compounds to prevent the replication of HIV and/or the cytopathic effects of HIV on human target cells. These measurements directly correlate with the pathogenesis of HIV-induced disease in vivo. The results of the analysis of the antiviral activity of cyanovirins or conjugates, as set forth in Examples 5 and 13 and as illustrated in FIGS. 8, 9 and 10, are believed to predict accurately the antiviral activity of these products in vivo in humans and, therefore, establish the utility of the present invention. Furthermore, since the present invention also provides methods of ex vivo use of cyanovirins and conjugates (e.g., see results set forth in Examples 5 and 13, and in FIGS. 6 and 7), the utility of cyanovirins and conjugates thereof is even more certain.

The cyanovirins and conjugates thereof of the present invention can be shown to inhibit a virus, specifically a retrovirus, more specifically an immunodeficiency virus, such as the human immunodeficiency virus, i.e., HIV-1 or HIV-2. The cyanovirins and conjugates of the present invention can be used to inhibit other retroviruses as well as other viruses (see, e.g., *Principles of Virology: Molecular Biology, Pathogenesis, and Control,* Flint et al., eds., ASM Press: Washington, D.C., 2000, particularly Chapter 19). Examples of viruses that may be treated in accordance with the present invention include, but are not limited to, Type C and Type D retroviruses, HTLV-1, HTLV-2, HIV, FIV, FLV, SIV, MLV, BLV, BIV, equine infectious virus, anemia virus, avian sarcoma viruses, such as Rous sarcoma virus (RSV), hepatitis type A, B, non-A and non-B viruses, arboviruses, varicella viruses, human herpes virus (e.g., HHV-6), measles, mumps and rubella viruses. Cyanovirins and conjugate thereof also can be used to inhibit influenza viral infection (see, e.g., *Fields Virology,* third edition, Fields et al., eds., Lippincott-Raven Publishers: Philadelphia, Pa., 1996, particularly Chapter 45) prophylactically and therapeutically in accordance with the methods set forth herein.

Accordingly, the present invention provides a method of inhibiting prophylactically or therapeutically a viral infection, in particular an influenza viral infection, of a host. The method comprises administering to the host an effective amount of an antiviral protein, antiviral peptide, antiviral protein conjugate or antiviral peptide conjugate comprising at least nine contiguous amino acids of SEQ ID NO:2, wherein the at least nine contiguous amino acids are nonglycosylated and have antiviral activity, whereupon the viral infection is inhibited. The antiviral protein or peptide can be derived from a cyanovirin obtained from *Nostoc ellipsosporum* or recombinantly produced in accordance with the methods described above. Nonglycosylated antiviral proteins and peptides can be produced in prokaryotic cells/organisms. Amino acid 51 in such nonglycosylated antiviral proteins and antiviral peptides can be deleted or substituted, for example, with glycine. Nonglycosylated antiviral proteins and peptides also can be produced in eukaryotic cells/organisms by expressing a portion of a cyanovirin, such as that of SEQ ID NO: 2, that does not contain a glycosylation site or all or a portion of a cyanovirin, such as that of SEQ ID NO: 2, which contains a glycosylation site that has been rendered glycosylation-resistant as described and exemplified herein. If the at least nine contiguous amino acids of SEQ ID NO: 2 comprise amino acids 30–32, desirably amino acid 30 has been deleted or substituted. If amino acid 30 is substituted, preferably the amino acid is substituted with an amino acid selected from the group consisting of alanine, glutamine and valine and, if the at least nine contiguous amino acids of SEQ ID NO: 2 further comprises amino acid 51, optionally, amino acid 51 is deleted or substituted, for example, with glycine. When the viral infection is an influenza viral infection, preferably the antiviral protein, antiviral peptide, antiviral protein conjugate or antiviral peptide conjugate is administered topically to the host, preferably to the respiratory system of the host, preferably as an aerosol or microparticulate powder.

Cyanovirins and conjugates thereof collectively comprise proteins and peptides, and, as such, are particularly susceptible to hydrolysis of amide bonds (e.g., catalyzed by peptidases) and disruption of essential disulfide bonds or formation of inactivating or unwanted disulfide linkages (Carone et al., *J. Lab. Clin. Med.* 100, 1–14, 1982). There are various ways to alter molecular structure, if necessary, to provide enhanced stability to the cyanovirin or conjugate thereof (Wunsch, *Biopolymers* 22, 493–505, 1983; and Samanen, in *Polymeric Materials in Medication,* Gebelein et al., eds., Plenum Press: New York, 1985, pp. 227–242), which may be essential for preparation and use of pharmaceutical compositions containing cyanovirins or conjugates thereof for therapeutic or prophylactic applications against viruses, e.g., HIV. Possible options for useful chemical modifications of a cyanovirin or conjugate include, but are not limited to, the following (adapted from Samanen, J. M., 1985, supra): (a) olefin substitution, (b) carbonyl reduction, (c) D-amino acid substitution, (d) N-methyl substitution, (e) C-methyl substitution, (f) C-C'-methylene insertion, (g) dehydro amino acid insertion, (h) retro-inverso modification, (i) N-terminal to C-terminal cyclization, and (j) thiomethylene modification. Cyanovirins and conjugates thereof also can be modified by covalent attachment of carbohydrate and polyoxyethylene derivatives, which are expected to enhance stability and resistance to proteolysis (Abuchowski et al., in *Enzymes as Drugs,* Holcenberg et al., eds., John Wiley: New York, 1981, pp. 367–378).

Other important general considerations for design of delivery strategy systems and compositions, and for routes of administration, for protein and peptide drugs, such as cyanovirins and conjugates thereof (Eppstein, *CRC Crit. Rev. Therapeutic Drug Carrier Systems* 5, 99–139, 1988; Siddiqui et al., *CRC Crit. Rev. Therapeutic Drug Carrier Systems* 3, 195–208, 1987); Banga et al., *Int. J. Pharmaceutics* 48, 15–50, 1988; Sanders, *Eur. J. Drug Metab. Pharmacokinetics* 15, 95–102, 1990; and Verhoef, *Eur. J. Drug Metab. Pharmacokinetics* 15, 83–93, 1990), also apply. The appropriate delivery system for a given cyanovirin or conjugate thereof will depend upon its particular nature, the particular clinical application, and the site of drug action. As with any protein or peptide drug, oral delivery of a cyanovirin or a conjugate thereof will likely present special problems, due primarily to instability in the gastrointestinal tract and poor absorption and bioavailability of intact, bioactive drug therefrom. Therefore, especially in the case of oral delivery, but also possibly in conjunction with other routes of delivery, it will be necessary to use an absorption-enhancing agent in combination with a given cyanovirin or conjugate thereof. A wide variety of absorption-enhancing agents have been investigated and/or applied in combination with protein and peptide drugs for oral delivery and for delivery by other routes (Verhoef, 1990, supra; van Hoogdalem, *Pharmac. Ther.* 44, 407–443, 1989; Davis, *J. Pharm. Pharmacol.* 44(Suppl. 1), 186–190, 1992). Most commonly, typical enhancers fall into the general categories of (a) chelators, such as EDTA, salicylates, and N-acyl derivatives of collagen, (b) surfactants, such as lauryl sulfate and polyoxyethylene-9-lauryl ether, (c) bile salts, such as glycholate and taurocholate, and derivatives, such as taurodihydrofusidate, (d) fatty acids, such as oleic acid and capric acid, and their derivatives, such as acylcarnitines, monoglycerides and diglycerides, (e) non-surfactants, such as unsaturated cyclic ureas, (f) saponins, (g) cyclodextrins, and (h) phospholipids.

Other approaches to enhancing oral delivery of protein and peptide drugs, such as the cyanovirins and conjugates thereof, can include aforementioned chemical modifications to enhance stability to gastrointestinal enzymes and/or increased lipophilicity. Alternatively, or in addition, the protein or peptide drug can be administered in combination with other drugs or substances, which directly inhibit proteases and/or other potential sources of enzymatic degradation of proteins and peptides. Yet another alternative approach to prevent or delay gastrointestinal absorption of protein or peptide drugs, such as cyanovirins or conjugates, is to incorporate them into a delivery system that is designed to protect the protein or peptide from contact with the proteolytic enzymes in the intestinal lumen and to release the intact protein or peptide only upon reaching an area favorable for its absorption. A more specific example of this strategy is the use of biodegradable microcapsules or microspheres, both to protect vulnerable drugs from degradation, as well as to effect a prolonged release of active drug (Deasy, in *Microencapsulation and Related Processes,* Swarbrick, ed., Marcell Dekker, Inc.: New York, 1984, pp. 1–60, 88–89, 208–211). Microcapsules also can provide a useful way to effect a prolonged delivery of a protein and peptide drug, such as a cyanovirin or conjugate thereof, after injection (Maulding, *J. Controlled Release* 6, 167–176, 1987).

Given the aforementioned potential complexities of successful oral delivery of a protein or peptide drug, it is fortunate that there are numerous other potential routes of delivery of a protein or peptide drug, such as a cyanovirin or conjugate thereof. These routes include intravenous, intraarterial, intrathecal, intracisternal, buccal, rectal, nasal, pulmonary, transdermal, vaginal, ocular, and the like (Eppstein, 1988, supra; Siddiqui et al., 1987, supra; Banga et al., 1988, supra; Sanders, 1990, supra; Verhoef, 1990, supra; Barry, in *Delivery Systems for Peptide Drugs,* Davis et al., eds., Plenum Press: New York, 1986, pp. 265–275; and Patton et al., *Adv. Drug Delivery Rev.* 8, 179–196, 1992). With any of these routes, or, indeed, with any other route of administration or application, a protein or peptide drug, such as a cyanovirin or conjugate thereof, may initiate an immunogenic reaction. In such situations it may be necessary to modify the molecule in order to mask immunogenic groups. It also can be possible to protect against undesired immune responses by judicious choice of method of formulation and/or administration. For example, site-specific delivery can be employed, as well as masking of recognition sites from the immune system by use or attachment of a so-called tolerogen, such as polyethylene glycol, dextran, albumin, and the like (Abuchowski et al., 1981, supra; Abuchowski et al., *J. Biol. Chem.* 252, 3578–3581, 1977; Lisi et al.,*J. Appl. Biochem.* 4, 19–33, 1982; and Wileman et al., *J. Pharm. Pharmacol.* 38, 264–271, 1986). Such modifications also can have advantageous effects on stability and half-life both in vivo and ex vivo.

Procedures for covalent attachment of molecules, such as polyethylene glycol, dextran, albumin and the like, to proteins, such as cyanovirins or conjugates thereof, are well-known to those skilled in the art, and are extensively documented in the literature (e.g., see Davis et al., In *Peptide and Protein Drug Delivery,* Lee, ed., Marcel Dekker: New York, 1991, pp. 831–864).

Other strategies to avoid untoward immune reactions can also include the induction of tolerance by administration initially of only low doses. In any event, it will be apparent from the present disclosure to one skilled in the art that for any particular desired medical application or use of a cyanovirin or conjugate thereof, the skilled artisan can select from any of a wide variety of possible compositions, routes of administration, or sites of application, what is advantageous.

Accordingly, the antiviral cyanovirins and conjugates thereof of the present invention can be formulated into various compositions for use, for example, either in therapeutic treatment methods for infected individuals, or in prophylactic methods against viral, e.g., HIV and influenza virus, infection of uninfected individuals.

The present invention also provides a composition, such as a pharmaceutical composition, which comprises an isolated and purified cyanovirin, a cyanovirin conjugate, a matrix-anchored cyanovirin or a matrix-anchored cyanovirin conjugate, such as an antiviral effective amount thereof. The composition can further comprise a carrier, such as a pharmaceutically acceptable carrier. The composition can further comprise at least one additional antiviral compound other than a cyanovirin or conjugate thereof, such as in an antiviral effective amount. Suitable antiviral compounds include AZT, ddI, ddC, gancyclovir, fluorinated dideoxynucleosides, nevirapine, R82913, Ro 31-8959, BI-RJ-70, acyclovir, α-interferon, recombinant sCD4, michellamines, calanolides, nonoxynol-9, gossypol and derivatives thereof, and gramicidin. If the composition is to be used to induce an immune response, it comprises an immune response-inducing amount of a cyanovirin or conjugate thereof and can further comprise an immunoadjuvant, such as polyphosphazene polyelectrolyte. The cyanovirin used in the composition, e.g., pharmaceutical composition, can be isolated and purified from nature or genetically engineered. Similarly, the cyanovirin conjugate can be genetically engineered or chemically coupled.

The present inventive compositions can be administered to a host, such as a human, so as to inhibit viral infection in a prophylactic or therapeutic method. The compositions of the present invention are particularly useful in inhibiting the growth or replication of a virus, such as influenza virus or a retrovirus, in particular an immunodeficiency virus, such as HIV, specifically HIV-1 and HIV-2. The compositions are useful in the therapeutic or prophylactic treatment of animals, such as humans, who are infected with a virus or who are at risk for viral infection, respectively. The compositions also can be used to treat objects or materials, such as medical equipment, supplies, or fluids, including biological fluids, such as blood, blood products and vaccine formulations, cells, tissues and organs, to remove or inactivate virus in an effort to prevent or treat viral infection of an animal, such as a human. Such compositions also are useful to prevent sexual transmission of viral infections, e.g., HIV, which is the primary way in which the world's AIDS cases are contracted (Merson, 1993, supra).

Potential virucides used or being considered for use against sexual transmission of HIV are very limited; present agents in this category include, for example, nonoxynol-9 (Bird, *AIDS* 5, 791–796, 1991), gossypol and derivatives (Polsky et al., *Contraception* 39, 579–587, 1989; Lin, *Antimicrob. Agents Chemother.* 33, 2149–2151, 1989; and Royer, *Pharmacol. Res.* 24, 407–412, 1991), and gramicidin (Bourinbair, *Life Sci./Pharmacol. Lett.* 54, PL5–9, 1994; and Bourinbair et al., *Contraception* 49, 131–137, 1994). The method of prevention of sexual transmission of viral infection, e.g., HIV infection, in accordance with the present invention comprises vaginal, rectal, oral, penile or other topical treatment with an antiviral effective amount of a cyanovirin and/or cyanovirin conjugate, alone or in combination with another antiviral compound as described above.

In a novel approach to anti-HIV prophylaxis pursued under auspices of the U.S. National Institute of Allergy and Infectious Diseases (NIAID) (e.g., as conveyed by Painter, *USA Today*, Feb. 13, 1996), vaginal suppository instillation of live cultures of lactobacilli was being evaluated in a 900-woman study. This study was based especially upon observations of anti-HIV effects of certain $H_2O_2$-producing lactobacilli in vitro (e.g., see published abstract by Hilier, from NIAID-sponsored Conference on "Advances in AIDS Vaccine Development", Bethesda, Md., Feb. 11–15, 1996). Lactobacilli readily populate the vagina, and indeed are a predominant bacterial population in most healthy women (Redondo-Lopez et al., *Rev. Infect. Dis.* 12, 856–872, 1990; Reid et al., *Clin. Microbiol. Rev.* 3, 335–344, 1990; Bruce and Reid, *Can. J. Microbiol.* 34, 339–343, 1988; reu et al., *J. Infect. Dis.* 171, 1237–1243, 1995; Hilier et al., *Clin. Infect. Dis.* 16(Suppl 4), S273–S281; Agnew et al., *Sex. Transm. Dis.* 22, 269–273, 1995). Lactobacilli are also prominent, nonpathogenic inhabitants of other body cavities such as the mouth, nasopharynx, upper and lower gastrointestinal tracts, and rectum.

It is well-established that lactobacilli can be readily transformed using available genetic engineering techniques to incorporate a desired foreign DNA coding sequence, and that such lactobacilli can be made to express a corresponding desired foreign protein (see, e.g., Hols et al., *Appl. and Environ. Microbiol.* 60, 1401–1413, 1994). Therefore, within the context of the present disclosure, it will be appreciated by one skilled in the art that viable host cells containing a DNA sequence or vector of the present invention, and expressing a protein of the present invention, can be used directly as the delivery vehicle for a cyanovirin or conjugate thereof to the desired site(s) in vivo. Preferred host cells for such delivery of cyanovirins or conjugates thereof directly to desired site(s), such as, for example, to a selected body cavity, can comprise bacteria. More specifically, such host cells can comprise suitably engineered strain(s) of lactobacilli, enterococci, or other common bacteria, such as *E. coli*, normal strains of which are known to commonly populate body cavities. More specifically yet, such host cells can comprise one or more selected nonpathogenic strains of lactobacilli, such as those described by Andreu et al. (1995, supra), especially those having high adherence properties to epithelial cells, such as, for example, adherence to vaginal epithelial cells, and suitably transformed using the DNA sequences of the present invention.

As reviewed by McGroarty (*FEMS Immunol. Med. Microbiol.* 6, 251–264, 1993) the "probiotic" or direct therapeutic application of live bacteria, particularly bacteria that occur normally in nature, more particularly lactobacilli, for treatment or prophylaxis against pathogenic bacterial or yeast infections of the urogenital tract, in particular the female urogenital tract, is a well-established concept. Recently, the use of a conventional probiotic strategy, in particular the use of live lactobacilli, to inhibit sexual transmission of HIV has been suggested, based specifically upon the normal, endogenous production of virucidal levels of $H_2O_2$ and/or lactic acid and/or other potentially virucidal substances by certain normal strains of lactobacilli (e.g., Hilier, 1996, supra). However, the present inventive use of non-mammalian cells, particularly bacteria, more particularly lactobacilli, specifically engineered with a foreign gene, more specifically a cyanovirin gene, to express an antiviral substance, more specifically a protein, and even more specifically a cyanovirin, is heretofore unprecedented as a method of treatment of an animal, specifically a human, to prevent infection by a virus, specifically a retrovirus, more specifically HIV-1 or HIV-2.

Elmer et al. (*JAMA* 275, 870–876, 1996) have recently speculated that "genetic engineering offers the possibility of using microbes to deliver specific actions or products to the colon or other mucosal surfaces . . . other fertile areas for future study include defining the mechanisms of action of various biotherapeutic agents with the possibility of applying genetic engineering to enhance activities." Elmer et al. (1996, supra) further point out that the terms "probiotic" and "biotherapeutic agent" have been used in the literature to describe microorganisms that have antagonistic activity toward pathogens in vivo; those authors more specifically prefer the term "biotherapeutic agent" to denote "microorganisms having specific therapeutic properties.

In view of the present disclosure, one skilled in the art will appreciate that the present invention teaches an entirely novel type of "probiotic" or "biotherapeutic" treatment using specifically engineered strains of microorganisms provided herein which do not occur in nature. Nonetheless, available teachings concerning selection of optimal microbial strains, in particular bacterial strains, for conventional probiotic or biotherapeutic applications can be employed in the context of the present invention. For example, selection of optimal lactobacillus strains for genetic engineering, transformation, direct expression of cyanovirins or conjugates thereof, and direct probiotic or biotherapeutic applications, to treat or prevent HIV infection, can be based upon the same or similar criteria, such as those described by Elmer et al. (1996, supra), typically used to select normal, endogenous or "nonengineered" bacterial strains for conventional probiotic or biotherapeutic therapy. Furthermore, the recommendations and characteristics taught by McGroarty, particularly for selection of optimal lactobacillus strains for conventional probiotic use against female urogenital infections, are pertinent to the present invention: " . . . lactobacilli chosen for incorporation into probiotic preparations should be easy and, if possible, inexpensive to cultivate . . . strains should be stable, retain viability following freeze-drying and, of course, be non-pathogenic to the host . . . it is essential that lactobacilli chosen for use in probiotic preparations should adhere well to the vaginal epithelium . . . ideally, artificially implanted lactobacilli should adhere to the vaginal epithelium, integrate with the indigenous microorganisms present, and proliferate" (McGroarty, 1993 supra). While McGroarty's teachings specifically address selections of "normal" lactobacillus strains for probiotic uses against pathogenic bacterial or yeast infections of the female urogenital tract, similar considerations will apply to the selection of optimal bacterial strains for genetic engineering and "probiotic" or "biotherapeutic" application against viral infections as particularly encompassed by the present invention.

Accordingly, the method of the present invention for the prevention of sexual transmission of viral infection, e.g., HIV infection, comprises vaginal, rectal, oral, penile, or other topical, insertional, or instillational treatment with an antiviral effective amount of a cyanovirin, a cyanovirin conjugate, a matrix-anchored cyanovirin or conjugate thereof, and/or viable host cells transformed to express a cyanovirin or conjugate thereof, alone or in combination with one or more other antiviral compound (e.g., as described above).

Compositions for use in the prophylactic or therapeutic treatment methods of the present invention comprise one or more cyanovirin(s) or conjugate(s) thereof, either one of which can be matrix-anchored, and desirably a carrier therefor, such as a pharmaceutically acceptable carrier. Pharmaceutically acceptable carriers are well-known to those who are skilled in the art, as are suitable methods of administration. The choice of carrier will be determined in part by the particular cyanovirin or conjugate thereof, as well as by the particular method used to administer the composition.

One skilled in the art will appreciate that various routes of administering a drug are available, and, although more than one route can be used to administer a particular drug, a particular route can provide a more immediate and more effective reaction than another route. Furthermore, one skilled in the art will appreciate that the particular pharmaceutical carrier employed will depend, in part, upon the particular cyanovirin or conjugate thereof employed, and the chosen route of administration. Accordingly, there is a wide variety of suitable formulations of the composition of the present invention.

Formulations suitable for oral administration can consist of liquid solutions, such as an effective amount of the compound dissolved in diluents, such as water, saline, or fruit juice; capsules, sachets or tablets, each containing a predetermined amount of the active ingredient, as solid, granules or freeze-dried cells; solutions or suspensions in an aqueous liquid; and oil-in-water emulsions or water-in-oil emulsions. Tablet forms can include one or more of lactose, mannitol, corn starch, potato starch, microcrystalline cellulose, acacia, gelatin, colloidal silicon dioxide, croscarmellose sodium, talc, magnesium stearate, stearic acid, and other excipients, colorants, diluents, buffering agents, moistening agents, preservatives, flavoring agents, and pharmacologically compatible carriers. Suitable formulations for oral delivery can also be incorporated into synthetic and natural polymeric microspheres, or other means to protect the agents of the present invention from degradation within the gastrointestinal tract (see, for example, Wallace et al., *Science* 260, 912–915, 1993).

The cyanovirins or conjugates thereof, alone or in combination with other antiviral compounds, can be made into aerosol formulations or microparticulate powder formulations to be administered via inhalation. These aerosol formulations can be placed into pressurized acceptable propellants, such as dichlorodifluoromethane, propane, nitrogen and the like.

The cyanovirins or conjugates thereof, alone or in combinations with other antiviral compounds or absorption modulators, can be made into suitable formulations for transdermal application and absorption (Wallace et al., 1993, supra). Transdermal electroporation or iontophoresis also can be used to promote and/or control the systemic delivery of the compounds and/or compositions of the present invention through the skin (e.g., see Theiss et al., *Meth. Find. Exp. Clin. Pharmacol.* 13, 353–359, 1991).

Formulations suitable for topical administration include lozenges comprising the active ingredient in a flavor, usually sucrose and acacia or tragacanth; pastilles comprising the active ingredient in an inert base, such as gelatin and glycerin, or sucrose and acacia; and mouthwashes comprising the active ingredient in a suitable liquid carrier; as well as creams, emulsions, gels and the like containing, in addition to the active ingredient, such as, for example, freeze-dried lactobacilli or live lactobacillus cultures genetically engineered to directly produce a cyanovirin or conjugate thereof of the present invention, such carriers as are known in the art. Topical administration is preferred for the prophylactic and therapeutic treatment of influenza viral infection, such as through the use of an inhaler, for example.

Formulations for rectal administration can be presented as a suppository with a suitable base comprising, for example, cocoa butter or a salicylate. Formulations suitable for vaginal administration can be presented as pessaries, tampons, creams, gels, pastes, foams, or spray formulas containing, in addition to the active ingredient, such as, for example, freeze-dried lactobacilli or live lactobacillus cultures genetically engineered to directly produce a cyanovirin or conjugate thereof of the present invention, such carriers as are known in the art to be appropriate. Similarly, the active ingredient can be combined with a lubricant as a coating on a condom. Indeed, preferably, the active ingredient is applied to any contraceptive device, including, but not limited to, a condom, a diaphragm, a cervical cap, a vaginal ring and a sponge.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (lyophilized) condition requiring only the addition of the sterile liquid carrier, for example, water, for injections, immediately prior to use. Extemporaneous injection solutions and suspensions can be prepared from sterile powders, granules, and tablets of the kind previously described.

Formulations comprising a cyanovirin or cyanovirin conjugate suitable for virucidal (e.g., HIV) sterilization of inanimate objects, such as medical supplies or equipment, laboratory equipment and supplies, instruments, devices, and the like, can, for example, be selected or adapted as appropriate, by one skilled in the art, from any of the aforementioned compositions or formulations. Preferably, the cyanovirin is produced by recombinant DNA technology. The cyanovirin conjugate can be produced by recombinant DNA technology or by chemical coupling of a cyanovirin with an effector molecule as described above. Similarly, formulations suitable for ex vivo sterilization or removal of virus, such as infectious virus, from a sample, such as blood, blood products, sperm, or other bodily products, such as a fluid, cells, a tissue or an organ, or any other solution, suspension, emulsion, vaccine formulation (such as in the removal of infectious virus), or any other material which can be administered to a patient in a medical procedure, can be selected or adapted as appropriate by one skilled in the art, from any of the aforementioned compositions or formulations. However, suitable formulations for ex vivo sterilization or removal of virus from a sample or on an inanimate object are by no means limited to any of the aforementioned formulations or compositions. For example, such formulations or compositions can comprise a functional cyanovirin, such as that which is encoded by SEQ ID NO: 2, or antiviral fragment thereof, such as a fragment comprising at least nine contiguous amino acids of SEQ ID NO:2, wherein the at least nine contiguous amino acids bind to a virus, or a conjugate of either of the foregoing, attached to a solid support matrix, to facilitate contacting or binding infectious virus in a sample or removing infectious virus from a sample as described above, e.g., a bodily product such as a fluid, cells, a tissue or an organ from an organism, in particular a mammal, such as a human, including, for example, blood, a component of blood, or sperm. Preferably, the antiviral protein comprises SEQ ID NO: 2. Also preferably, the at least nine contiguous amino acids bind gp120 of HIV, in particular infectious HIV. As a more specific example, such a formulation or composition can comprise a functional cyanovirin, or conjugate thereof, attached to (e.g., coupled to or immobilized on) a solid support matrix comprising magnetic beads, to facilitate contacting, binding and removal of infectious virus, and to enable magnet-assisted removal of the virus from a sample as described above, e.g., a bodily product such as a fluid, cells, a tissue or an organ, e.g., blood, a component of blood, or sperm. Alternatively, and also preferably, the solid support matrix comprises a contraceptive device, such as a condom, a diaphragm, a cervical cap, a vaginal ring or a sponge.

As an even more specific illustration, such a composition (e.g., for ex vivo) can comprise a functional (e.g., gp120-binding, HIV-inactivating) cyanovirin, or conjugate thereof, attached to a solid support matrix, such as magnetic beads or a flow-through matrix, by means of an anti-cyanovirin antibody or at least one effector component, which can be the same or different, such as polyethylene glycol, albumin or dextran. The conjugate can further comprise at least one effector component, which can be the same or different, selected from the group consisting of an immunological reagent and a toxin. A flow-through matrix would comprise, for instance, a configuration similar to an affinity column. The cyanovirin can be covalently coupled to a solid support matrix via an anti-cyanovirin antibody, described below. Methods of attaching an antibody to a solid support matrix are well-known in the art (see, for example, Harlow and Lane. *Antibodies: A Laboratory Manual*, Cold Springs Harbor Laboratory: Cold Spring Harbor, N.Y., 1988). Alternatively, the solid support matrix, such as magnetic beads, can be coated with streptavidin, in which case the cyanovirin or fragment thereof (which comprises at least nine contiguous amino acids of SEQ ID NO: 2), or a conjugate of either one, is biotinylated. The at least nine contiguous amino acids of SEQ ID NO: 2 desirably have antiviral activity and preferably bind gp120 of HIV, which preferably is infectious. Preferably, the antiviral protein comprises SEQ ID NO: 2. Such a composition can be prepared, for example, by biotinylating the cyanovirin, or conjugate thereof, and then contacting the biotinylated protein or peptide with a (commercially available) solid support matrix, such as magnetic beads, coated with streptavidin. The use of biotinylation as a means to attach a desired biologically active protein or peptide to a streptavidin-coated support matrix, such as magnetic beads, is well-known in the art. Example 7 specifically describes a procedure applicable to biotinylation of cyanovirin-N and attachment of the biotinylated protein to streptavidin-coated magnetic beads. Example 7 also illustrates another important principle that is critical to the present invention: for any given formulation or composition comprising a functional cyanovirin, or conjugate thereof, attached to or immobilized on a solid support matrix, it is essential that the formulation or composition retain the desired (i.e., in this instance, the virus binding (e.g., gp120-binding) and virus-inactivating (e.g., HIV)) properties of the functional cyanovirin, or conjugate thereof, itself.

One skilled in the art will appreciate that a suitable or appropriate formulation can be selected, adapted or developed based upon the particular application at hand.

For ex vivo uses, such as virucidal treatments of inanimate objects or materials, blood or blood products, or tissues, the amount of cyanovirin, or conjugate or composition thereof, to be employed should be sufficient that any virus or virus-producing cells present will be rendered noninfectious or will be destroyed. For example, for HIV, this would require that the virus and/or the virus-producing cells be exposed to concentrations of cyanovirin-N in the range of 0.1–1000 nM. Similar considerations apply to in vivo applications. Therefore, the designation of "antiviral effective amount" is used generally to describe the amount of a particular cyanovirin, conjugate or composition thereof required for antiviral efficacy in any given application.

In view of the above, the present invention also provides a method of inhibiting prophylactically or therapeutically a viral infection of a host in which an antiviral effective amount of an above-described conjugate is administered to the host. Upon administration of the antiviral effective amount of the conjugate, the viral infection is inhibited.

The present invention additionally provides a method of prophylactically or therapeutically inhibiting a viral infection of a host in which an antiviral effective amount of a composition comprising an isolated and purified antiviral protein, antiviral peptide, antiviral protein conjugate or antiviral peptide conjugate comprising at least nine contiguous amino acids of SEQ ID NO: 2 having antiviral activity and attached to a solid support matrix is administered to the host. Upon administration of the antiviral effective amount of the composition, the viral infection is inhibited. Preferably, the solid support matrix is a contraceptive device, such as a condom, diaphragm, cervical cap, vaginal ring or sponge. In an alternative embodiment, a solid support matrix can be surgically implanted and later removed.

For in vivo uses, the dose of a cyanovirin, or conjugate or composition thereof, administered to an animal, particularly a human, in the context of the present invention should be sufficient to effect a prophylactic or therapeutic response in the individual over a reasonable time frame. The dose used to achieve a desired antiviral concentration in vivo (e.g., 0.1–1000 nM) will be determined by the potency of the particular cyanovirin or conjugate employed, the severity of the disease state of infected individuals, as well as, in the case of systemic administration, the body weight and age of the infected individual. The size of the dose also will be determined by the existence of any adverse side effects that may accompany the particular cyanovirin, or conjugate or composition thereof, employed. It is always desirable, whenever possible, to keep adverse side effects to a minimum.

The present invention also provides a method of removing virus, such as infectious virus, from a sample. The method comprises contacting the sample with a composition comprising an isolated and purified antiviral protein, antiviral peptide, antiviral protein conjugate, or antiviral peptide conjugate, comprising at least nine contiguous amino acids of SEQ ID NO:2. The at least nine contiguous amino acids desirably have antiviral activity and bind to the virus and the antiviral protein or antiviral peptide (or conjugate of either of the foregoing) is attached to a solid support matrix, such as a magnetic bead. "Attached" is used herein to refer to attachment to (or coupling to) and immobilization in or on a solid support matrix. While any means of attachment can be used, preferably, attachment is by covalent bonds. The method further comprises separating the sample and the composition by any suitable means, whereupon the virus, such as infectious virus, is removed from the sample. Preferably, the antiviral protein comprises SEQ ID NO:2. In one embodiment, the antiviral protein or antiviral peptide is conjugated with an anti-cyanovirin antibody or at least one effector component, which can be the same or different, selected from polyethylene glycol, dextran and albumin, in which case the antiviral protein or antiviral peptide is desirably attached to the solid support matrix through at least one effector component. The antiviral protein or antiviral peptide can be further conjugated with at least one effector component, which can be the same or different, selected from the group consisting of an immunological reagent and a toxin. In another embodiment, the solid support matrix is coated with streptavidin and the antiviral protein or antiviral peptide is biotinylated. Through biotin, the biotinylated antiviral protein/peptide is attached to the streptavidin-coated solid support matrix. Other types of means, as are known in the art, can be used to attach a functional cyanovirin (i.e., an antiviral protein or peptide or conjugate of either of the foregoing as described above) to a solid support matrix, such as a magnetic bead, in which case contact with a magnet is used to separate the sample and the composition. Similarly, other types of solid support matrices can be used, such as a matrix comprising a porous surface or membrane, over or through which a sample is flowed or percolated, thereby selectively entrapping or removing infectious virus from the sample. The choice of solid support matrix, means of attachment of the functional cyanovirin to the solid support matrix, and means of separating the sample and the matrix-anchored cyanovirin will depend, in part, on the sample (e.g., fluid vs. tissue) and the virus to be removed. It is expected that the use of a selected coupling molecule can confer certain desired properties to a matrix, comprising a functional cyanovirin coupled therewith, that may have particularly advantageous properties in a given situation. Preferably, the sample is blood, a component of blood, sperm, cells, tissue or an organ. Also, preferably the sample is a vaccine formulation, in which case the virus that is removed is infectious, such as HIV, although HIV, in particular infectious HIV, can be removed from other samples in accordance with this method. Such methods also have utility in real time ex vivo removal of virus or virus infected cells from a bodily fluid, such as blood, e.g., in the treatment of viral infection, or in the removal of virus from blood or a component of blood, e.g., for transfusion, in the inhibition or prevention of viral infection. Such methods also have potential utility in dialysis, such as kidney dialysis, and in removing virus from sperm obtained from a donor for in vitro and in vivo fertilization. The methods also have applicability in the context of tissue and organ transplantations.

For instance, the skilled practitioner might select a poly (ethylene glycol) molecule for attaching a functional cyanovirin to a solid support matrix, thereby to provide a matrix-anchored cyanovirin, wherein the cyanovirin is attached to the matrix by a longer "tether" than would be feasible or possible for other attachment methods, such as biotinylation/streptavidin coupling. A cyanovirin coupled by a poly(ethylene glycol) "tether" to a solid support matrix (such as magnetic beads, porous surface or membrane, and the like) can permit optimal exposure of a binding surface, epitope, hydrophobic or hydrophobic focus, and/or the like, on a functional cyanovirin in a manner that, in a given situation and/or for a particular virus, facilitates the binding and/or inactivation of the virus. A preferred solid support matrix is a magnetic bead such that separation of the sample and the composition is effected by a magnet. In a preferred embodiment of the method, the at least nine contiguous amino acids bind gp120 of HIV and HIV is removed from the sample.

In summary, a cyanovirin attached to a solid support matrix, such as a magnetic bead, can be used to remove virus, in particular infectious virus, including immunodeficiency virus, such as HIV, e.g., HIV-1 or HIV-2, from a sample, such as a sample comprising both infectious and noninfectious virus. In contrast to previously disclosed methods of inactivating or destroying virus in a sample, the present inventive method utilizes cyanovirins, which bind irreversibly to virus, such as infectious virus, in particular infectious immunodeficiency virus, e.g., HIV, specifically HIV-1 or HIV-2. The infectious viral particle is permanently fixed to the antiviral agent and unable to infect host cells. The present inventive method enables separation of infectious from non-infectious virus and, therefore, is advantageous over other methods currently available in the art. In this regard, it has been unexpectedly observed that a cyanovirin recognizes a conformation or a portion of gp120 characteristic of infectious HIV. Therefore, only infectious virus is bound by the cyanovirin, while non-infectious virus remains in the sample. One of ordinary skill in the art will appreciate the advantages of using the present inventive matrix-anchored cyanovirins to produce pools of non-infectious virus. The present inventive method also can be used to remove gp120-presenting cells, e.g., infected cells that have gp120 on their surfaces, from a sample.

The present invention, therefore, further provides a composition comprising naturally-occurring, non-infectious virus, such as a composition produced as described above. The composition can further comprise a carrier, such as a biologically or pharmaceutically acceptable carrier, and an immuno-adjuvant. Preferably, the noninfectious virus is an immunodeficiency virus, such as HIV, e.g., HIV-1 or HIV-2. Alternatively, and also preferably, the noninfectious virus is FIV. A composition comprising only naturally-occurring, non-infectious virus has many applications in research and the prophylactic treatment of a viral infection. In terms of prophylactic treatment of a viral infection, the skilled artisan will appreciate the need to eliminate completely all infectious virus from the composition. If desired, further treatment of the composition comprising non-infectious particles with virus-inactivating chemicals, such as imines or psoralens, and/or pressure or heat inactivation, will further the non-infectious infectious nature of the composition. For example, an immune response-inducing amount of the present inventive composition can be administered to an animal at risk for a viral infection in order to induce an immune response. The skilled artisan will appreciate that such a composition is a significant improvement over previously disclosed compositions in that the virus is non-infectious and naturally-occurring. Thus, there is no risk of inadvertent infection, greater doses can be administered in comparison to compositions comprising infectious viral particles, and the subsequent immune response will assuredly be directed to antigens present on naturally-occurring virus. The composition comprising naturally-occurring, non-infectious virus can be administered in any manner appropriate to induce an immune response. Preferably, the virus is administered, for example, intramuscularly, mucosally, intravenously, subcutaneously, or topically. Preferably, the composition comprises naturally-occurring, non-infectious human immunodeficiency virus comprising gp120.

The composition comprising naturally-occuring, non-infectious virus can be combined with various carriers, adjuvants, diluents or other anti-viral therapeutics, if desired. Appropriate carriers include, for example, ovalbumin, albumin, globulins, hemocyanins, and the like. Adjuvants or immuno-adjuvants are incorporated in most cases to stimulate further the immune system. Any physiologically appropriate adjuvant can be used. Suitable adjuvants for inclusion in the present inventive composition include, for example, aluminum hydroxide, beryllium sulfate, silica, kaolin, carbon, bacterial endotoxin, saponin, and the like.

Thus, the present invention also provides a method of inducing an immune response to a virus in an animal. The method comprises administering to the animal an immune response-inducing amount of a composition comprising naturally-occurring, non-infectious virus as described above.

The appropriate dose of a composition comprising naturally-occuring, non-infectious virus required to induce an immune response to the virus in an animal is dependent on numerous factors, such as size of the animal and immune competency. The amount of composition administered should be sufficient to induce a humoral and/or cellular immune response. The amount of non-infectious virus in a particular composition can be determined using routine methods in the art, such as the Coulter HIV p24 antigen assay (Coulter Corp., Hialeah, Fla.). Any suitable dose of a composition comprising non-infectious virus is appropriate so long as an immune response is induced, desirably without the appearance of harmful side effects to the host. In this regard, compositions comprising from about $10^1$ to about $10^5$ particles, preferably from about $10^2$ to about $10^4$ particles, most preferably about $10^3$ particles, are suitable for inducing an immune response.

One of ordinary skill can determine the effectiveness of the composition to induce an immune response using routine methods known in the art. Cell-mediated response can be determined by employing, for example, a virus antigen-stimulated T-cell proliferation assay. The presence of a humoral immune response can be determined, for instance, with the Enzyme Linked Immunosorbent Assay (ELISA). The skilled artisan will appreciate that there are numerous other suitable assays for evaluating induction of an immune response. To the extent that a dose is inadequate to induce an appropriate immune response, "booster" administrations can subsequently be administered in order to prompt a more effective immune response.

In terms of administration of the present inventive antiviral agents or conjugates thereof, the dosage can be in unit dosage form, such as a tablet or capsule. The term "unit dosage form" as used herein refers to physically discrete units suitable as unitary dosages for human and animal subjects, each unit containing a predetermined quantity of a cyanovirin or conjugate thereof, alone or in combination with other antiviral agents, calculated in an amount sufficient to produce the desired effect in association with a pharmaceutically acceptable diluent, carrier, or vehicle.

The specifications for the unit dosage forms of the present invention depend on the particular cyanovirin, or conjugate or composition thereof, employed and the effect to be achieved, as well as the pharmacodynamics associated with each cyanovirin, or conjugate or composition thereof, in the host. The dose administered should be an "antiviral effective amount" or an amount necessary to achieve an "effective level" in the individual patient.

Since the "effective level" is used as the preferred end-point for dosing, the actual dose and schedule can vary, depending upon interindividual differences in pharmacokinetics, drug distribution, and metabolism. The "effective level" can be defined, for example, as the blood or tissue level (e.g., 0.1–1000 nM) desired in the patient that corresponds to a concentration of one or more cyanovirin or conjugate thereof, which inhibits a virus, such as HIV, in an assay known to predict for clinical antiviral activity of chemical compounds and biological agents. The "effective level" for agents of the present invention also can vary when the cyanovirin, or conjugate or composition thereof, is used in combination with AZT or other known antiviral compounds or combinations thereof.

One skilled in the art can easily determine the appropriate dose, schedule, and method of administration for the exact formulation of the composition being used, in order to achieve the desired "effective concentration" in the individual patient. One skilled in the art also can readily determine and use an appropriate indicator of the "effective concentration" of the compounds of the present invention by a direct (e.g., analytical chemical analysis) or indirect (e.g., with surrogate indicators such as p24 or RT) analysis of appropriate patient samples (e.g., blood and/or tissues).

In the treatment of some virally infected individuals, it can be desirable to utilize a "mega-dosing" regimen, wherein a large dose of the cyanovirin or conjugate thereof is administered, time is allowed for the drug to act, and then a suitable reagent is administered to the individual to inactivate the drug.

The pharmaceutical composition can contain other pharmaceuticals, in conjunction with the cyanovirin or conjugate thereof, when used to therapeutically treat a viral infection, such as that which results in AIDS. Representative examples of these additional pharmaceuticals include antiviral compounds, virucides, immunomodulators, immunostimulants, antibiotics and absorption enhancers. Exemplary antiviral compounds include AZT, ddI, ddC, gancylclovir, fluorinated dideoxynucleosides, nonnucleoside analog compounds, such as nevirapine (Shih et al., *PNAS* 88, 9878–9882, 1991), TIBO derivatives, such as R82913 (White et al., *Antiviral Res.* 16, 257–266, 1991), BI-RJ-70 (Merigan, *Am. J. Med.* 90 (Suppl.4A), 8S–17S, 1991), michellamines (Boyd et al., *J. Med. Chem.* 37,1740–1745,1994) and calanolides (Kashman et al., *J. Med. Chem.* 35, 2735–2743, 1992), nonoxynol-9, gossypol and derivatives, and gramicidin (Bourinbair et al., 1994, supra). Exemplary immunomodulators and immunostimulants include various interleukins, sCD4, cytokines, antibody preparations, blood transfusions, and cell transfusions. Exemplary antibiotics include antifungal agents, antibacterial agents, and anti-*Pneumocystitis carnii* agents. Exemplary absorption enhancers include bile salts and other surfactants, saponins, cyclodextrins, and phospholipids (Davis, 1992, supra).

Administration of a cyanovirin or conjugate thereof with other anti-retroviral agents and particularly with known RT inhibitors, such as ddC, AZT, ddI, ddA, or other inhibitors that act against other HIV proteins, such as anti-TAT agents, is expected to inhibit most or all replicative stages of the viral life cycle. The dosages of ddC and AZT used in AIDS or ARC patients have been published. A virustatic range of ddC is generally between 0.05 μM to 1.0 μM. A range of about 0.005–0.25 mg/kg body weight is virustatic in most patients. The preliminary dose ranges for oral administration are somewhat broader, for example 0.001 to 0.25 mg/kg given in one or more doses at intervals of 2, 4, 6, 8, 12, etc. hours. Currently, 0.01 mg/kg body weight ddC given every 8 hrs is preferred. When given in combined therapy, the other antiviral compound, for example, can be given at the same time as the cyanovirin or conjugate thereof or the dosing can be staggered as desired. The two drugs also can be combined in a composition. Doses of each can be less when used in combination than when either is used alone.

It will also be appreciated by one skilled in the art that a DNA sequence of a cyanovirin or conjugate thereof of the present invention can be inserted ex vivo into mammalian cells previously removed from a given animal, in particular a human, host. Such cells can be employed to express the corresponding cyanovirin or conjugate in vivo after reintroduction into the host. Feasibility of such a therapeutic strategy to deliver a therapeutic amount of an agent in close proximity to the desired target cells and pathogens, i.e., virus, more particularly retrovirus, specifically HIV and its envelope glycoprotein gp120, has been demonstrated in studies with cells engineered ex vivo to express sCD4 (Morgan et al., 1994, supra). It is also possible that, as an alternative to ex vivo insertion of the DNA sequences of the present invention, such sequences can be inserted into cells directly in vivo, such as by use of an appropriate viral vector. Such cells transfected in vivo are expected to produce antiviral amounts of cyanovirin or a conjugate thereof directly in vivo.

Given the present disclosure, it will be additionally appreciated that a DNA sequence corresponding to a cyanovirin or conjugate thereof can be inserted into suitable nonmammalian host cells, and that such host cells will express therapeutic or prophylactic amounts of a cyanovirin or conjugate thereof directly in vivo within a desired body compartment of an animal, in particular a human. Example 3 illustrates the transformation and expression of effective virucidal amounts of a cyanovirin in a non-mammalian cell, more specifically a bacterial cell. Example 10 illustrates the transformation and expression of a cyanovirin in a non-mammalian cell, specifically a yeast cell. If a yeast cell is to be transformed, desirably the cyanovirin is nonglycosylated or rendered glycosylation-resistant as described above.

In a preferred embodiment of the present invention, a method of female-contollable prophylaxis against HIV infection comprises the intravaginal administration and/or establishment of, in a female human, a persistent intravaginal population of lactobacilli that have been transformed with a coding sequence of the present invention to produce, over a prolonged time, effective virucidal levels of a cyanovirin or conjugate thereof, directly on or within the vaginal and/or cervical and/or uterine mucosa. It is noteworthy that both the World Health Organization (WHO), as well as the U.S. National Institute of Allergy and Infectious Diseases, have pointed to the need for development of female-controlled topical microbicides, suitable for blocking the transmission of HIV, as an urgent global priority (Lange et al., *Lancet* 341, 1356, 1993; Fauci, *NIAID News*, Apr. 27, 1995). A composition comprising a present inventive antiviral agent and a solid-support matrix is particularly useful in this regard, particularly when the solid-support matrix is a contraceptive device, such as a condom, a diaphragm, a cervical cap, a vaginal ring, or a sponge.

The present invention also provides antibodies directed to the proteins of the present invention. The availability of antibodies to any given protein is highly advantageous, as it provides the basis for a wide variety of qualitative and quantitative analytical methods, separation and purification methods, and other useful applications directed to the subject proteins. Accordingly, given the present disclosure and the proteins of the present invention, it will be readily apparent to one skilled in the art that antibodies, in particular antibodies specifically binding to a protein of the present invention, can be prepared using well-established methodologies (e.g., such as the methodologies described in detail by Harlow and Lane, in *Antibodies. A Laboratory Manual,* Cold Spring Harbor Laboratory, Cold Spring Harbor, 1988, pp. 1–725). Such antibodies can comprise both polyclonal and monoclonal antibodies. Furthermore, such antibodies can be obtained and employed either in solution-phase or coupled to a desired solid-phase matrix, such as magnetic beads or a flow through matrix. Having in hand such antibodies as provided by the present invention, one skilled in the art will further appreciate that such antibodies, in conjunction with well-established procedures (e.g., such as described by Harlow and Lane (1988, supra) comprise useful methods for the detection, quantification, or purification of a cyanovirin, conjugate thereof, or host cell transformed to produce a cyanovirin or conjugate thereof. Example 12 further illustrates an antibody specifically binding a cyanovirin.

Matrix-anchored anti-cyanovirin antibodies also can be used in a method to remove virus in a sample. Preferably, the antibody binds to an epitope of an antiviral protein or an antiviral peptide comprising at least nine contiguous amino acids of SEQ ID NO: 2. Preferably, the matrix is a solid support matrix, such as a magnetic bead or a flow-through matrix. If the solid support matrix to which the anti-cyanovirin antibody is attached comprises magnetic beads, removal of the antibody-cyanovirin-virus complex can be readily accomplished using a magnet.

In view of the above, the present invention provides a method of removing virus from a sample. The method comprises (a) contacting the sample with a composition comprising an isolated and purified antiviral protein, antiviral peptide, antiviral protein conjugate or antiviral peptide conjugate, wherein (i) the antiviral protein or the antiviral peptide comprises at least nine contiguous amino acids of SEQ ID NO: 2, and (ii) the at least nine contiguous amino acids bind to the virus, and (b) contacting the sample with an anti-cyanovirin antibody attached to a solid support matrix, whereupon the anti-cyanovirin antibody binds to the antiviral peptide, antiviral protein, antiviral peptide conjugate or antiviral protein conjugate to which is bound the virus, and (c) separating the solid support matrix from the sample, whereupon the virus is removed from the sample. Preferably, the antiviral protein comprises SEQ ID NO: 2. Desirably, the virus that is removed is infectious, such as HIV. The sample can be blood, a component of blood, sperm, cells, tissue or an organ.

The antibody for use in the aforementioned method is an antibody that binds to a protein or a peptide comprising at least nine contiguous amino acids of SEQ ID NO: 2, and, which protein or peptide can bind to and inactivate a virus. The antibody can be coupled to the solid support matrix using similar methods and with similar considerations as described above for attaching a cyanovirin to a solid support matrix. For example, coupling methods and molecules employed to attach an anti-cyanovirin antibody to a solid support matrix, such as magnetic beads or a flow-through matrix, can employ biotin/streptavidin coupling or coupling through molecules, such as polyethylene glycol, albumin or dextran. For instance, essentially the same procedure as described in Example 7 for attaching a cyanovirin to a solid support matrix comprising magnetic beads can be used to attach an anti-cyanovirin antibody to magnetic beads. Also analogously, it can be shown that, after such coupling, the matrix-anchored anti-cyanovirin antibody retains its ability to bind to a protein or a peptide comprising at least nine contiguous amino acids of SEQ ID NO:2, which protein or peptide can bind to and inactivate a virus.

The present inventive cyanovirins, conjugates, host cells, antibodies, compositions and methods are further described in the context of the following examples. These examples serve to illustrate further the present invention and are not intended to limit the scope of the invention.

EXAMPLES

Example 1

This example shows details of anti-HIV bioassay-guided isolation and elucidation of pure cyanovirin from aqueous extracts of the cultured cyanobacterium, *Nostoc ellipsosporum*.

The method described in Weislow et al. (1989, supra) was used to monitor and direct the isolation and purification process. Cyanobacterial culture conditions, media and classification were as described previously (Patterson, *J. Phycol.* 27, 530–536, 1991). Briefly, the cellular mass from a unialgal strain of *Nostoc ellipsosporum* (culture Q68D170) was harvested by filtration, freeze-dried and extracted with MeOH—$CH_2Cl_2$ (1:1) followed by $H_2O$. Bioassay indicated that only the $H_2O$ extract contained HIV-inhibitory activity. A solution of the aqueous extract (30 mg/ml) was treated by addition of an equal volume of ethanol (EtOH). The resulting 1:1 $H_2O$-EtOH solution was kept at −20° C. for 15 hrs. Then, the solution was centrifuged to remove precipitated materials (presumably, high molecular weight biopolymers). The resulting HIV-inhibitory supernatant was evaporated, then fractionated by reverse-phase vacuum-liquid chromatography (Coll et al., *J. Nat, Prod.* 49, 934–936, 1986; and Pelletier et al., *J. Nat, Prod.* 49, 892–900, 1986) on widepore $C_4$ packing (300, BakerBond WP-$C_4$), and eluted with increasing concentrations of methanol (MeOH) in $H_2O$. Anti-HIV activity was concentrated in the material eluted with MeOH—$H_2O$ (2:1). SDS-PAGE analysis of this fraction showed one main protein band, with a relative molecular mass (Mr) of approximately 10 kDa. Final purification was achieved by repeated reverse-phase HPLC on 1.9×15 cm μBondapak $C_{18}$ (Waters Associates) columns eluted with a gradient of increasing concentration of acetonitrile in $H_2O$. The mobile phase contained 0.05% (v/v) TFA, pH=2. Eluted proteins and peptides were detected by UV absorption at 206, 280 and 294 nm with a rapid spectral detector (Pharmacia LKB model 2140). Individual fractions were collected, pooled based on the UV chromatogram, and lyophilized. Pooled HPLC fractions were subjected to SDS-PAGE under reducing conditions (Laemnuli, *Nature* 227, 680–685, 1970), conventional amino acid analysis, and testing for anti-HIV activity.

Figure 1C:
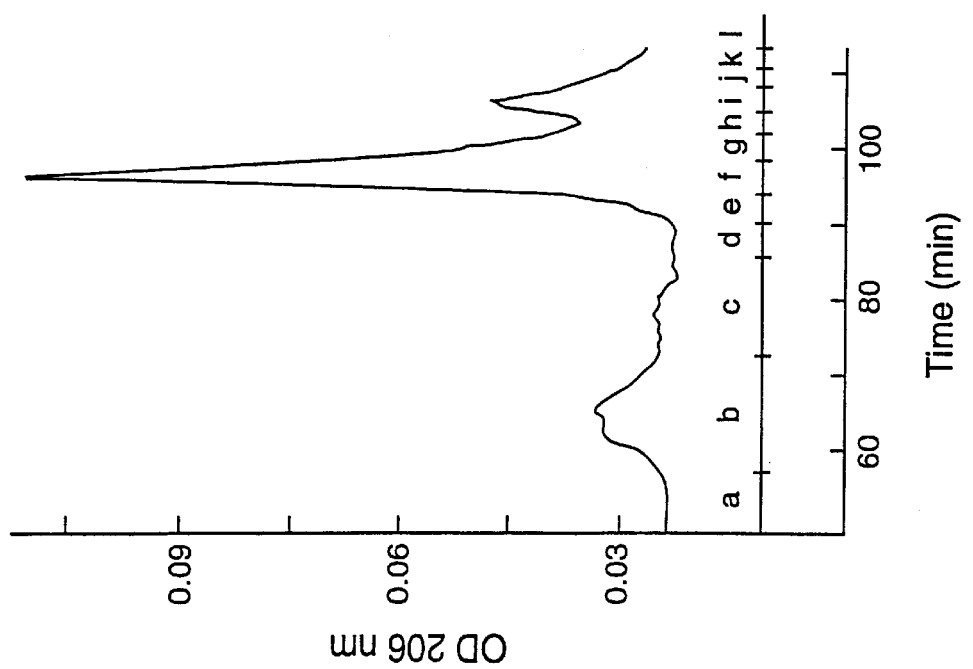
FIG. 1C is a graph of OD (206) nm versus time (min), which represents an HPLC chromatogram of reduced cyanovirin.

FIG. 1A is a graph of OD 206 nm versus time (min), which shows the μBondapak $C_{18}$ HPLC chromatogram of nonreduced cyanovirin eluted with a linear $CH_3CN/H_2O$ gradient (buffered with 0.05% TFA) from 28–38% $CH_3CN$. FIG. 1C is a graph of OD 206 nm versus time (min), which shows the chromatogram of cyanovirin that was first reduced with β-mercaptoethanol and then separated under identical HPLC conditions. HPLC fractions from the two runs were collected as indicated. 10% aliquots of each fraction were lyophilized, made up in 100 μl 3:1 $H_2O$ DMSO and assessed for anti-HIV activity in the XTT assay. FIG. 1B is a bar graph of maximum dilution for 50% protection versus HPLC fraction, which illustrates the maximum dilution of each fraction that provided 50% protection from the cytopathic effects of HIV infection for the nonreduced cyanovirin HPLC fractions. Corresponding anti-HIV results for the HPLC fractions from reduced cyanovirin are shown in FIG. 1D, which is a bar graph of maximum dilution for 50% protection versus HPLC fraction. 20% aliquots of selected HPLC fractions were analyzed by SDS-PAGE. In the initial HPLC separation, using a linear gradient from 30–50% $CH_3CN$, the anti-HIV activity coeluted with the principal UV-absorbing peak at approximately 33% $CH_3CN$. Fractions corresponding to the active peak were pooled and split into two aliquots.

Reinjection of the first aliquot under similar HPLC conditions, but with a linear gradient from 28–38% $CH_3CN$, resolved the active material into two closely eluting peaks at 33.4 and 34.0% $CH_3CN$. The anti-HIV activity profile of the fractions collected during this HPLC run (as shown in FIG. 1B) corresponded with the two UV peaks (as shown in FIG. 1A). SDS-PAGE of fractions collected under the individual peaks showed only a single protein band.

The second aliquot from the original HPLC separation was reduced with β-mercaptoethanol prior to reinjection on the HPLC. Using an identical 28–38% gradient, the reduced material gave one principal peak (as shown in FIG. 1C) that eluted later in the run with 36.8% $CH_3CN$. Only a trace of anti-HIV activity was detected in the HPLC fractions from the reduced material (as shown in FIG. 1D).

The two closely eluting HPLC peaks of the nonreduced material (FIG. 1A) gave only one identical band on SDS-PAGE (run under reducing conditions), and reduction with β-mercaptoethanol resulted in an HPLC peak with a longer retention time than either of the nonreduced peaks. This indicated that disulfides were present in the native protein. Amino acid analysis of the two active peaks showed they had virtually identical compositions. It is possible that the two HPLC peaks resulted from cis/trans isomerism about a proline residue or from microheterogeneity in the protein sample that was not detected in either the amino acid analysis or during sequencing. The material collected as the two HIV-inhibitory peaks was combined for further analyses and was given the name cyanovirin-N.

Example 2

This example illustrates synthesis of cyanovirin genes.

The chemically deduced amino acid sequence of cyanovirin-N was back-translated to obtain a DNA coding sequence. In order to facilitate initial production and purification of recombinant cyanovirin-N, a commercial expression vector (PFLAG-1, from International Biotechnologies, Inc., New Haven, Conn.), for which reagents were available for affinity purification and detection, was selected. Appropriate restriction sites for ligation to pFLAG-1, and a stop codon, were included in the DNA sequence. FIG. 2 is an example of a DNA sequence encoding a synthetic cyanovirin gene. This DNA sequence design couples the cyanovirin-N coding region to codons for a "FLAG" octapeptide at the N-terminal end of cyanovirin, providing for production of a FLAG-cyanovirin fusion protein.

Figure 11:
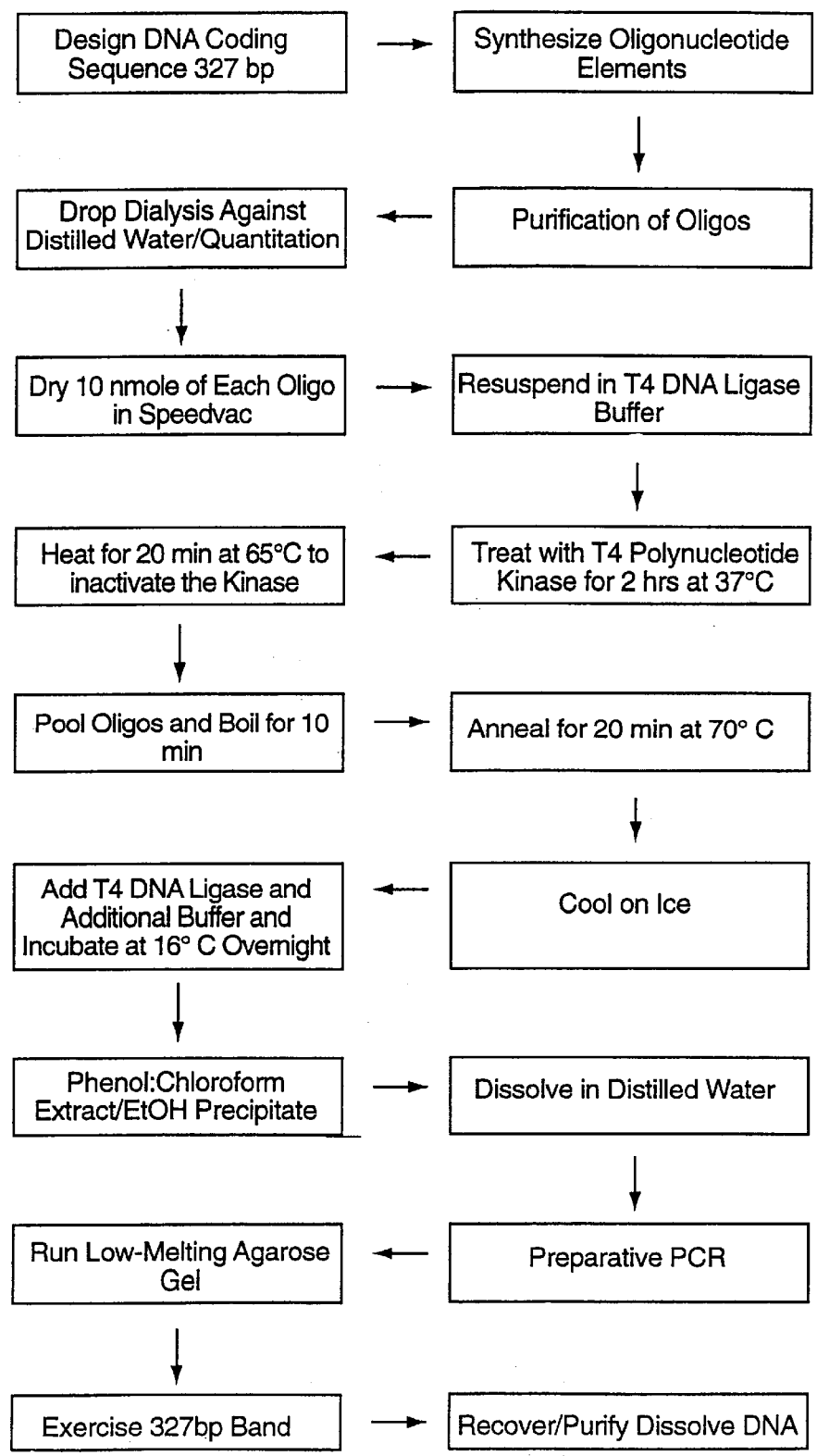
FIG. 11 is a flowchart of the synthesis of a cyanovirin gene.
Figure 12:
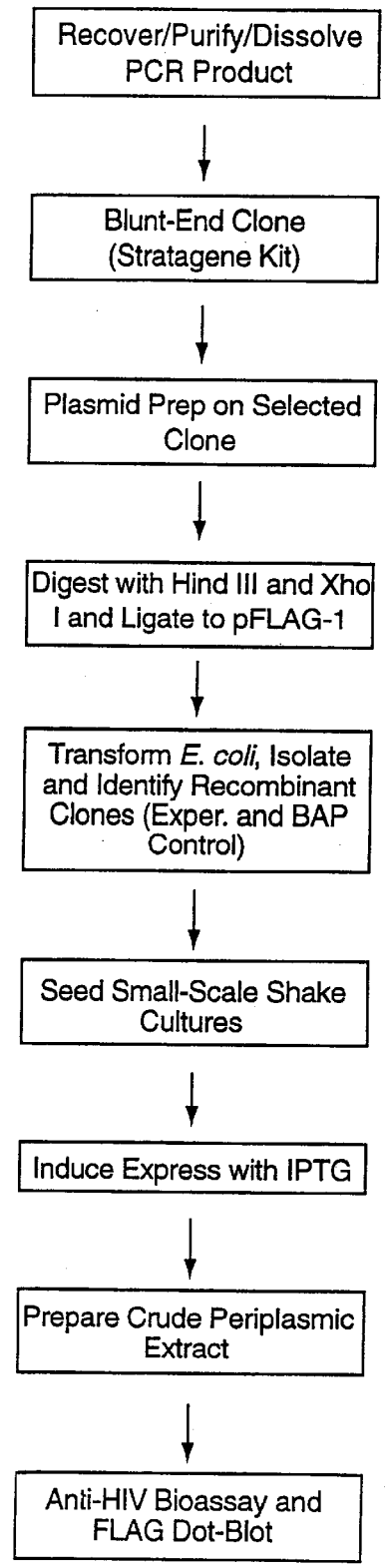
FIG. 12 is a flowchart of the expression of synthetic cyanovirin.

A flowchart for synthesis of this DNA sequence is shown in FIG. 11. The DNA sequence was synthesized as 13 overlapping, complementary oligonucleotides and assembled to form the double-stranded coding sequence. Oligonucleotide elements of the synthetic DNA coding sequence were synthesized using a dual-column nucleic acid synthesizer (Model 392, Applied Biosystems Inc., Foster City, Calif.). Completed oligonucleotides were cleaved from the columns and deprotected by incubation overnight at 56° C in concentrated ammonium hydroxide. Prior to treatment with T4 polynucleotide kinase, 33–66 mers were drop-dialyzed against distilled water. The 13 oligonucleotide preparations were individually purified by HPLC, and 10 nmole quantities of each were ligated with T4 DNA ligase into a 327 bp double-stranded DNA sequence. DNA was recovered and purified from the reaction buffer by phenol:chloroform extraction, ethanol precipitation, and further washing with ethanol. Individual oligonucleotide preparations were pooled and boiled for 10 min to ensure denaturation. The temperature of the mixture was then reduced to 70° C. for annealing of the complementary strands. After 20 min, the tube was cooled on ice and 2,000 units of T4 DNA ligase were added together with additional ligase buffer. Ligation was performed overnight at 16° C. DNA was recovered and purified from the ligation reaction mixture by phenol:chloroform extraction and ethanol precipitation and washing.

The purified, double-stranded synthetic DNA was then used as a template in a polymerase chain reaction (PCR). One $\mu$l of the DNA solution obtained after purification of the ligation reaction mixture was used as a template. Thermal cycling was performed using a Perkin-Elmer instrument. “Vent” thermostable DNA polymerase, restriction enzymes, T4 DNA ligase and polynucleotide kinase were obtained from New England Biolabs, Beverly, Mass. Vent polymerase was selected for this application because of its claimed superiority in fidelity compared to the usual Taq enzyme. The PCR reaction product was run on a 2% agarose gel in TBE buffer. The 327 bp construct was then cut from the gel and purified by electroelution. Because it was found to be relatively resistant to digestion with Hind III and Xho I restriction enzymes, it was initially cloned using the pCR-Script system (Stratagene). Digestion of a plasmid preparation from one of these clones yielded the coding sequence, which was then ligated into the multicloning site of the pFLAG-1 vector.

*E. coli* were transformed with the pFLAG-construct and recombinant clones were identified by analysis of restriction digests of plasmid DNA. Sequence analysis of one of these selected clones indicated that four bases deviated from the intended coding sequence. This included deletion of three bases coding for one of four cysteine residues contained in the protein and an alteration of the third base in the preceding codon (indicated by the boxes in FIG. 2). In order to correct these “mutations,” which presumably arose during the PCR amplification of the synthetic template, a double-stranded “patch” was synthesized, which could be ligated into restriction sites flanking the mutations (these Bst XI and Esp1 sites are also indicated in FIG. 2). The patch was applied and the repair was confirmed by DNA sequence analysis.

For preparation of a DNA sequence coding for native cyanovirin, the aforementioned FLAG-cyanovirin construct was subjected to site-directed mutagenesis to eliminate the codons for the FLAG octapeptide and, at the same time, to eliminate a unique Hind III restriction site. This procedure is illustrated in FIG. 3, which illustrates a site-directed mutagenesis maneuver used to eliminate codons for a FLAG octapeptide and a Hind III restriction site from the sequence of FIG. 2. A mutagenic oligonucleotide primer was synthesized, which included portions of the codons for the Omp secretory peptide and cyanovirin, but lacking the codons for the FLAG peptide. Annealing of this mutagenic primer, with creation of a DNA hairpin in the template strand, and extension by DNA polymerase resulted in generation of new plasmid DNA lacking both the FLAG codon sequence and the Hind III site (refer to FIG. 2 for details). Digestion of plasmid DNA with Hind III resulted in linearization of “wild-type” strands but not “mutant” strands. Since transformation of *E. coli* occurs more efficiently with circular DNA, clones could be readily selected which had the revised coding sequence which specified production of native cyanovirin-N directly behind the Omp secretory peptide. DNA sequencing verified the presence of the intended sequence. Site-directed mutagenesis reactions were carried out using materials (polymerase, buffers, etc.) obtained from Pharmacia Biotech, Inc., Piscataway, N.J.

Example 3

This example illustrates expression of synthetic cyanovirin genes.

*E. coli* (strain DH5$\alpha$) were transformed (by electroporation) with the pFLAG-1 vector containing the coding sequence for the FLAG-cyanovirin-N fusion protein (see FIG. 2 for details of the DNA sequence). Selected clones were seeded into small-scale shake flasks containing (LB) growth medium with 100 $\mu$g/ml ampicillin and expanded by incubation at 37° C. Larger-scale Erlenmeyer flasks (0.5–3.0 liters) were then seeded and allowed to grow to a density of 0.5–0.7 $OD_{600}$ units. Expression of the FLAG-cyanovirin-N fusion protein was then induced by adding IPTG to a final concentration of 1.7 mM and continuing incubation at 30° C. for 3–6 hrs. For harvesting of periplasmic proteins, bacteria were pelleted, washed, and then osmotically shocked by treatment with sucrose, followed by resuspension in distilled water. Periplasmic proteins were obtained by sedimenting the bacteria and then filtering the aqueous supernatant through Whatman paper. Crude periplasmic extracts showed both anti-HIV activity and presence of a FLAG-cyanovirin-N fusion protein by Western or spot-blotting.

The construct for native cyanovirin-N described in Example 2 was used to transform bacteria in the same manner as described above for the FLAG-cyanovirin-N fusion protein. Cloning, expansion, induction with IPTG, and harvesting were performed similarly. Crude periplasmic extracts showed strong anti-HIV activity on bioassay. A flowchart of the expression of synthetic cyanovirin genes is shown in FIG. 12.

Example 4

This example illustrates purification of recombinant cyanovirin proteins.

Using an affinity column based on an anti-FLAG monoclonal antibody (International Biotechnologies, Inc., New Haven, Conn.), FLAG-cyanovirin-N fusion protein could be purified as follows.

The respective periplasmic extract, prepared as described in Example 3, was loaded onto 2–20 ml gravity columns containing affinity matrix and washed extensively with PBS containing $CA^{++}$ to remove contaminating proteins. Since the binding of the FLAG peptide to the antibody is $Ca^{++}$-dependent, fusion protein could be eluted by passage of EDTA through the column. Column fractions and wash volumes were monitored by spot-blot analysis using the same anti-FLAG antibody. Fractions containing fusion protein were then pooled, dialyzed extensively against distilled water, and lyophilized.

Figure 4:
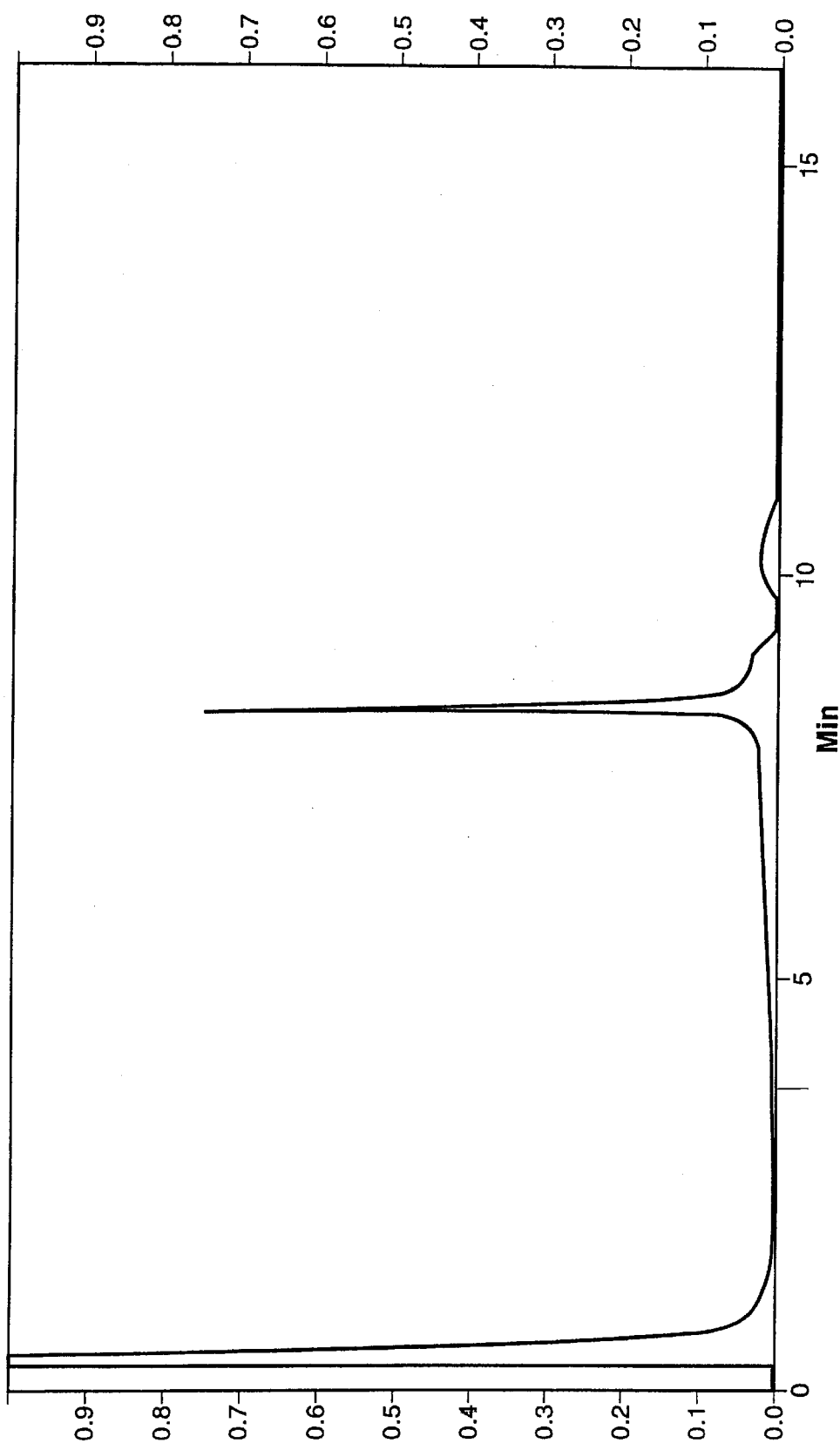
FIG. 4 shows a typical HPLC chromatogram during the purification of a recombinant native cyanovirin.

For purification of recombinant native cyanovirin-N, the corresponding periplasmic extract from Example 3 was subjected to step-gradient $C_4$ reverse-phase, vacuum-liquid chromatography to give three fractions: (1) eluted with 100% $H_2O$, (2) eluted with MeOH-$H_2O$ (2:1), and (3) eluted with 100% MeOH. The anti-HIV activity was concentrated in fraction (2). Purification of the recombinant cyanovirin-N was performed by HPLC on a 1.9×15 cm μBondapak (Waters Associates) $C_{18}$ column eluted with a gradient of increasing concentration of $CH_3CN$ in $H_2O$ (0.05% TFA, v/v in the mobile phase). A chromatogram of the final HPLC purification on a 1×10 cm (Cohensive Technologies, Inc.) $C_4$ column monitored at 280 nm is shown in FIG. 4, which is typical HPLC chromatogram during the purification of a recombinant native cyanovirin. Gradient elution, 5 ml/min, from 100% $H_2O$ to $H_2O$—$CH_3CN$ (7:3) was carried out over 23 min with 0.05% TFA (v/v) in the mobile phase.

Example 5

This example shows anti-HIV activities of natural and recombinant cyanovirin-N and FLAG-cyanovirin-N.

Pure proteins were initially evaluated for antiviral activity using an XTT-tetrazolium anti-HIV assay described previously (Boyd, in *AIDS, Etiology, Diagnosis, Treatment and Prevention*, 1988, supra; Gustafson et al., *J. Med. Chem.* 35, 1978–1986, 1992; Weislow, 1989, supra; and Gulakowski, 1991, supra). The CEM-SS human lymphocytic target cell line used in all assays was maintained in RPMI 1650 medium (Gibco, Grand Island, N.Y.), without phenol red, and was supplemented with 5% fetal bovine serum, 2 mM L-glutamine, and 50 μg/ml gentamicin (complete medium).

Exponentially growing cells were pelleted and resuspended at a concentration of $2.0×10^5$ cells/ml in complete medium. The Haitian variant of HIV, HTLV-III$_{RF}$ ($3.54×10^6$ SFU/ml), was used throughout. Frozen virus stock solutions were thawed immediately before use and resuspended in complete medium to yield $1.2×12^5$ SFU/ml. The appropriate amounts of the pure proteins for anti-HIV evaluations were dissolved in $H_2O$-DMSO (3:1), then diluted in complete medium to the desired initial concentration. All serial drug dilutions, reagent additions, and plate-to-plate transfers were carried out with an automated Biomek 1000 Workstation (Beckman Instruments, Palo Alto, Calif.).

Figure 5A:
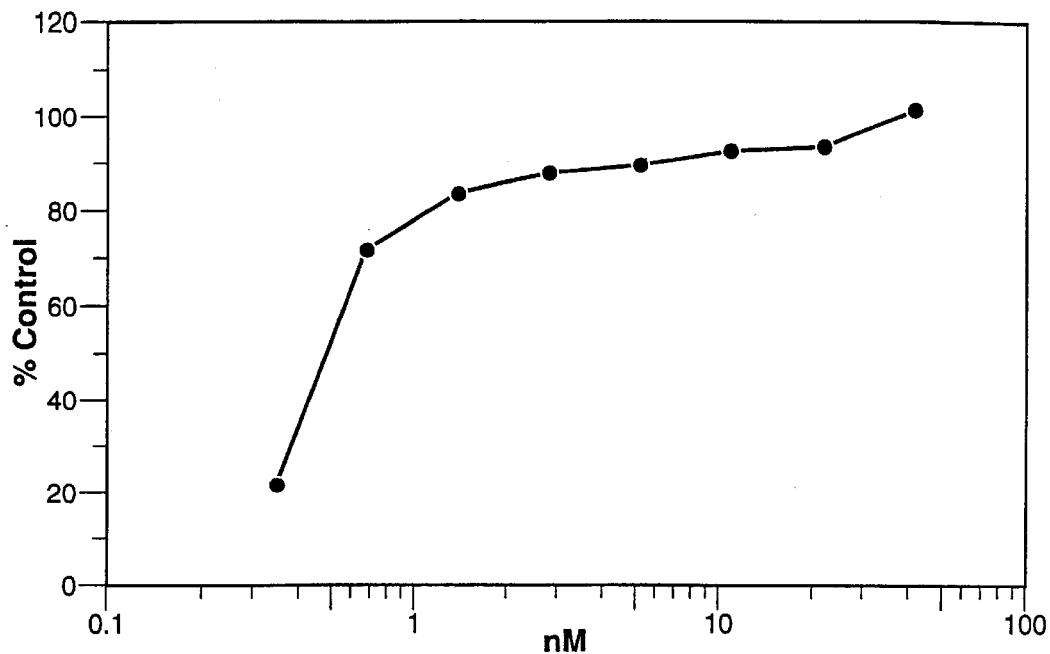
FIG. 5A is a graph of % control versus concentration (nM), which illustrates the antiviral activity of native cyanovirin from *Nostoc ellipsosporum*.
Figure 5B:
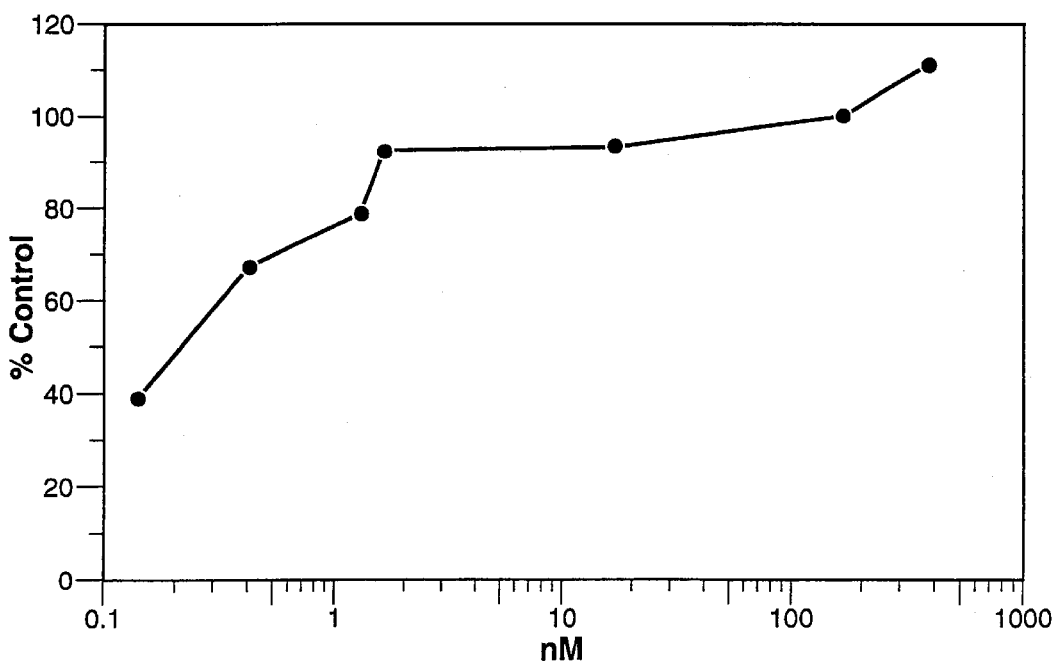
FIG. 5B is a graph of % control versus concentration (nM), which illustrates the antiviral activity of recombinant cyanovirin.
Figure 5C:
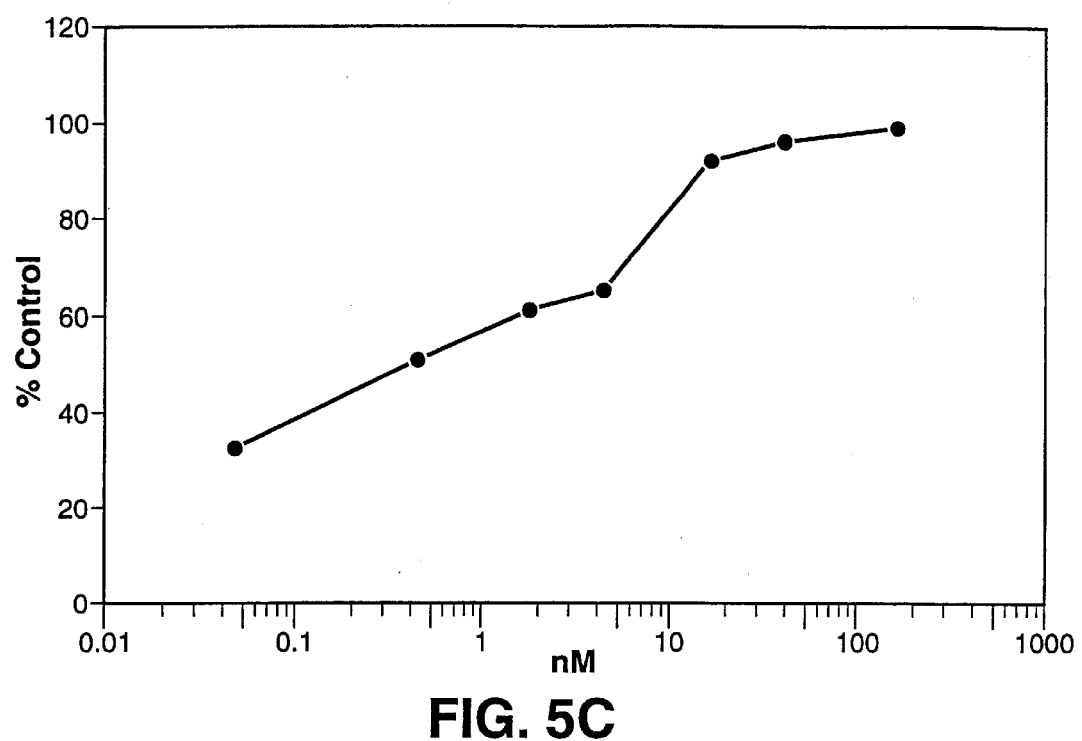
FIG. 5C is a graph of % control versus concentration (nM), which illustrates the antiviral activity of recombinant FLAG-fusion cyanovirin.
Figure 6A:
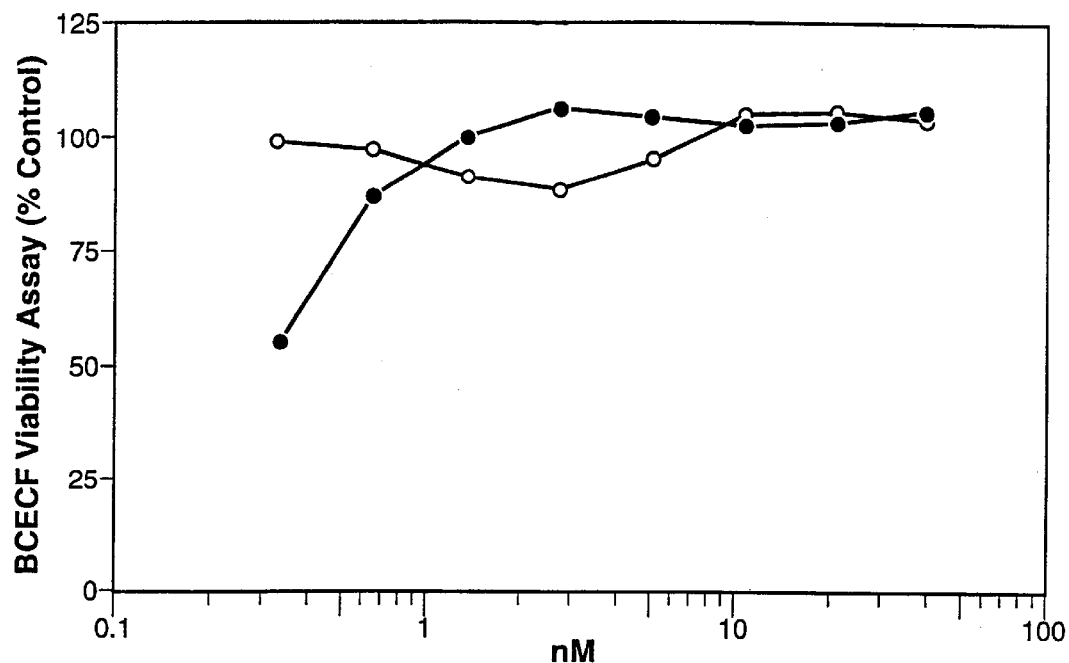
FIG. 6A is a graph of % control versus concentration (nM), which depicts the relative numbers of viable CEM-SS cells infected with HIV-1 in a BCECF assay.
Figure 6B:
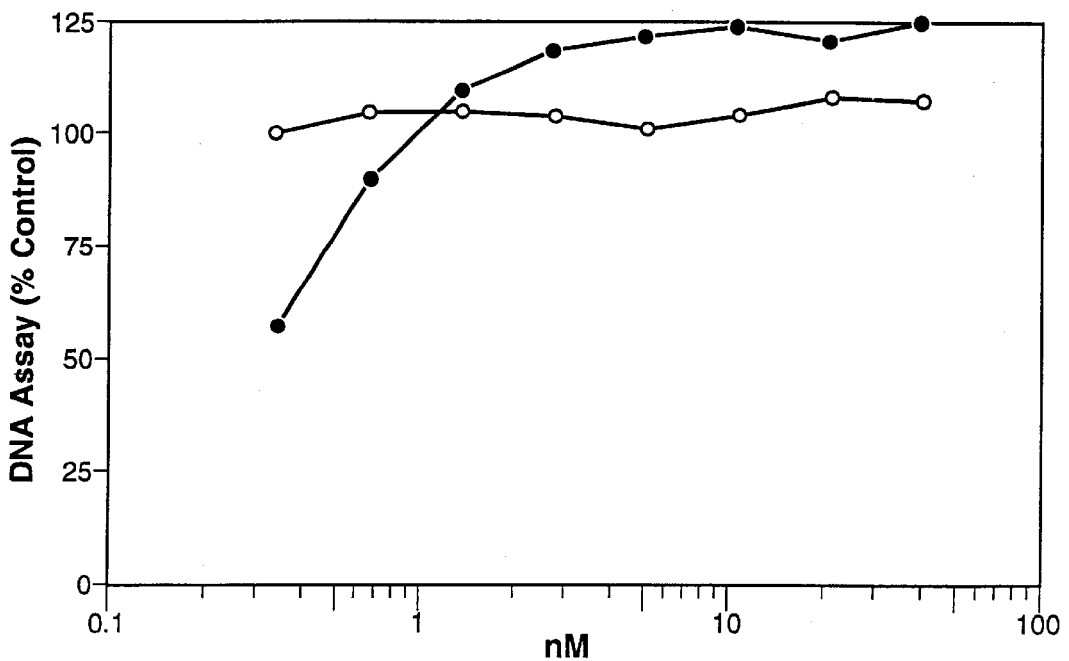
FIG. 6B is a graph of % control versus concentration (nM), which depicts the relative DNA contents of CEM-SS cell cultures infected with HIV-1.
Figure 6C:
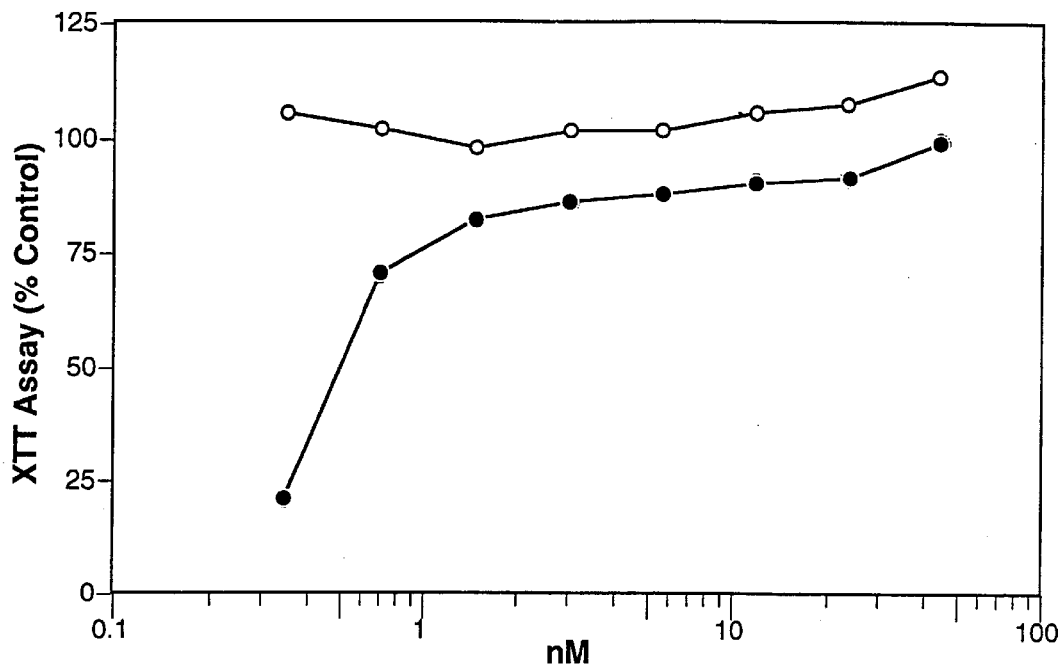
FIG. 6C is a graph of % control versus concentration (nM), which depicts the relative numbers of viable CEM-SS cells infected with HIV-1 in an XTT assay.
Figure 6D:
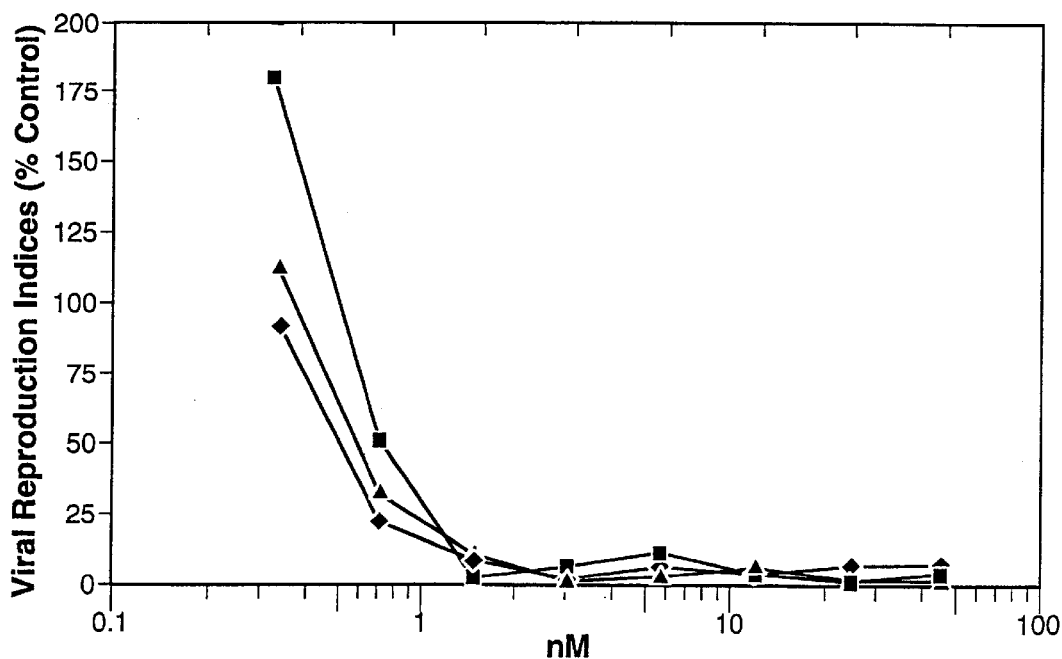
FIG. 6D is a graph of % control versus concentration (nM), which depicts the effect of a range of concentration of cyanovirin upon indices of infectious virus or viral replication.

FIGS. 5A–5C are graphs of % control versus concentration (nm), which illustrate antiviral activities of native cyanovirin from *Nostoc ellipsosporum* (A), recombinant native (B), and recombinant FLAG-fusion (C) cyanovirins. The graphs show the effects of a range of concentrations of the respective cyanovirins upon CEM-SS cells infected with HIV-1 (•),as determined after 6 days in culture. Data points represent the percent of the respective uninfected, nondrug-treated control values. All three cyanovirins showed potent anti-HIV activity, with an $EC_{50}$ in the low nanomolar range and no significant evidence of direct cytotoxicity to the host cells at the highest tested concentrations (up to 1.2 μM).

As an example of a further demonstration of the anti-HIV activity of pure cyanovirin-N, a battery of interrelated anti-HIV assays was performed in individual wells of 96-well microtiter plates, using methods described in detail elsewhere (Gulakowski, 1991, supra). Briefly, the procedure was as follows. Cyanovirin solutions were serially diluted in complete medium and added to 96-well test plates. Uninfected CEM-SS cells were plated at a density of $1×10^4$ cells in 50 μl of complete medium. Diluted HIV-1 was then added to appropriate wells in a volume of 50 μl to yield a multiplicity of infection of 0.6. Appropriate cell, virus, and drug controls were incorporated in each experiment. The final volume in each microtiter well was 200 μl. Quadruplicate wells were used for virus-infected cells. Plates were incubated at 37° C. in an atmosphere containing 5% $CO_2$ for 4, 5, or 6 days.

Subsequently, aliquots of cell-free supernatant were removed from each well using the Biomek, and analyzed for reverse transcriptase activity, p24 antigen production, and synthesis of infectious virions as described (Gulakowski, 1991, supra). Cellular growth or viability then was estimated on the remaining contents of each well using the XTT (Weislow et al., 1989, supra), BCECF (Rink et al., *J. Cell Biol.* 95, 189–196, 1982), and DAPI (McCaffrey et al., *In Vitro Cell Develop. Biol.* 24, 247–252, 1988) assays as described (Gulakowski et al., 1991, supra). To facilitate graphical displays and comparisons of data, the individual experimental assay results (of at least quadruplicate determinations of each) were averaged, and the mean values were used to calculate percentages in reference to the appropriate controls. Standard errors of the mean values used in these calculations typically averaged less than 10% of the respective mean values.

FIGS. 6A–6D are graphs of % control versus concentration (nm), which illustrate anti-HIV activity of a cyanovirin in a multiparameter assay format. Graphs 6A, 6B, and 6C show the effects of a range of concentrations of cyanovirin upon uninfected CEM-SS cells (○), and upon CEM-SS cells infected with HIV-1 (●), as determined after 6 days in culture. Graph 6A depicts the relative numbers of viable CEM-SS cells, as assessed by the BCECF assay. Graph 6B depicts the relative DNA contents of the respective cultures. Graph 6C depicts the relative numbers of viable CEM-SS cells, as assessed by the XTT assay. Graph 6D shows the effects of a range of concentrations of cyanovirin upon indices of infectious virus or viral replication as determined after 4 days in culture. These indices include viral reverse transcriptase (▲), viral core protein p24 (♦), and syncytium-forming units (■). In graphs 6A, 6B, and 6C, the data are represented as the percent of the uninfected, nondrug-treated control values. In graph 6D the data are represented as the percent of the infected, nondrug-treated control values.

As illustrated in FIG. 6, cyanovirin-N was capable of complete inhibition of the cytopathic effects of HIV-1 upon CEM-SS human lymphoblastoid target cells in vitro; direct cytotoxicity of the protein upon the target cells was not observed at the highest tested concentrations. Cyanovirin-N also strikingly inhibited the production of RT, p24, and SFU in HIV-1-infected CEM-SS cells within these same inhibitory effective concentrations, indicating that the protein halted viral replication.

The anti-HIV activity of the cyanovirins is extremely resilient to harsh environmental challenges. For example, unbuffered cyanovirin-N solutions withstood repeated freeze-thaw cycles or dissolution in organic solvents (up to 100% DMSO, MeOH, or $CH_3CN$) with no loss of activity. Cyanovirin-N tolerated detergent (0.1% SDS), high salt (6 M guanidine HCl) and heat treatment (boiling, 10 min in $H_2O$) with no significant loss of HIV inhibitory activity. Reduction of the disulfides with β-mercaptoethanol, followed immediately by $C_{18}$ HPLC purification, drastically reduced the cytoprotective activity of cyanovirin-N. However, solutions of reduced cyanovirin-N regained anti-HIV inhibitory activity during prolonged storage. When cyanovirin-N was reduced (□mercaptoethanol, 6 M guanidine HCl, pH 8.0) but not put through $C_{18}$ HPLC, and, instead, simply desalted, reconstituted and assayed, it retained virtually full activity.

Example 6

This example illustrates that the HIV viral envelope gp120 is a principal molecular target of cyanovirin-N.

Figure 7:
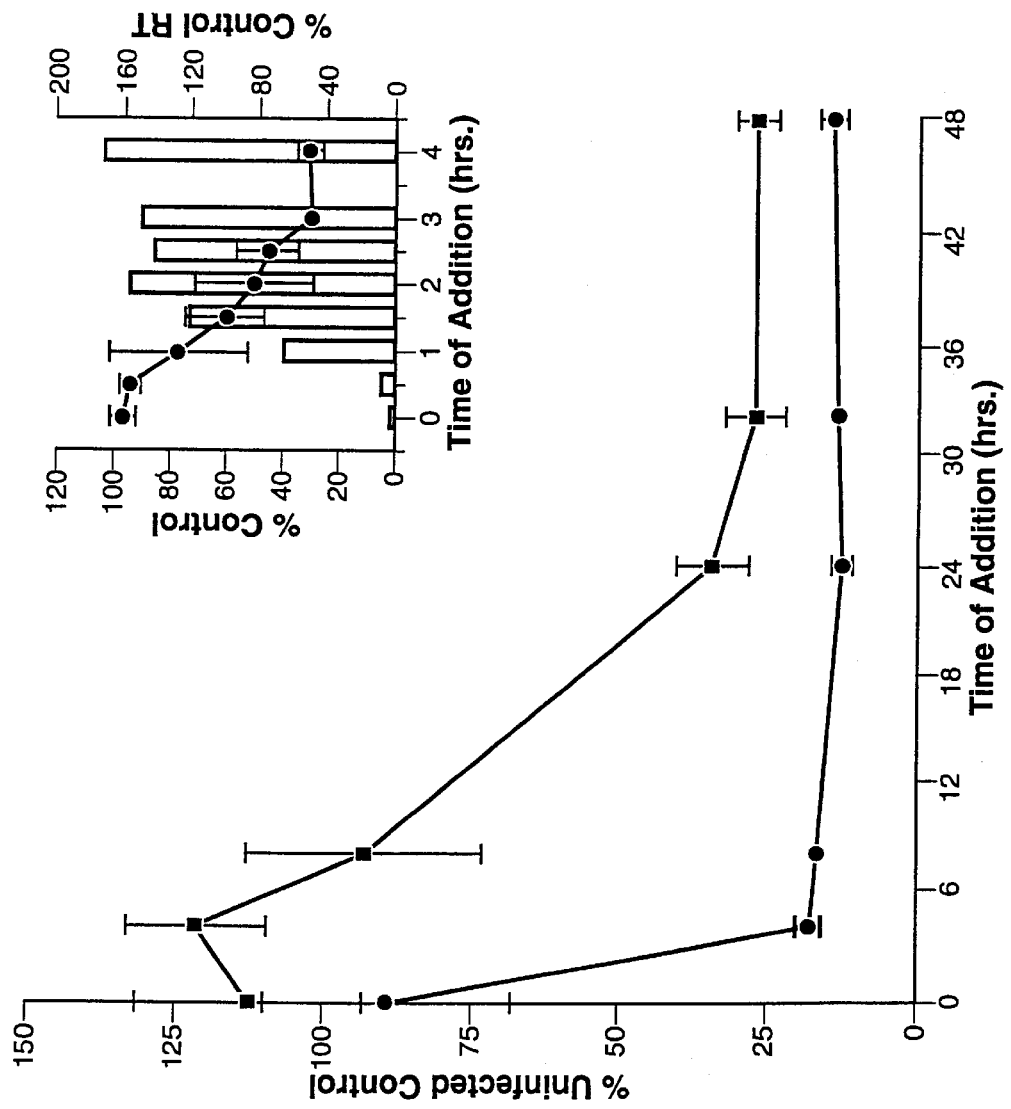
FIG. 7 is a graph of % uninfected control versus time of addition (hrs), which shows results of time-of-addition studies of a cyanovirin, showing anti-HIV activity in CEM-SS cells infected with HIV-$1_{RF}$.

Initial experiments, employing the XTT-tetrazolium assay (Weislow et al., 1989, supra), revealed that host cells preincubated with cyanovirin (10 nM, 1 hr), then centrifuged free of cyanovirin-N, retained normal susceptibility to HIV infection; in contrast, the infectivity of concentrated virus similarly pretreated, then diluted to yield non-inhibitory concentrations of cyanovirin-N, was essentially abolished. This indicated that cyanovirin-N was acting directly upon the virus itself, i.e., acting as a direct "virucidal" agent to prevent viral infectivity even before it could enter the host cells. This was further confirmed in time-of-addition experiments, likewise employing the XTT-tetrazolium assay (Weislow, 1989, supra), which showed that, to afford maximum antiviral activity, cyanovirin-N had to be added to cells before or as soon as possible after addition of virus as shown in FIG. 7, which is a graph of % uninfected control versus time of addition (hrs), which shows results of time-of-addition studies of a cyanovirin, showing anti-HIV activity in CEM-SS cells infected with HIV-$1_{RF}$. Introduction of cyanovirin (●) or ddC (■) (10 nM and 5 μM concentrations, respectively) was delayed by various times after initial incubation, followed by 6 days incubation, then assay of cellular viability (linegraphs) and RT (open bars, inset). Points represent averages (±S.D.) of at least triplicate determinations. In marked contrast to the reverse transcriptase inhibitor ddC, delay of addition of cyanovirin-N by only 3 hrs resulted in little or no antiviral activity (FIG. 7). The aforementioned results suggested that cyanovirin-N inhibited HIV-infectivity by interruption of the initial interaction of the virus with the cell; this would, therefore, likely involve a direct interaction of cyanovirin-N with the viral gp120. This was confirmed by ultrafiltration experiments and dot-blot assays.

Ultrafiltration experiments were performed to determine if soluble gp120 and cyanovirin-N could bind directly, as assessed by inhibition of passage of cyanovirin-N through a 50 kDa-cutoff ultrafilter. Solutions of cyanovirin (30 μg) in PBS were treated with various concentrations of gp120 for 1 hr at 37° C., then filtered through a 50 kDa-cutoff centrifugal ultrafilter (Amicon). After washing 3 times with PBS, filtrates were desalted with 3 kDa ultrafilters; retentates were lyophilized, reconstituted in 100 μl H$_2$O and assayed for anti-HIV activity.

FIG. 8 is a graph of OD (450 nm) versus cyanovirin concentration (μg/ml), which illustrates cyanovirin/gp120 interactions defining gp120 as a principal molecular target of cyanovirin. Free cyanovirin-N was readily eluted, as evidenced by complete recovery of cyanovirin-N bioactivity in the filtrate. In contrast, filtrates from cyanovirin-N solutions treated with gp120 revealed a concentration-dependent loss of filtrate bioactivity; moreover, the 50kDa filter retentates were all inactive, indicating that cyanovirin-N and soluble gp120 interacted directly to form a complex incapable of binding to gp120 of intact virus.

There was further evidence of a direct interaction of cyanovirin-N and gp120 in a PVDF membrane dot-blot assay. A PVDF membrane was spotted with 5 μg CD4 (CD), 10 μg aprotinin (AP), 10 μg bovine globulin (BG), and decreasing amounts of cyanovirin; 6 μg [1], 3 μg [2], 1.5 μg [3], 0.75 μg [4], 0.38 μg [5], 0.19 μg [6], 0.09 μg [7], and 0.05 μg [8], then washed with PBST and visualized per manufacturer's recommendations. A dot blot of binding of cyanovirin and a gp120-HRP conjugate (Invitrogen) showed that cyanovirin-N specifically bound a horseradish peroxidase conjugate of gp120 (gp120-HRP) in a concentration-dependent manner.

Example 7

This example illustrates the preparation and biological activity of a composition of the present invention comprising a functional cyanovirin coupled to a solid support matrix.

Recombinant CV-N (rCV-N) produced in *E. coli* was compared with biotinylated CV-N (bCV-N) at 0.05 μg or 0.5 μg for in vitro inactivation of 100 TCID$_{50}$ of a primary isolate (HIV-1/UG/021/92) spiked into fetal bovine serum. Aliquots of 10$^4$ streptavidin-coated magnetic glass beads were reacted at room temperature with 0.5 μg bCV-N for 60 minutes and washed to remove free bCV-N. The binding of bCV-N to the beads was detected with polyclonal rabbit antibodies against CV-N, using FITC-labeled goat anti-rabbit IgG in flow cytometric analysis of the beads. The bead-bound sessile CV-N (sCV-N) and unbound control beads were tested for antiviral activity against 100 TCID$_{50}$ of HIV. Following incubation at 37° C. for 90 minutes, the viral supernates were cultured for 7 days in PHA-stimulated human PMBC, and the synthesis of P24 antigen was assessed.

At 0.5 μg, both rCV-N and bCV-N were equally effective in inactivating 100 TCID$_{50}$ of HIV; however, at 0.05 μg, they were only 40% effective in inactivating 100 TCID$_{50}$. The bead-bound sCV-N completely inactivated 100 TCID$_{50}$ of HIV, though a fraction of non-infectious HIV appeared to remain adherent to sCV-N as accessed by RT-PCR. Thus, matrix-anchored cyanovirin provides a practical and effective means to remove infectious virus from non-infectious virus in a sample.

Example 8

This example further illustrates the extraordinarily broad range of antiretroviral activity against diverse lab-adapted and clinical strains of human and nonhuman primate immunodeficiency retroviruses. Table 1 below shows the comparative ranges of anti-immunodeficiency virus activities of cyanovirin-N and sCD4 tested against a wide range of virus strains in diverse host cells. Particularly noteworthy is the similar potency of cyanovirin-N against both lab-adapted strains as well as clinical isolates of HIV. This was in sharp contrast to the lack of activity of sCD4 against the clinical isolates.

The EC$_{50}$ values (Table 1) were determined from concentration-response curves from eight dilutions of the test agents (averages from triplicate wells per concentration); G910-6 is an AZT-resistant strain; A17 is a pyridinone-resistant strain; HIV-1 Ba-L was tested in human peripheral blood macrophage (PBM) cultures by supernatant reverse transcriptase activity; all other assays employed XTT-tetrazolium (Gulakowski et al., 1991, supra). Further details of virus strains, cell lines, clinical isolates, and assay procedures are published (Buckheit et al., *AIDS Res. Hum. Retrovir.* 10, 1497–1506, 1994; Buckheit et al., *Antiviral Res.* 25, 43–56, 1994; and references contained therein). In Table 1, N.D.=not determined

TABLE 1

Comparative Ranges of Antiviral Activity of CV-N and sCD4

| | | $EC_{50}$ (nM)[a] | |
|---|---|---|---|
| Virus | Target Cells | Cyanovirin-N s | CD4 |
| HIV-1 Laboratory Strains | | | |
| RF | CEM-SS | 0.5 | 0.8 |
| RF | U937 | 0.5 | 0.1 |
| IIIB | CEM-SS | 0.4 | 1.6 |
| IIIB | MT-2 | 0.4 | 13 |
| MN | MT-2 | 2.3 | N.D. |
| G-910-6 | MT-2 | 5.8 | N.D. |
| A17 | MT-2 | 0.8 | 13 |
| HIV-1 Promonocytotropic Isolates | | | |
| 214 | CEM-SS | 0.4 | N.D. |
| SK1 | CEM-SS | 4.8 | N.D. |
| HIV-1 Lymphotropic Isolates | | | |
| 205 | CEM-SS | 0.8 | N.D. |
| G1 | CEM-SS | 0.9 | N.D. |
| HIV-1 Clinical Isolates | | | |
| WEJO | PBL | 6.7 | >100 |
| VIHU | PBL | 5.5 | >100 |
| BAKI | PBL | 1.5 | >100 |
| WOME | PBL | 4.3 | >100 |
| HIV-2 | | | |
| ROD | CEM-SS | 7.6 | >200 |
| MS | CEM-SS | 2.3 | N.D. |
| SIV | | | |
| Delta$_{B670}$ | 174xCEM | 11 | 3.0 |

Example 9

This example further illustrates the construction of a conjugate DNA coding sequence, and expression thereof, to provide a cyanovirin-toxin protein conjugate that selectively targets and kills HIV-infected cells. More specifically, this example illustrates construction and expression of a conjugate DNA coding sequence for a cyanovirin/Pseudomonas-exotoxin which selectively kills viral gp120-expressing host cells.

A DNA sequence (SEQ ID NO:3) coding for FLAG-cyanovirin-N and a DNA sequence coding for the PE38 fragment of Pseudomonas exotoxin (Kreitman et al., *Blood* 83, 426–434, 1994) were combined in the pFLAG-1 expression vector. The PE38 coding sequence was excised from a plasmid, adapted, and ligated to the C-terminal position of the FLAG-cyanovirin-N coding sequence using standard recombinant DNA procedures. This construct is illustrated schematically in FIG. 9. Transformation of *E. coli* with this construct, selection of clones, and induction of gene expression with IPTG resulted in production of a conjugate protein with the expected molecular weight and immunoreactivity on Western-blot analysis using an anti-FLAG antibody. The chimeric molecule was purified by FLAG-affinity chromatography (e.g., as in Example 4) and evaluated for toxicity to human lymphoblastoid cells infected with HIV (H9/IIIB cells) as well as their uninfected counterparts (H9 and CEM-SS cells). Cells were plated in 96-well microtitre plates and exposed to various concentrations of the conjugate protein (named PPE). After three days, viability was assessed using the XTT assay (Gulakowski et al., 1991, supra). FIG. 10 illustrates the results of this testing. As anticipated, the infected H9/IIIB cells expressing cell-surface gp120 were dramatically more sensitive to the toxic effects of PPE than were the uninfected H9 or CEM-SS cells. The $IC_{50}$ values determined from the concentration-effect curves were 0.014 nM for H9/IIIB compared to 0.48 and 0.42 nM for H9 and CEM-SS, respectively.

Example 10

This example illustrates transformation of a mammalian cell to express a cyanovirin therein.

A genetic construct suitable for demonstration of expression of a cyanovirin in mammalian cells was prepared by ligating a DNA sequence coding for FLAG-cyanovirin-N into the pFLAG CMV-1 expression vector (IBI-Kodak, Rochester, N.Y.). The FLAG-cyanovirin-N coding sequence (SEQ ID NO:3) was excised from a previously constructed plasmid and ligated to the pFLAG CMV-1 vector using standard recombinant DNA procedures. African green monkey cells (COS-7 cells, obtained from the American Type Culture Collection, Rockville, Md.) were transformed by exposure to the construct in DEAE dextran solution. To assess expression of FLAG-cyanovirin-N, cells were lysed after 72 hours and subjected to PAGE and Western blot analysis. Anti-FLAG immunoreactive material was readily detected in transformed COS-7 cells, albeit at an apparent molecular weight substantially greater than native recombinant FLAG-cyanovirin-N produced in *E. coli*. Diagnostic analyses of digests, performed in the same manner as in Example 11, which follows, indicated that this increased molecular weight was due to post-translational modification (N-linked oligosaccharides) of the FLAG-cyanovirin-N.

Example 11

This example illustrates transformation and expression of a cyanovirin in a non-mammalian cell, more specifically a yeast cell.

A genetic construct suitable for demonstration of expression of a cyanovirin in *Pichia pastoris* was prepared by ligating a DNA sequence coding for cyanovirin-N into the pPIC9 expression vector (Invitrogen Corporation, San Diego, Calif.). The cyanovirin-N coding sequence (SEQ ID NO:1) was excised from a previously constructed plasmid and ligated to the vector using standard recombinant DNA procedures. Yeast cells were transformed by electroporation and clones were selected for characterization. Several clones were found to express, and to secrete into the culture medium, material reactive with anti-cyanovirin-N polyclonal antibodies (see, e.g., Example 12).

Similar to the observations with the mammalian forms described in Example 10, the elevated apparent molecular weight of the yeast-derived product on PAGE and Western blot analysis, suggested that post-translational modification of the cyanovirin-N was occurring in this expression system.

To further define this modification, the secreted products from two clones were digested with peptide-N4-(N-acetyl-β-glucosaminyl) asparagine amidase. This enzyme, obtained from New England Biolabs (Beverly, Mass.), specifically cleaves oligosaccharide moieties attached to asparagine residues. This treatment reduced the apparent molecular weight of the product to that equivalent to native recombinant cyanovirin-N expressed in *E. coli*. Inspection of the amino acid sequence of cyanovirin revealed a single recognition motif for N-linked modification (linkage to the asparagine located at position 30).

To further establish this as the site of glycosylation, a mutation was introduced at this position to change the asparagine residue to glutamine (N30Q). Expression of this mutant form resulted in production of immunoreactive material with a molecular weight consistent with that of native recombinant FLAG-cyanovirin-N.

Example 12

This example further illustrates an antibody specifically binding to a cyanovirin.

Three 2-month old New Zealand White rabbits (1.8–2.2 kg) were subjected to an immunization protocol as follows: A total of 100 μg of cyanovirin-N was dissolved in 100 μl of a 1:1 suspension of phosphate-buffered saline (PBS) and Freunds incomplete adjuvant and administered by intramuscular injection at 2 sites on each hind leg; 8–16 months from the initial injection, a final boost of 50 μg of cyanovirin-N per rabbit was dissolved in 1000 μl of a 1:1 suspension of PBS and Freunds incomplete adjuvant and administered by intraperitoneal injection; on days 42, 70, 98 and 122, 10 ml of blood was removed from an ear vein of each rabbit; 14 days after the last intraperitoneal boost, the rabbits were sacrificed and bled out. The IgG fraction of the resultant immune sera from the above rabbits was isolated by protein-A Sepharose affinity chromatography according to the method of Goudswaard et al. (*Scand. J. Immunol.* 8, 21–28, 1978). The reactivity of this polyclonal antibody preparation for cyanovirin-N was demonstrated by western-blot analysis using a 1:1000 to 1:5000 dilution of the rabbit IgG fractions.

The antibody prepared according to the aforementioned procedure specifically bound to a protein of the present invention. SDS-PAGE of a whole-cell lysate, from *E. coli* strain DH5α engineered to produce cyanovirin-N, was carried out using 18% polyacrylamide resolving gels and standard discontinuous buffer systems according to Laemmeli (*Nature* 227, 680–685, 1970). Proteins were visualized by staining with Coomassie brilliant blue.For Western-blot analyses, proteins were electroeluted from the SDS-PAGE gel onto a nitrocellulose membrane. Non-specific binding sites on the membrane were blocked by washing in a 1% solution of bovine serum albumin (BSA). The membrane was then incubated in a solution of the IgG fraction from the aforementioned rabbit anti-cyanovirin-N immune serum diluted 1:3000 with phosphate buffered saline (PBS). Subsequently, the membrane was incubated in a secondary antibody solution containing goat-antirabbit-peroxidase conjugate (Sigma) diluted 1:10000. The bound secondary antibody complex was visualized by incubating the membrane in a chemiluminescence substrate and then exposing it to x-ray film.

One skilled in the art additionally will appreciate that, likewise by well-established, routine procedures (e.g., see Harlow and Lane, 1988, supra), monoclonal antibodies may be prepared using as the antigen a protein of the present invention, and that such a resulting monoclonal antibody likewise can be shown to be an antibody specifically binding a protein of the present invention.

Example 13

This example demonstrates the anti-influenza virus activity of cyanovirins, including glycosylation-resistant cyanovirins.

Host cells and influenza virus stocks used for these assays are routinely obtainable at the Southern Research Institute-Frederick (SoRI-Frederick, Frederick, Md.). MDCK cells were used for all assays. Those influenza virus strains and isolates that were used in the assays included the following: A/Sydney/5/97(H3N2), A/Victoria/3/75(H3N2); A/Beijing/262/95(H1N1); A/Mem/2/99(H3N2); A/Mem/8/99(H1N1); B/HK/5/72; B/Yamanashi/166/98; and B/Mem/3/99.

A typical antiviral assay for each virus was as follows. A pretreated aliquot of virus was removed from the freezer (−80° C.) and allowed to thaw. The virus was diluted into tissue culture medium such that the amount of virus added to each well in a volume of 100 μl was that amount pre-determined to give complete cell killing at 3–7 days (depending on the virus) post-infection. Cyanovirin-N (SEQ ID NO:2) stock solution was diluted into the medium to the desired high concentration and then further diluted in the medium in 0.5 $\log_{10}$ increments.

The day following plating of cells, plates were removed from the incubator, and medium was removed and discarded. The infection medium was DMEM (Dulbecco's Minimal Essential Medium) supplemented with 0.3% BSA, 100 U/ml penicillin, 100 μg/ml streptomycin, 0.1 mM non-essential amino acids, 0.1 mM sodium pyruvate, 2 mM L-glutamine and 2.0 μg/ml TPCK-treated (N-tosyl-L-phenylalanine ketone) trypsin. Drug dilutions (6–12 dilutions) were made in medium and added to appropriate wells of a 96-well microtiter plate in a volume of 100 μl per well. Each dilution was set up in triplicate. Infection medium containing appropriately diluted virus was added to appropriate wells of the microtiter plate. Each plate contained cell control wells (cells only), virus control wells (cells plus virus), drug toxicity control wells (cells plus drug only), drug colorimetric control wells (drug only) as well as experimental wells (drug plus cells plus virus).

After 7 days of incubation at 37° C. in a 5% $CO_2$ incubator, the test plates were analyzed by staining with Celltiter 96 reagent. Twenty microliters of the reagent were added to each well of the plate and the plate was reincubated for 4 hrs at 37° C. Celltiter 96 reagent contains a novel tetrazolium (MTS) compound and the electron-coupling reagent phenazine ethosulfate (PES). MTS-tetrazolium is bioreduced by cells into a colored formazan product that is soluble in tissue culture medium. This conversion is mediated by NADPH and NADH produced by dehydrogenase enzymes in metabolically active cells. The amount of soluble formazan produced by cellular reduction of the MTS was measured by the absorbance at 490 nm. The quantity of formazan product as measured by the amount of 490 nm absorbance was directly proportional to the number of living cells in the culture, thus allowing the rapid quantitative analysis of the inhibition of virus-induced cell killing by the test substances. The $IC_{50}$ (50% inhibition of virus replication), $TC_{50}$ (50% reduction in cell viability) and the corresponding therapeutic index (TI: $TC_{50}/IC_{50}$) were calculated routinely. Results from a typical battery of testing of cyanovirin-N (SEQ ID NO: 2) against diverse strains and isolates of influenza viruses A and B are shown below. As illustrated, cyanovirin-N has potent, broad-spectrum anti-influenza virus activity. For example, cyanovirin-N potently inhibited multiple virus subtypes, including representatives of the prominent human subtypes, H1N1 and H3N2, and recent clinical isolates and laboratory strains of influenza A and B.

| Anti-Influenza Virus Activity of Cyanovirin-N | | | | |
|---|---|---|---|---|
| Virus | Strain | $IC_{50}$ (μg/ml) | $TC_{50}$ (μg/ml) | TI |
| Influenza A (lab strains) | A/Sydney/5/97 (H3N2) | 0.04 | >10 | >228 |
| | A/Victoria/3/75 (H3N2) | 0.005 | >1 | >187 |
| | A/Beijing/262/95 (H1N1) | 0.01 | 6.6 | 548 |
| Influenza A (clinical strains) | A/Mem/2/99 (H3N2) | 0.15 | >10 | >68 |
| | A/Mem/8/99 (H1N1) | 0.03 | >10 | >399 |

-continued

Anti-Influenza Virus Activity of Cyanovirin-N

| Virus | Strain | IC$_{50}$ (µg/ml) | TC$_{50}$ (µg/ml) | TI |
|---|---|---|---|---|
| Influenza B (lab strains) | B/HK/5/72 | 0.70 | >10 | >14 |
| | B/Yamanashi/166/98 | 0.0037 | >1 | >270 |
| Influenza B (clinical strain) | B/Mem/3/99 | 0.02 | >10 | >473 |

Anti-influenza virus testing was also performed on illustrative glycosylation-resistant, functional cyanovirins including cyanovirins homologous to SEQ ID NO:2 in which the amino acid at position 30 is alanine, glutamine or valine instead of asparagine (said cyanovirins identified below as N30A, N30Q and N30V, respectively). Anti-influenza virus testing was likewise performed on additional illustrative glycosylation-resistant, functional cyanovirins homologous to SEQ ID NO:2 in which the amino acid at position 30 is alanine, glutamine or valine instead of asparagine, and, in each case, the amino acid at position 51 is glycine instead of proline (said cyanovirins identified below as N30A/P51G, N30Q/P51G and N30V/P51G, respectively). The construction and expression of the aforementioned six illustrative glycosylation-resistant, functional cyanovirins is described in Example 14. Testing results were as follows:

Anti-Influenza Virus Activity of Functional, Glycosylation-Resistant Cyanovirins

| Cyanovirin | Virus/Strain | IC$_{50}$ (µg/ml) | TC$_{50}$ (µg/ml) | TI |
|---|---|---|---|---|
| N30A | Influenza A/Sydney | 0.003 | >0.1 | >36 |
| | Influenza B/Yamanashi | 0.005 | >0.1 | >20 |
| N30Q | Influenza A/Sydney | 0.002 | >0.1 | >42 |
| | Influenza B/Yamanashi | 0.002 | >0.1 | >57 |
| N30V | Influenza A/Sydney | 0.001 | >0.1 | >112 |
| | Influenza B/Yamanashi | 0.001 | >0.1 | >169 |
| N30A/P51G | Influenza A/Sydney | 0.006 | >0.1 | >17 |
| | Influenza B/Yamanashi | 0.03 | >0.1 | >3 |
| N30Q/P51G | Influenza A/Sydney | 0.004 | >0.1 | >27 |
| | Influenza B/Yamanashi | 0.02 | >0.1 | >6 |
| N30V/P51G | Influenza A/Sydney | 0.005 | >0.1 | >20 |
| | Influenza B/Yamanashi | 0.02 | >0.1 | >6 |

Example 14

This example describes the construction of vectors comprising glycosylation-resistant cyanovirins for expression in isolated eukaryotic cells or eukaryotic organisms.

Routine procedures, well-known to those skilled in the art, were used to construct and express vectors incorporating nucleic acids encoding illustrative mutant cyanovirin proteins lacking a potential N-glycosylation site [asparagine-X-serine (or threonine), wherein X is any amino acid except proline or aspartic acid; specifically, asparagine30-threonine 31-serine32]. Starting with the previously described (Mori et al., Prot. Exp. Purif. 12, 223–228, 1998) pET(CV-N) plasmid encoding the native form of cyanovirin (SEQ ID NO:2), to replace Asn at the position 30 with Ala, Gln, or Val, QuikChange™ Site-Directed Mutagenesis Kits from Stratagene (La Jolla, Calif.) were utilized with the appropriate specific oligo DNA primer sets per manufacturer's instructions. DNA sequences of the resulting vectors, pET (Asn30Ala), pETAsn30Gln), and pET(Asn30Val), were confirmed, and the constructs were used to transform E. coli BL21 (DE3) (Novagen, Madison, Wis.). The recombinant mutant proteins were routinely induced with 1.0 mM IPTG, purified from the periplasmic fractions using a series of standard reverse-phase chromatography techniques as previously described (Boyd et al., Antimicrob. Agents Chemother. 41, 1521–1530, 1997; Mori et al., 1998, supra). Routine electrospray ionization mass spectrometry of the purified proteins confirmed the molecular ions consistent with the calculated values for the deduced amino acid sequences and at least 95% purity. Results from standard amino acid analyses of each recombinant protein were consistent with the sequences, and provided protein concentrations. SDS-PAGE analysis and immunoblotting were likewise performed using routine, conventional procedures.

Although many different changes or combinations of changes of amino acids can be made to eliminate a potential N-glycosylation site in a given protein (e.g., the Asn30-Thr31-Ser32 in SEQ ID NO:2), conservative changes that are less likely to perturb the tertiary structure of the functional protein are preferred. Selected mutations for evaluation can be arbitrary, or based on some consideration of the native protein structure. Ultimately, however, the critical determination of the impact of any mutation at the potential glycosylation site is whether or not the mutant protein a) is in fact glycosylation-resistant, and b) is in fact "functional," i.e., does, in fact, retain the desired biological activity, i.e., antiviral activity.

Accordingly, for the present demonstration, coding sequences and vectors first were constructed and expressed for three representative mutants, wherein the asparagine at position 30 of SEQ ID NO:2 was replaced by alanine, glutamine or valine. These three mutant proteins (identified in Example 13 as N30A, N30Q and N30V, respectively), expressed and purified by the aforementioned methods and references, showed high purity and the expected molecular masses, and were all appropriately immunoreactive with anti-cyanovirin antibodies. Testing of the three mutant proteins against selected representative influenza A and B viruses, using the methods described herein, confirmed that these mutants had anti-influenza virus activity indistinguishable from native cyanovirin-N (SEQ ID NO:2) (see Example 13).

As an additional confirmation, DNA coding sequences and corresponding vectors were constructed and expressed routinely, as above, for three additional mutants, comprising the sequences of the aforementioned three glycosylation-resistant mutants, and, in each case, comprising a further mutation wherein the proline at position 51 was, instead, glycine (identified in Example 13 as N30A/P51G and N30Q/P51G, respectively). Testing of these mutants, which are homologs of SEQ ID NO:2 in which the amino acid at position 30 is alanine, glutamine or valine, and the amino acid at position 51 is glycine, against representative influenza viruses as described herein revealed potent anti-influenza virus activity comparable to the native cyanovirin-N (SEQ ID NO:2) (see Example 13).

As a final demonstration, the glycosylation resistance of any of the aforementioned mutants comprising a homolog of SEQ ID NO:2 in which the amino acid at position 30 was alanine, glutamine or valine and, optionally, the amino acid at position 51 was glycine, can be expressed in yeast, using similarly routine procedures, and tested against selected influenza viruses as herein described. These yeast-expressed mutants can be shown to be comparably potent against influenza viruses as is the control, bacterially expressed cyanovirin-N.

All of the references cited herein are hereby incorporated in their entireties by reference.

While this invention has been described with an emphasis upon preferred embodiments, it will be obvious to those of

What is claimed is:

1. An antiviral protein or antiviral peptide comprising a variant of SEQ ID NO:2, the variation consisting of a modification of amino acids 30–32 to render the amino acids glycosylation-resistant and optionally modification of amino acid 51, or a fragment of the variant which comprises at least nine contiguous amino acids, wherein the at least nine contiguous amino acids include the modification to amino acids 30–32 and the fragment has antiviral activity.

2. The antiviral protein or antiviral peptide of claim 1, in which the variant of amino acids 30–32 of SEQ ID NO:2 has been rendered glycosylation resistant by deletion or substitution of amino acid 30.

3. The antiviral protein or antiviral peptide of claim 2, in which amino acid 30 has been substituted with an amino acid selected from the group consisting of alanine, glutamine and valine and, if the at least nine contiguous amino acids of the SEQ ID NO:2 variant further comprise amino acid 51, optionally, amino acid 51 has been deleted or substituted.

4. The antiviral protein or antiviral peptide of claim 3, wherein amino acid 51 has been substituted with glycine.

5. A conjugate comprising the antiviral protein or antiviral peptide of claim 1 and at least one effector component selected from the group consisting of polyethylene glycol, albumin, dextran, a toxin and an immunological reagent.

6. A conjugate comprising the antiviral protein or antiviral peptide of claim 2 and at least one effector component selected from the group consisting of polyethylene glycol, albumin, dextran, a toxin and an immunological reagent.

7. A conjugate comprising the antiviral protein or antiviral peptide of claim 3 and at least one effector component selected from the group consisting of polyethylene glycol, albumin, dextran, a toxin and an immunological reagent.

8. A conjugate comprising the antiviral protein or antiviral peptide of claim 4 and at least one effector component selected from the group consisting of polyethylene glycol, albumin, dextran, a toxin and an immunological reagent.

9. A composition comprising an antiviral effective amount of the antiviral protein or antiviral peptide of claim 1.

10. A composition comprising an antiviral effective amount of the antiviral protein or antiviral peptide of claim 2.

11. A composition comprising an antiviral effective amount of the antiviral protein or antiviral peptide of claim 3.

12. A composition comprising an antiviral effective amount of the antiviral protein or antiviral peptide of claim 4.

13. A composition comprising an antiviral effective amount of the conjugate of claim 5.

14. A composition comprising an antiviral effective amount of the conjugate of claim 6.

15. A composition comprising an antiviral effective amount of the conjugate of claim 7.

16. A composition comprising an antiviral effective amount of the conjugate of claim 8.

17. A method of inhibiting prophylactically or therapeutically a viral infection of a host, which method comprises administering to the host an effective amount of the antiviral protein or antiviral peptide of claim 1 or an antiviral conjugate of either of the foregoing.

18. The method of claim 17, wherein the viral infection is an influenza viral infection.

19. The method of claim 17, wherein the antiviral protein, antiviral peptide, or antiviral conjugate is administered topically to the host.

20. The method of claim 19, wherein the antiviral protein, antiviral peptide, or antiviral conjugate is administered topically to the respiratory system.

21. The method of claim 20, wherein the antiviral protein, antiviral peptide, or antiviral conjugate is administered as an aerosol or microparticulate powder.

22. A method of inhibiting prophylactically or therapeutically an influenza viral infection of a host, which method comprises administering to the host an effective amount of an antiviral protein, antiviral peptide, antiviral protein conjugate or antiviral peptide conjugate comprising SEQ ID NO:2 or a fragment thereof comprising at least nine contiguous amino acids of SEQ ID NO:2, wherein the at least nine contiguous amino acids are nonglycosylated and have antiviral activity, whereupon the influenza viral infection is inhibited.

23. The method of claim 22, wherein the antiviral protein, antiviral peptide, antiviral protein conjugate or antiviral peptide conjugate is administered topically to the host.

24. The method of claim 23, wherein the antiviral protein, antiviral peptide, antiviral protein conjugate or antiviral peptide conjugate is administered topically to the respiratory system.

25. The method of claim 24, wherein the antiviral protein, antiviral peptide, antiviral protein conjugate or antiviral peptide conjugate is administered as an aerosol or microparticulate powder.

26. A method of inhibiting prophylactically or therapeutically a viral infection of a host, which method comprises administering to the host an effective amount of the antiviral protein or antiviral peptide of claim 2.

27. A method of inhibiting prophylactically or therapeutically a viral infection of a host, which method comprises administering to the host an effective amount of the antiviral protein or antiviral peptide of claim 3.

28. A method of inhibiting prophylactically or therapeutically a viral infection of a host, which method comprises administering to the host an effective amount of the antiviral protein or antiviral peptide of claim 4.

29. A method of inhibiting prophylactically or therapeutically an influenza viral infection of a host, which method comprises administering to the host an effective amount of the antiviral protein or antiviral peptide of claim 1.

30. A method of inhibiting prophylactically or therapeutically an influenza viral infection of a host, which method comprises administering to the host an effective amount of the antiviral protein or antiviral peptide of claim 2.

31. The method of claim 30, wherein amino acid 30 has been substituted with an amino acid selected from the group consisting of alanine, glutamine and valine and, if the at least nine contiguous amino acids of the SEQ ID NO:2 variant further comprise amino acid 51, optionally, amino acid 51 has been deleted or substituted.

32. The method of claim 31, wherein amino acid 51 has been substituted with glycine.

33. A method of inhibiting a viral infection of an animal, which method comprises transforming in vivo host cells with the nucleic acid molecule of claim 18, wherein the encoded antiviral protein or antiviral peptide is expressed and inhibits infection of the animal with a virus.

34. The method of claim 33, the nucleic acid molecule encodes an amino acid sequence wherein the variant of the amino acids 30–32 of SEQ ID NO:2 has been rendered glycosylation resistant by deletion or substitution of amino acid 30.

35. The method of claim 34, wherein amino acid 30 has been substituted with an amino acid selected from the group consisting of alanine, glutamine and valine and, if the at least nine contiguous amino acids of the SEQ ID NO:2 variant further comprise amino acid 51, optionally, amino acid 51 has been deleted or substituted.

36. The method of claim 35, wherein amino acid 51 has been substituted with glycine.

37. An isolated and purified nucleic acid molecule that encodes the antiviral protein or antiviral peptide of claim 1.

38. The isolated and purified nucleic acid molecule of claim 37, in which the variant of amino acids 30–32 of SEQ ID NO:2 has been rendered glycosylation resistant by deletion or substitution of amino acid 30.

39. The isolated and purified nucleic acid molecule of claim 38, in which amino acid 30 has been substituted with an amino acid selected from the group consisting of alanine, glutamine and valine and, if the at least nine contiguous amino acids of the SEQ ID NO:2 variant further comprise amino acid 51, optionally, amino acid 51 has been deleted or substituted.

40. The isolated and purified nucleic acid molecule of claim 39, wherein amino acid 51 has been substituted with glycine.

41. A vector comprising the isolated and purified nucleic acid molecule of claim 37.

42. A vector comprising the isolated and purified nucleic acid molecule of claim 38.

43. A vector comprising the isolated and purified nucleic acid molecule of claim 39.

44. A vector comprising the isolated and purified nucleic acid molecule of claim 40.

45. A host cell or microbial organism comprising the vector of claim 41.

46. A host cell or microbial organism comprising the vector of claim 42.

47. A host cell or microbial organism comprising the vector of claim 43.

48. A host cell or microbial organism comprising the vector of claim 44.

49. A method of producing an antiviral protein or antiviral peptide, which method comprises expressing the vector of claim 41 in a host cell or microbial organism.

50. A method of producing an antiviral protein or antiviral peptide, which method comprises expressing the vector of claim 42 in a host cell or microbial organism.

51. A method of producing an antiviral protein or antiviral peptide, which method comprises expressing the vector of claim 43 in a host cell or microbial organism.

52. A method of producing an antiviral protein or antiviral peptide, which method comprises expressing the vector of claim 44 in a host cell or microbial organism.

53. A method of inhibiting a viral infection of an animal, which method comprises transforming host cells with the nucleic acid molecule of claim 37, wherein the encoded antiviral protein or said antiviral peptide is expressed and inhibits infection of the animal with a virus.

54. The method of claim 53, wherein the host cells are autologous or homologous mammalian cells.

55. The method of claim 54, wherein the nucleic acid molecule encodes an amino acid sequence wherein the amino acids 30–32 of SEQ ID NO:2 are not glycosylated because they have been rendered glycosylation resistant by deletion or substitution of amino acid 30.

56. The method of claim 55, wherein amino acid 30 has been substituted with an amino acid selected from the group consisting of alanine, glutamine and valine and, if the at least nine contiguous amino acids of the SEQ ID NO:2 variant further comprise amino acid 51, optionally amino acid 51 has been deleted or substituted.

57. The method of claim 56, wherein amino acid 51 has been substituted with glycine.

* * * * *

UNITED STATES PATENT AND TRADEMARK OFFICE
CERTIFICATE OF CORRECTION

PATENT NO. : 6,780,847 B2
DATED : August 24, 2004
INVENTOR(S) : Boyd et al.

It is certified that error appears in the above-identified patent and that said Letters Patent is hereby corrected as shown below:

<u>Title page,</u>
Item [75], Inventors, the following should be added:
-- Barry R. O'Keefe, Frederick, MD (US)
Toshiyuki Mori, Germantown, MD (US)
Angela M. Gronenborn, Bethesda, MD (US) --

Item [56], References Cited, U.S. PATENT DOCUMENTS, should read as follows:

| | | |
|---|---|---|
| --3,470,067 A | 9/1969 | Warren et al. |
| 4,795,740* | 1/1989 | Cohen et al..................514/14 |
| 5,104,854* | 4/1992 | Schlesinger et al...........514/15 |
| 5,266,478 A | 11/1993 | Chang et al. |
| 5,445,960 A | 8/1995 | Masuho et al. |
| 5,558,865 A | 9/1996 | Ohno |
| 5,618,922 A | 4/1997 | Ohno et al. |
| 6,420,336 B1 * | 7/2002 | Boyd........................514/2 -- |

Signed and Sealed this

Eighteenth Day of January, 2005

JON W. DUDAS
*Director of the United States Patent and Trademark Office*